US012698343B2

(12) United States Patent
Xu et al.

(10) Patent No.: US 12,698,343 B2
(45) Date of Patent: Aug. 4, 2026

(54) COMBINATION OF BISPECIFIC FUSION PROTEIN AND ANTI-Her2 ANTIBODY FOR TUMOR TREATMENT

(71) Applicant: JIANGSU ALPHAMAB BIOPHARMACEUTICALS CO., LTD., Suzhou (CN)

(72) Inventors: Ting Xu, Suzhou (CN); Kangping Guo, Suzhou (CN); Junfang Xu, Suzhou (CN); Pilin Wang, Suzhou (CN); Yuhao Jin, Suzhou (CN)

(73) Assignee: JIANGSU ALPHAMAB BIOPHARMACEUTICALS CO., LTD., Suzhou (CN)

( * ) Notice: Subject to any disclaimer, the term of this patent is extended or adjusted under 35 U.S.C. 154(b) by 1018 days.

(21) Appl. No.: 17/782,445

(22) PCT Filed: Dec. 3, 2020

(86) PCT No.: PCT/CN2020/133667
§ 371 (c)(1),
(2) Date: Jun. 3, 2022

(87) PCT Pub. No.: WO2021/110107
PCT Pub. Date: Jun. 10, 2021

(65) Prior Publication Data
US 2023/0017515 A1 Jan. 19, 2023

(30) Foreign Application Priority Data

Dec. 4, 2019 (WO) ............... PCT/CN2019/123070
Nov. 9, 2020 (WO) ............... PCT/CN2020/127559

(51) Int. Cl.
C07K 16/32 (2006.01)
A61K 39/00 (2006.01)
A61P 35/00 (2006.01)
C07K 16/28 (2006.01)

(52) U.S. Cl.
CPC ............. C07K 16/32 (2013.01); A61P 35/00 (2018.01); C07K 16/2818 (2013.01); C07K 16/2827 (2013.01); A61K 2039/507 (2013.01); A61K 2039/545 (2013.01); C07K 2317/31 (2013.01)

(58) Field of Classification Search
None
See application file for complete search history.

(56) References Cited

U.S. PATENT DOCUMENTS

| | | | |
|---|---|---|---|
| 11,225,522 B2 * | 1/2022 | Xu | C07K 16/28 |
| 2019/0233519 A1 * | 8/2019 | Zhang | C07K 16/2827 |

FOREIGN PATENT DOCUMENTS

| | | | |
|---|---|---|---|
| CN | 105820251 A | 8/2016 | |
| CN | 106397592 A | 2/2017 | |
| CN | 107400166 A | 11/2017 | |
| JP | 2018504113 A | 2/2018 | |
| JP | 2021526377 A | 10/2021 | |
| WO | WO-2017198212 A1 * | 11/2017 | ............. A61P 31/22 |

OTHER PUBLICATIONS

Su et al (Cell, vol. 175, Issue 2, 442-457.e23; Oct. 2018) (Year: 2018).*
Lussier et al. (J. immunotherapy cancer 3, 21 (2015) (Year: 2015).*
PCT/CN2020/133667 International Search Report dated Mar. 3, 2021.
Coward, J., et al., Preliminary safety, efficacy, and ppharmacokinetics (PK) results of KN046 (bispecific anti-PD-L1/CTLA4) from a first-in-human study in subjects with advanced solid tumors, J of Clinical Oncology, vol. 37, No. 15 Suppl., May 26, 2019.
Gong, J.F., et al., Preliminary Safety, Tolerability and Efficacy Results of KN026 (A HER-2-Targeted Bispecific Antibody) in Combination with KN046 (an AntiPD-L1/CTLA-4 Bispecific Antibody) in Patients (PTS) with HER2 Aberrated Solid Tumors, J Immunother Cancer, vol. 8, No. Suppl 3, Nov. 9, 2020.
Jiangsu Alphamab Biopharmaceuticals Co., Ltd., NCT04521179, https://clinicaltrials.gov/ct2/history/NCT04521179?V_2=View#StudyPageTop, Aug. 19, 2020.
Peking university, NCT04040699, https://clinicaltrials.gov/ct2/show/record/NCT04040699?id=NCT04040699&draw=2&rank=1&load=cart, Brief Title, Intervention, Study Arms, Nov. 13, 2019.
European 20895879.3 Extended European Search Report dated Aug. 9, 2023.
Labrijn, A.F., et al., Bispecific antibodies: a mechanistic review of the pipeline, Nature Reviews, Drug Discovery, Nature Publishing Group, GB, vol. 18, No. 8, pp. 585-608, Jun. 7, 2019 (Aug. 2019).
Shen, L., KN026 Combined with KN046 in Subjects with HER2 Positive Solid Tumor, Clinical Trials.gov, Aug. 1, 2019.
Tan, S., et al., Distinct PD-L1 binding characteristics of therapeutic monoclonal antibody durvalumab, Protein & Cell, vol. 9, No. 1, pp. 135-139, The Author(s), May 9, 2017 (2018).

* cited by examiner

*Primary Examiner* — Zachariah Lucas
*Assistant Examiner* — Sarah A Alsomairy
(74) *Attorney, Agent, or Firm* — Sughrue Mion, PLLC

(57) ABSTRACT

The present disclosure provides a use of an immune checkpoint inhibitor in combination with a Her2 inhibitor in the preparation of a medicament for treating tumor in a subject in need thereof, and also provides a pharmaceutical composition comprising an effective amount of said immune checkpoint inhibitor and an effective amount of said Her2 inhibitor, and optionally a pharmaceutically acceptable excipient, as well as a use of the pharmaceutical composition in the preparation of a medicament for treating tumor in a subject in need thereof.

12 Claims, 1 Drawing Sheet
Specification includes a Sequence Listing.

A

B a b

SEQUENCE LISTING

```
<160> NUMBER OF SEQ ID NOS: 90

<210> SEQ ID NO 1
<211> LENGTH: 19
<212> TYPE: PRT
<213> ORGANISM: Artificial Sequence
<220> FEATURE:
<223> OTHER INFORMATION: CDR3 of antiPD-L1
<220> FEATURE:
<221> NAME/KEY: misc_feature
<222> LOCATION: (4)..(4)
<223> OTHER INFORMATION: Xaa = Glu or Gly
<220> FEATURE:
<221> NAME/KEY: misc_feature
<222> LOCATION: (5)..(5)
<223> OTHER INFORMATION: Xaa = Asp or Tyr
<220> FEATURE:
<221> NAME/KEY: misc_feature
<222> LOCATION: (9)..(9)
<223> OTHER INFORMATION: Xaa = Pro or Thr
<220> FEATURE:
<221> NAME/KEY: misc_feature
<222> LOCATION: (10)..(10)
<223> OTHER INFORMATION: Xaa = Gly or Leu
<220> FEATURE:
<221> NAME/KEY: misc_feature
<222> LOCATION: (11)..(11)
<223> OTHER INFORMATION: Xaa = Pro or Val
<220> FEATURE:
<221> NAME/KEY: misc_feature
<222> LOCATION: (12)..(12)
<223> OTHER INFORMATION: Xaa = Ala or Thr

<400> SEQUENCE: 1

Asp Ser Phe Xaa Xaa Pro Thr Cys Xaa Xaa Xaa Xaa Ser Ser Gly Ala
1               5                   10                  15

Phe Gln Tyr

<210> SEQ ID NO 2
<211> LENGTH: 10
<212> TYPE: PRT
<213> ORGANISM: Artificial Sequence
<220> FEATURE:
<223> OTHER INFORMATION: CDR1 of antiPD-L1
<220> FEATURE:
<221> NAME/KEY: misc_feature
<222> LOCATION: (2)..(2)
<223> OTHER INFORMATION: Xaa = Lys or Asn
<220> FEATURE:
<221> NAME/KEY: misc_feature
<222> LOCATION: (3)..(3)
<223> OTHER INFORMATION: Xaa = Ile or Met
<220> FEATURE:
```

-continued

```
<221> NAME/KEY: misc_feature
<222> LOCATION: (4)..(4)
<223> OTHER INFORMATION: Xaa = Ile or Ser
<220> FEATURE:
<221> NAME/KEY: misc_feature
<222> LOCATION: (5)..(5)
<223> OTHER INFORMATION: Xaa = Arg or Ser
<220> FEATURE:
<221> NAME/KEY: misc_feature
<222> LOCATION: (6)..(6)
<223> OTHER INFORMATION: Xaa = Arg or Val

<400> SEQUENCE: 2

Gly Xaa Xaa Xaa Xaa Xaa Arg Cys Met Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: PD-L1 ISVD-9 CDR1

<400> SEQUENCE: 3

Gly Lys Met Ser Ser Arg Arg Cys Met Ala
1               5                   10

<210> SEQ ID NO 4
<211> LENGTH: 17
<212> TYPE: PRT
<213> ORGANISM: Artificial Sequence
<220> FEATURE:
<223> OTHER INFORMATION: PD-L1 ISVD-9 CDR2

<400> SEQUENCE: 4

Lys Leu Leu Thr Thr Ser Gly Ser Thr Tyr Leu Ala Asp Ser Val Lys
1               5                   10                  15

Gly

<210> SEQ ID NO 5
<211> LENGTH: 19
<212> TYPE: PRT
<213> ORGANISM: Artificial Sequence
<220> FEATURE:
<223> OTHER INFORMATION: PD-L1 ISVD-9 CDR3

<400> SEQUENCE: 5

Asp Ser Phe Glu Asp Pro Thr Cys Thr Leu Val Thr Ser Ser Gly Ala
1               5                   10                  15

Phe Gln Tyr

<210> SEQ ID NO 6
<211> LENGTH: 128
<212> TYPE: PRT
<213> ORGANISM: Artificial Sequence
<220> FEATURE:
<223> OTHER INFORMATION: PD-L1 ISVD-9

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
            35                  40                  45
```

-continued

```
Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Leu Val Thr Val Ser Ser
        115                 120                 125
```

```
<210> SEQ ID NO 7
<211> LENGTH: 10
<212> TYPE: PRT
<213> ORGANISM: Artificial Sequence
<220> FEATURE:
<223> OTHER INFORMATION: PD-L1 ISVD-6 CDR1

<400> SEQUENCE: 7

Gly Asn Ile Ile Arg Val Arg Cys Met Ala
1               5                   10
```

```
<210> SEQ ID NO 8
<211> LENGTH: 17
<212> TYPE: PRT
<213> ORGANISM: Artificial Sequence
<220> FEATURE:
<223> OTHER INFORMATION: PD-L1 ISVD-6 CDR2

<400> SEQUENCE: 8

Asn Ile Leu Thr Thr Thr Ile Ser Thr Tyr Leu Ala Asp Ser Val Lys
1               5                   10                  15

Gly
```

```
<210> SEQ ID NO 9
<211> LENGTH: 19
<212> TYPE: PRT
<213> ORGANISM: Artificial Sequence
<220> FEATURE:
<223> OTHER INFORMATION: PD-L1 ISVD-6 CDR3

<400> SEQUENCE: 9

Asp Ser Phe Gly Tyr Pro Thr Cys Pro Gly Pro Ala Ser Ser Gly Ala
1               5                   10                  15

Phe Gln Tyr
```

```
<210> SEQ ID NO 10
<211> LENGTH: 128
<212> TYPE: PRT
<213> ORGANISM: Artificial Sequence
<220> FEATURE:
<223> OTHER INFORMATION: PD-L1 ISVD-6

<400> SEQUENCE: 10

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
                20                  25                  30

Cys Met Ala Trp Phe Arg Gln Ala Pro Gly Lys Glu Arg Glu Arg Gly
        35                  40                  45

Pro Asn Ile Leu Thr Thr Thr Ile Ser Thr Tyr Leu Ala Asp Ser Val
    50                  55                  60
```

```
Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
            100                 105                 110

Gly Ala Phe Gln Tyr Trp Gly Gln Gly Thr Gln Val Thr Val Ser Ser
        115                 120                 125

<210> SEQ ID NO 11
<211> LENGTH: 17
<212> TYPE: PRT
<213> ORGANISM: Artificial Sequence
<220> FEATURE:
<223> OTHER INFORMATION: PD-L1 ISVD-m3 CDR2

<400> SEQUENCE: 11

Asp Val Asn Pro Asn Ser Gly Gly Ser Ile Tyr Asn Gln Arg Phe Lys
1               5                   10                  15

Gly

<210> SEQ ID NO 12
<211> LENGTH: 128
<212> TYPE: PRT
<213> ORGANISM: Artificial Sequence
<220> FEATURE:
<223> OTHER INFORMATION: PD-L1 ISVD-m3

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
            35                  40                  45

Ala Asp Val Asn Pro Asn Ser Gly Gly Ser Ile Tyr Asn Gln Arg Phe
        50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

<210> SEQ ID NO 13
<211> LENGTH: 128
<212> TYPE: PRT
<213> ORGANISM: Artificial Sequence
<220> FEATURE:
<223> OTHER INFORMATION: PD-L1 ISVD-4

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
```

-continued

```
             35                   40                   45

Ala Lys Leu Leu Thr Thr Ser Gly Ser Thr Tyr Leu Ala Asp Ser Val
    50                   55                   60

Lys Gly Arg Phe Thr Ile Ser Gln Asn Asn Ala Lys Ser Thr Val Tyr
65                   70                   75                   80

Leu Gln Met Asn Ser Leu Lys Pro Glu Asp Thr Ala Met Tyr Tyr Cys
                85                   90                   95

Ala Ala Asp Ser Phe Glu Asp Pro Thr Cys Thr Leu Val Thr Ser Ser
                100                  105                  110

Gly Ala Phe Gln Tyr Trp Gly Gln Gly Thr Gln Val Thr Val Ser Ser
            115                  120                  125

<210> SEQ ID NO 14
<211> LENGTH: 128
<212> TYPE: PRT
<213> ORGANISM: Artificial Sequence
<220> FEATURE:
<223> OTHER INFORMATION: PD-L1 ISVD-11

<400> SEQUENCE: 14

Gln Val Gln Leu Val Glu Ser Gly Gly Gly Leu Val Gln Pro Gly Gly
1                   5                    10                   15

Ser Leu Arg Leu Ser Cys Ala Ala Ser Gly Lys Met Ser Ser Arg Arg
                20                   25                   30

Cys Met Ala Trp Phe Arg Gln Ala Pro Gly Lys Gly Leu Glu Arg Val
            35                   40                   45

Ala Lys Leu Leu Thr Thr Ser Gly Ser Thr Tyr Leu Ala Asp Ser Val
    50                   55                   60

Lys Gly Arg Phe Thr Ile Ser Arg Asp Asn Ser Lys Asn Thr Val Tyr
65                   70                   75                   80

Leu Gln Met Asn Ser Leu Arg Ala Glu Asp Thr Ala Val Tyr Tyr Cys
                85                   90                   95

Ala Ala Asp Ser Phe Glu Asp Pro Thr Cys Thr Leu Val Thr Ser Ser
                100                  105                  110

Gly Ala Phe Gln Tyr Trp Gly Gln Gly Thr Leu Val Thr Val Ser Ser
            115                  120                  125

<210> SEQ ID NO 15
<211> LENGTH: 128
<212> TYPE: PRT
<213> ORGANISM: Artificial Sequence
<220> FEATURE:
<223> OTHER INFORMATION: PD-L1 ISVD-13

<400> SEQUENCE: 15

Gln Val Gln Leu Val Glu Ser Gly Gly Gly Leu Val Gln Pro Gly Gly
1                   5                    10                   15

Ser Leu Arg Leu Ser Cys Ala Ala Ser Gly Lys Met Ser Ser Arg Arg
                20                   25                   30

Cys Met Ala Trp Phe Arg Gln Ala Pro Gly Lys Glu Arg Glu Arg Val
            35                   40                   45

Ala Lys Leu Leu Thr Thr Ser Gly Ser Thr Tyr Leu Ala Asp Ser Val
    50                   55                   60

Lys Gly Arg Phe Thr Ile Ser Arg Asp Asn Ser Lys Asn Thr Val Tyr
65                   70                   75                   80

Leu Gln Met Asn Ser Leu Lys Ala Glu Asp Thr Ala Val Tyr Tyr Cys
                85                   90                   95
```

-continued

```
Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

<210> SEQ ID NO 16
<211> LENGTH: 17
<212> TYPE: PRT
<213> ORGANISM: Artificial Sequence
<220> FEATURE:
<223> OTHER INFORMATION: CDR2 of CTLA4
<220> FEATURE:
<221> NAME/KEY: misc_feature
<222> LOCATION: (3)..(3)
<223> OTHER INFORMATION: Xaa = Ser or Tyr
<220> FEATURE:
<221> NAME/KEY: misc_feature
<222> LOCATION: (4)..(4)
<223> OTHER INFORMATION: Xaa = Ile or Leu

<400> SEQUENCE: 16

Ala Ile Xaa Xaa Gly Gly Gly Ser Thr Tyr Tyr Ala Asp Ser Val Lys
1               5                   10                  15

Gly

<210> SEQ ID NO 17
<211> LENGTH: 5
<212> TYPE: PRT
<213> ORGANISM: Artificial Sequence
<220> FEATURE:
<223> OTHER INFORMATION: CTLA4 ISVD-34 CDR1

<400> SEQUENCE: 17

Ala Tyr Cys Met Gly
1               5

<210> SEQ ID NO 18
<211> LENGTH: 17
<212> TYPE: PRT
<213> ORGANISM: Artificial Sequence
<220> FEATURE:
<223> OTHER INFORMATION: CTLA4 ISVD-34 CDR2

<400> SEQUENCE: 18

Ala Ile Tyr Ile Gly Gly Gly Ser Thr Tyr Tyr Ala Asp Ser Val Lys
1               5                   10                  15

Gly

<210> SEQ ID NO 19
<211> LENGTH: 19
<212> TYPE: PRT
<213> ORGANISM: Artificial Sequence
<220> FEATURE:
<223> OTHER INFORMATION: CTLA4 ISVD-34 CDR3

<400> SEQUENCE: 19

Asp Val Ile Pro Thr Glu Thr Cys Leu Gly Gly Ser Trp Ser Gly Pro
1               5                   10                  15

Phe Gly Tyr

<210> SEQ ID NO 20
<211> LENGTH: 128
<212> TYPE: PRT
<213> ORGANISM: Artificial Sequence
<220> FEATURE:
<223> OTHER INFORMATION: CTLA4 ISVD-34
```

<400> SEQUENCE: 20

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Tyr Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125
```

<210> SEQ ID NO 21
<211> LENGTH: 17
<212> TYPE: PRT
<213> ORGANISM: Artificial Sequence
<220> FEATURE:
<223> OTHER INFORMATION: CTLA4 ISVD-C1 CDR2

<400> SEQUENCE: 21

```
Ala Ile Tyr Leu Gly Gly Gly Ser Thr Tyr Tyr Ala Asp Ser Val Lys
1               5                   10                  15

Gly
```

<210> SEQ ID NO 22
<211> LENGTH: 128
<212> TYPE: PRT
<213> ORGANISM: Artificial Sequence
<220> FEATURE:
<223> OTHER INFORMATION: CTLA4 ISVD-C1

<400> SEQUENCE: 22

```
Gln Val Gln Leu Gln Glu Ser Gly Gly Gly Ser Val Gln Ala Gly Gly
1               5                   10                  15

Ser Leu Gly Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Leu Gly Gly Gly Ser Thr Tyr Tyr Ala Asp Ser Val
    50                  55                  60

Lys Gly Arg Phe Thr Ile Ser Gln Asp Ile Ala Lys Asn Thr Leu Tyr
65                  70                  75                  80

Leu Gln Met Asn Ser Leu Lys Pro Glu Asp Thr Ala Met Tyr Ser Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
        115                 120                 125
```

<210> SEQ ID NO 23
<211> LENGTH: 17

```
<212> TYPE: PRT
<213> ORGANISM: Artificial Sequence
<220> FEATURE:
<223> OTHER INFORMATION: CTLA4 ISVD-13 CDR2

<400> SEQUENCE: 23

Ala Ile Ser Ile Gly Gly Gly Ser Thr Tyr Tyr Ala Asp Ser Val Lys
1               5                   10                  15

Gly

<210> SEQ ID NO 24
<211> LENGTH: 128
<212> TYPE: PRT
<213> ORGANISM: Artificial Sequence
<220> FEATURE:
<223> OTHER INFORMATION: CTLA4 ISVD-13

<400> SEQUENCE: 24

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Gly Ser Thr Tyr Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
        115                 120                 125

<210> SEQ ID NO 25
<211> LENGTH: 128
<212> TYPE: PRT
<213> ORGANISM: Artificial Sequence
<220> FEATURE:
<223> OTHER INFORMATION: CTLA4 ISVD-26

<400> SEQUENCE: 25

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Gly Ser Thr Tyr Tyr Ala Asp Ser Val
    50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125
```

```
<210> SEQ ID NO 26
<211> LENGTH: 128
<212> TYPE: PRT
<213> ORGANISM: Artificial Sequence
<220> FEATURE:
<223> OTHER INFORMATION: CTLA4 ISVD-27

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 27
<211> LENGTH: 128
<212> TYPE: PRT
<213> ORGANISM: Artificial Sequence
<220> FEATURE:
<223> OTHER INFORMATION: CTLA4 ISVD-28

<400> SEQUENCE: 27

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Val Gly Val
        35                  40                  45

Ala Ala Ile Ser Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 28
<211> LENGTH: 128
<212> TYPE: PRT
<213> ORGANISM: Artificial Sequence
<220> FEATURE:
<223> OTHER INFORMATION: CTLA4 ISVD-29

<400> SEQUENCE: 28
```

-continued

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Ser Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
                100                 105                 110

Gly Pro Phe Gly Tyr Trp Gly Gln Gly Thr Leu Val Thr Val Ser Ser
            115                 120                 125

<210> SEQ ID NO 29
<211> LENGTH: 128
<212> TYPE: PRT
<213> ORGANISM: Artificial Sequence
<220> FEATURE:
<223> OTHER INFORMATION: CTLA4 ISVD-30

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Ser Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
                100                 105                 110

Gly Pro Phe Gly Tyr Trp Gly Gln Gly Thr Leu Val Thr Val Ser Ser
            115                 120                 125

<210> SEQ ID NO 30
<211> LENGTH: 128
<212> TYPE: PRT
<213> ORGANISM: Artificial Sequence
<220> FEATURE:
<223> OTHER INFORMATION: CTLA4 ISVD-31

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Ile Gly Gly Gly Ser Thr Tyr Tyr Ala Asp Ser Val
        50                  55                  60
```

```
Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 31
<211> LENGTH: 128
<212> TYPE: PRT
<213> ORGANISM: Artificial Sequence
<220> FEATURE:
<223> OTHER INFORMATION: CTLA4 ISVD-32

<400> SEQUENCE: 31

Gln Val Gln Leu Val Glu Ser Gly Gly Gly Leu Val Gln Pro Gly Gly
1                   5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Glu Arg Glu Gly Val
            35                  40                  45

Ala Ala Ile Tyr Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 32
<211> LENGTH: 128
<212> TYPE: PRT
<213> ORGANISM: Artificial Sequence
<220> FEATURE:
<223> OTHER INFORMATION: CTLA4 ISVD-33

<400> SEQUENCE: 32

Gln Val Gln Leu Val Glu Ser Gly Gly Gly Leu Val Gln Pro Gly Gly
1                   5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Gly Leu Val Gly Val
            35                  40                  45

Ala Ala Ile Tyr Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
```

-continued

```
        115                 120                 125
```

```
<210> SEQ ID NO 33
<211> LENGTH: 3
<212> TYPE: PRT
<213> ORGANISM: Artificial Sequence
<220> FEATURE:
<223> OTHER INFORMATION: short linker

<400> SEQUENCE: 33

Gly Ala Pro
1

<210> SEQ ID NO 34
<211> LENGTH: 15
<212> TYPE: PRT
<213> ORGANISM: Artificial Sequence
<220> FEATURE:
<223> OTHER INFORMATION: long linker

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 232
<212> TYPE: PRT
<213> ORGANISM: Artificial Sequence
<220> FEATURE:
<223> OTHER INFORMATION: IgG1-Fc region with hinge

<400> SEQUENCE: 35

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

-continued

```
Ser Leu Ser Leu Ser Pro Gly Lys
225             230

<210> SEQ ID NO 36
<211> LENGTH: 330
<212> TYPE: PRT
<213> ORGANISM: Artificial Sequence
<220> FEATURE:
<223> OTHER INFORMATION: human IgG1 constant region

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
```

```
<211> LENGTH: 124
<212> TYPE: PRT
<213> ORGANISM: Artificial Sequence
<220> FEATURE:
<223> OTHER INFORMATION: control dAb

<400> SEQUENCE: 37

Gln Val Gln Leu Gln Glu Ser Gly Gly Gly Ser Val Gln Ala Gly Gly
1               5                   10                  15

Ser Leu Arg Leu Ser Cys Glu Ala Ser Gly Tyr Thr Tyr Cys Met Gly
            20                  25                  30

Trp Phe Arg Gln Ala Pro Gly Lys Glu Arg Glu Gly Val Ala Leu Ala
            35                  40                  45

Val Thr Gly Ile Ser Ile Pro Tyr Tyr Ala Asp Ser Val Lys Gly Arg
        50                  55                  60

Phe Thr Ile Ser Gln Asp Asn Val Lys Asn Thr Leu Tyr Leu Gln Met
65                  70                  75                  80

Asn Ser Leu Lys Pro Glu Asp Ala Ala Met Tyr Tyr Cys Ala Ala Ser
                85                  90                  95

Thr Ile Arg Tyr Val Cys Pro Gly Leu Asn Arg Gly Asp Gln Phe Lys
            100                 105                 110

Asn Trp Gly Gln Gly Thr Gln Val Thr Val Ser Ser
            115                 120

<210> SEQ ID NO 38
<211> LENGTH: 232
<212> TYPE: PRT
<213> ORGANISM: Artificial Sequence
<220> FEATURE:
<223> OTHER INFORMATION: IgG1-Fc region with hinge (C-S)

<400> SEQUENCE: 38

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
```

-continued

```
            195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 39
<211> LENGTH: 227
<212> TYPE: PRT
<213> ORGANISM: Artificial Sequence
<220> FEATURE:
<223> OTHER INFORMATION: human IgG1-Fc region without hinge

<400> SEQUENCE: 39

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 40
<211> LENGTH: 493
<212> TYPE: PRT
<213> ORGANISM: Artificial Sequence
<220> FEATURE:
<223> OTHER INFORMATION: aPDL1.9-aCTLA4.34-Fc

<400> SEQUENCE: 40

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30
```

-continued

```
Cys Met Ala Trp Phe Arg Gln Ala Pro Gly Lys Glu Arg Glu Arg Val
    35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

Gly Ala Pro Gln Val Gln Leu Val Glu Ser Gly Gly Gly Leu Val Gln
    130                 135                 140

Pro Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Gly Leu
                165                 170                 175

Glu Gly Val Ala Ala Ile Tyr Ile Gly Gly Gly Ser Thr Tyr Tyr Ala
            180                 185                 190

Asp Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
    210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Leu Val Thr
                245                 250                 255

Val Ser Ser Gly Ser Glu Pro Lys Ser Ser Asp Lys Thr His Thr Cys
            260                 265                 270

Pro Pro Cys Pro Ala Pro Glu Leu Leu Gly Gly Pro Ser Val Phe Leu
            275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
            435                 440                 445

Ser Phe Phe Leu Tyr Ser Lys Leu Thr Val Asp Lys Ser Arg Trp Gln
```

-continued

```
            450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 41
<211> LENGTH: 505
<212> TYPE: PRT
<213> ORGANISM: Artificial Sequence
<220> FEATURE:
<223> OTHER INFORMATION: aPDL1.9-L-aCTLA4.34-Fc

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Gly Gly Gly Gly Ser Gly Gly Gly Gly Ser Gly Gly Gly Gly Ser Gln
        130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Tyr Ile Tyr Ser Ala Tyr Cys
                165                 170                 175

Met Gly Trp Phe Arg Gln Ala Pro Gly Lys Gly Leu Glu Gly Val Ala
                180                 185                 190

Ala Ile Tyr Ile Gly Gly Gly Ser Thr Tyr Tyr Ala Asp Ser Val Lys
            195                 200                 205

Gly Arg Phe Thr Ile Ser Arg Asp Asn Ser Lys Asn Thr Leu Tyr Leu
        210                 215                 220

Gln Met Asn Ser Leu Arg Ala Glu Asp Thr Ala Val Tyr Tyr Cys Ala
225                 230                 235                 240

Ala Asp Val Ile Pro Thr Glu Thr Cys Leu Gly Gly Ser Trp Ser Gly
                245                 250                 255

Pro Phe Gly Tyr Trp Gly Gln Gly Thr Leu Val Thr Val Ser Ser Gly
                260                 265                 270

Ser Glu Pro Lys Ser Ser Asp Lys Thr His Thr Cys Pro Pro Cys Pro
            275                 280                 285

Ala Pro Glu Leu Leu Gly Gly Pro Ser Val Phe Leu Phe Pro Pro Lys
        290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
```

-continued

```
                325                 330                 335
Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
            355                 360                 365

Gln Asp Trp Leu Asn Gly Lys Glu Tyr Lys Cys Lys Val Ser Asn Lys
        370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
        450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505
```

```
<210> SEQ ID NO 42
<211> LENGTH: 493
<212> TYPE: PRT
<213> ORGANISM: Artificial Sequence
<220> FEATURE:
<223> OTHER INFORMATION: aCTLA4.34-aPDL1.9-Fc

<400> SEQUENCE: 42
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Tyr Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
            115                 120                 125

Gly Ala Pro Gln Val Gln Leu Val Glu Ser Gly Gly Gly Leu Val Gln
        130                 135                 140

Pro Gly Gly Ser Leu Arg Leu Ser Cys Ala Ala Ser Gly Lys Met Ser
145                 150                 155                 160

Ser Arg Arg Cys Met Ala Trp Phe Arg Gln Ala Pro Gly Lys Glu Arg
                165                 170                 175

Glu Arg Val Ala Lys Leu Leu Thr Thr Ser Gly Ser Thr Tyr Leu Ala
```

-continued

```
              180                 185                 190
Asp Ser Val Lys Gly Arg Phe Thr Ile Ser Arg Asp Asn Ser Lys Asn
          195                 200                 205

Thr Val Tyr Leu Gln Met Asn Ser Leu Arg Ala Glu Asp Thr Ala Val
      210                 215                 220

Tyr Tyr Cys Ala Ala Asp Ser Phe Glu Asp Pro Thr Cys Thr Leu Val
225                 230                 235                 240

Thr Ser Ser Gly Ala Phe Gln Tyr Trp Gly Gln Gly Thr Leu Val Thr
              245                 250                 255

Val Ser Ser Gly Ser Glu Pro Lys Ser Ser Asp Lys Thr His Thr Cys
          260                 265                 270

Pro Pro Cys Pro Ala Pro Glu Leu Leu Gly Gly Pro Ser Val Phe Leu
          275                 280                 285

Phe Pro Pro Lys Pro Lys Asp Thr Leu Met Ile Ser Arg Thr Pro Glu
      290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
              325                 330                 335

Pro Arg Glu Glu Gln Tyr Asn Ser Thr Tyr Arg Val Val Ser Val Leu
          340                 345                 350

Thr Val Leu His Gln Asp Trp Leu Asn Gly Lys Glu Tyr Lys Cys Lys
          355                 360                 365

Val Ser Asn Lys Ala Leu Pro Ala Pro Ile Glu Lys Thr Ile Ser Lys
      370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
              405                 410                 415

Gly Phe Tyr Pro Ser Asp Ile Ala Val Glu Trp Glu Ser Asn Gly Gln
              420                 425                 430

Pro Glu Asn Asn Tyr Lys Thr Thr Pro Pro Val Leu Asp Ser Asp Gly
          435                 440                 445

Ser Phe Phe Leu Tyr Ser Lys Leu Thr Val Asp Lys Ser Arg Trp Gln
      450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
              485                 490
```

```
<210> SEQ ID NO 43
<211> LENGTH: 505
<212> TYPE: PRT
<213> ORGANISM: Artificial Sequence
<220> FEATURE:
<223> OTHER INFORMATION: aCTLA4.34-L-aPDL1.9-Fc

<400> SEQUENCE: 43

Gln Val Gln Leu Val Glu Ser Gly Gly Gly Leu Val Gln Pro Gly Gly
1               5                 10                  15

Ser Leu Arg Leu Ser Cys Ala Ala Ser Gly Tyr Ile Tyr Ser Ala Tyr
          20                  25                  30

Cys Met Gly Trp Phe Arg Gln Ala Pro Gly Lys Gly Leu Glu Gly Val
          35                  40                  45

Ala Ala Ile Tyr Ile Gly Gly Gly Ser Thr Tyr Tyr Ala Asp Ser Val
```

-continued

```
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
            115                 120                 125

Gly Gly Gly Gly Ser Gly Gly Gly Ser Gly Gly Gly Gly Ser Gln
            130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Lys Met Ser Ser Arg Arg Cys
                165                 170                 175

Met Ala Trp Phe Arg Gln Ala Pro Gly Lys Glu Arg Glu Arg Val Ala
                180                 185                 190

Lys Leu Leu Thr Thr Ser Gly Ser Thr Tyr Leu Ala Asp Ser Val Lys
                195                 200                 205

Gly Arg Phe Thr Ile Ser Arg Asp Asn Ser Lys Asn Thr Val Tyr Leu
            210                 215                 220

Gln Met Asn Ser Leu Arg Ala Glu Asp Thr Ala Val Tyr Tyr Cys Ala
225                 230                 235                 240

Ala Asp Ser Phe Glu Asp Pro Thr Cys Thr Leu Val Thr Ser Ser Gly
                245                 250                 255

Ala Phe Gln Tyr Trp Gly Gln Gly Thr Leu Val Thr Val Ser Ser Gly
                260                 265                 270

Ser Glu Pro Lys Ser Ser Asp Lys Thr His Thr Cys Pro Pro Cys Pro
                275                 280                 285

Ala Pro Glu Leu Leu Gly Gly Pro Ser Val Phe Leu Phe Pro Pro Lys
                290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
                340                 345                 350

Gln Tyr Asn Ser Thr Tyr Arg Val Val Ser Val Leu Thr Val Leu His
                355                 360                 365

Gln Asp Trp Leu Asn Gly Lys Glu Tyr Lys Cys Lys Val Ser Asn Lys
                370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
                420                 425                 430

Ser Asp Ile Ala Val Glu Trp Glu Ser Asn Gly Gln Pro Glu Asn Asn
                435                 440                 445

Tyr Lys Thr Thr Pro Pro Val Leu Asp Ser Asp Gly Ser Phe Phe Leu
                450                 455                 460

Tyr Ser Lys Leu Thr Val Asp Lys Ser Arg Trp Gln Gln Gly Asn Val
465                 470                 475                 480
```

-continued

```
Phe Ser Cys Ser Val Met His Glu Ala Leu His Asn His Tyr Thr Gln
                485             490             495

Lys Ser Leu Ser Leu Ser Pro Gly Lys
        500             505

<210> SEQ ID NO 44
<211> LENGTH: 487
<212> TYPE: PRT
<213> ORGANISM: Artificial Sequence
<220> FEATURE:
<223> OTHER INFORMATION: aPDL1.9-dAb-Fc

<400> SEQUENCE: 44

Gln Val Gln Leu Val Glu Ser Gly Gly Gly Leu Val Gln Pro Gly Gly
1               5                   10              15

Ser Leu Arg Leu Ser Cys Ala Ala Ser Gly Lys Met Ser Ser Arg Arg
            20              25              30

Cys Met Ala Trp Phe Arg Gln Ala Pro Gly Lys Glu Arg Glu Arg Val
        35              40              45

Ala Lys Leu Leu Thr Thr Ser Gly Ser Thr Tyr Leu Ala Asp Ser Val
    50              55              60

Lys Gly Arg Phe Thr Ile Ser Arg Asp Asn Ser Lys Asn Thr Val Tyr
65              70              75              80

Leu Gln Met Asn Ser Leu Arg Ala Glu Asp Thr Ala Val Tyr Tyr Cys
                85              90              95

Ala Ala Asp Ser Phe Glu Asp Pro Thr Cys Thr Leu Val Thr Ser Ser
            100             105             110

Gly Ala Phe Gln Tyr Trp Gly Gln Gly Thr Leu Val Thr Val Ser Ser
        115             120             125

Gly Ala Pro Gln Val Gln Leu Gln Glu Ser Gly Gly Gly Ser Val Gln
    130             135             140

Ala Gly Gly Ser Leu Arg Leu Ser Cys Glu Ala Ser Gly Tyr Thr Tyr
145             150             155             160

Cys Met Gly Trp Phe Arg Gln Ala Pro Gly Lys Glu Arg Glu Gly Val
            165             170             175

Ala Leu Ala Val Thr Gly Ile Ser Ile Pro Tyr Tyr Ala Asp Ser Val
            180             185             190

Lys Gly Arg Phe Thr Ile Ser Gln Asp Asn Val Lys Asn Thr Leu Tyr
        195             200             205

Leu Gln Met Asn Ser Leu Lys Pro Glu Asp Ala Ala Met Tyr Tyr Cys
    210             215             220

Ala Ala Ser Thr Ile Arg Tyr Val Cys Pro Gly Leu Asn Arg Gly Asp
225             230             235             240

Gln Phe Lys Asn Trp Gly Gln Gly Thr Gln Val Thr Val Ser Ser Glu
            245             250             255

Pro Lys Ser Ser Asp Lys Thr His Thr Cys Pro Pro Cys Pro Ala Pro
        260             265             270

Glu Leu Leu Gly Gly Pro Ser Val Phe Leu Phe Pro Pro Lys Pro Lys
        275             280             285

Asp Thr Leu Met Ile Ser Arg Thr Pro Glu Val Thr Cys Val Val Val
    290             295             300

Asp Val Ser His Glu Asp Pro Glu Val Lys Phe Asn Trp Tyr Val Asp
305             310             315             320

Gly Val Glu Val His Asn Ala Lys Thr Lys Pro Arg Glu Glu Gln Tyr
            325             330             335
```

-continued

```
Asn Ser Thr Tyr Arg Val Val Ser Val Leu Thr Val Leu His Gln Asp
        340             345             350

Trp Leu Asn Gly Lys Glu Tyr Lys Cys Lys Val Ser Asn Lys Ala Leu
        355             360             365

Pro Ala Pro Ile Glu Lys Thr Ile Ser Lys Ala Lys Gly Gln Pro Arg
        370             375             380

Glu Pro Gln Val Tyr Thr Leu Pro Pro Ser Arg Asp Glu Leu Thr Lys
385             390             395             400

Asn Gln Val Ser Leu Thr Cys Leu Val Lys Gly Phe Tyr Pro Ser Asp
            405             410             415

Ile Ala Val Glu Trp Glu Ser Asn Gly Gln Pro Glu Asn Asn Tyr Lys
        420             425             430

Thr Thr Pro Pro Val Leu Asp Ser Asp Gly Ser Phe Phe Leu Tyr Ser
        435             440             445

Lys Leu Thr Val Asp Lys Ser Arg Trp Gln Gln Gly Asn Val Phe Ser
    450             455             460

Cys Ser Val Met His Glu Ala Leu His Asn His Tyr Thr Gln Lys Ser
465             470             475             480

Leu Ser Leu Ser Pro Gly Lys
            485
```

```
<210> SEQ ID NO 45
<211> LENGTH: 487
<212> TYPE: PRT
<213> ORGANISM: Artificial Sequence
<220> FEATURE:
<223> OTHER INFORMATION: dAb-aCTLA4.34-Fc

<400> SEQUENCE: 45

Gln Val Gln Leu Gln Glu Ser Gly Gly Gly Ser Val Gln Ala Gly Gly
1               5               10              15

Ser Leu Arg Leu Ser Cys Glu Ala Ser Gly Tyr Thr Tyr Cys Met Gly
        20              25              30

Trp Phe Arg Gln Ala Pro Gly Lys Glu Arg Glu Gly Val Ala Leu Ala
        35              40              45

Val Thr Gly Ile Ser Ile Pro Tyr Tyr Ala Asp Ser Val Lys Gly Arg
    50              55              60

Phe Thr Ile Ser Gln Asp Asn Val Lys Asn Thr Leu Tyr Leu Gln Met
65              70              75              80

Asn Ser Leu Lys Pro Glu Asp Ala Ala Met Tyr Tyr Cys Ala Ala Ser
            85              90              95

Thr Ile Arg Tyr Val Cys Pro Gly Leu Asn Arg Gly Asp Gln Phe Lys
            100             105             110

Asn Trp Gly Gln Gly Thr Gln Val Thr Val Ser Ser Gly Ala Pro Gln
            115             120             125

Val Gln Leu Val Glu Ser Gly Gly Gly Leu Val Gln Pro Gly Gly Ser
        130             135             140

Leu Arg Leu Ser Cys Ala Ala Ser Gly Tyr Ile Tyr Ser Ala Tyr Cys
145             150             155             160

Met Gly Trp Phe Arg Gln Ala Pro Gly Lys Gly Leu Glu Gly Val Ala
            165             170             175

Ala Ile Tyr Ile Gly Gly Gly Ser Thr Tyr Tyr Ala Asp Ser Val Lys
            180             185             190

Gly Arg Phe Thr Ile Ser Arg Asp Asn Ser Lys Asn Thr Leu Tyr Leu
        195             200             205
```

-continued

```
Gln Met Asn Ser Leu Arg Ala Glu Asp Thr Ala Val Tyr Tyr Cys Ala
    210                 215                 220
```

```
Ala Asp Val Ile Pro Thr Glu Thr Cys Leu Gly Gly Ser Trp Ser Gly
225                 230                 235                 240
```

```
Pro Phe Gly Tyr Trp Gly Gln Gly Thr Leu Val Thr Val Ser Ser Glu
                245                 250                 255
```

```
Pro Lys Ser Ser Asp Lys Thr His Thr Cys Pro Pro Cys Pro Ala Pro
                260                 265                 270
```

```
Glu Leu Leu Gly Gly Pro Ser Val Phe Leu Phe Pro Pro Lys Pro Lys
                275                 280                 285
```

```
Asp Thr Leu Met Ile Ser Arg Thr Pro Glu Val Thr Cys Val Val Val
    290                 295                 300
```

```
Asp Val Ser His Glu Asp Pro Glu Val Lys Phe Asn Trp Tyr Val Asp
305                 310                 315                 320
```

```
Gly Val Glu Val His Asn Ala Lys Thr Lys Pro Arg Glu Glu Gln Tyr
                325                 330                 335
```

```
Asn Ser Thr Tyr Arg Val Val Ser Val Leu Thr Val Leu His Gln Asp
                340                 345                 350
```

```
Trp Leu Asn Gly Lys Glu Tyr Lys Cys Lys Val Ser Asn Lys Ala Leu
                355                 360                 365
```

```
Pro Ala Pro Ile Glu Lys Thr Ile Ser Lys Ala Lys Gly Gln Pro Arg
    370                 375                 380
```

```
Glu Pro Gln Val Tyr Thr Leu Pro Pro Ser Arg Asp Glu Leu Thr Lys
385                 390                 395                 400
```

```
Asn Gln Val Ser Leu Thr Cys Leu Val Lys Gly Phe Tyr Pro Ser Asp
                405                 410                 415
```

```
Ile Ala Val Glu Trp Glu Ser Asn Gly Gln Pro Glu Asn Asn Tyr Lys
                420                 425                 430
```

```
Thr Thr Pro Pro Val Leu Asp Ser Asp Gly Ser Phe Phe Leu Tyr Ser
                435                 440                 445
```

```
Lys Leu Thr Val Asp Lys Ser Arg Trp Gln Gln Gly Asn Val Phe Ser
    450                 455                 460
```

```
Cys Ser Val Met His Glu Ala Leu His Asn His Tyr Thr Gln Lys Ser
465                 470                 475                 480
```

```
Leu Ser Leu Ser Pro Gly Lys
                485
```

```
<210> SEQ ID NO 46
<211> LENGTH: 491
<212> TYPE: PRT
<213> ORGANISM: Artificial Sequence
<220> FEATURE:
<223> OTHER INFORMATION: aPDL1.6-aCTLA4.34-Fc

<400> SEQUENCE: 46
```

```
Gln Val Gln Leu Gln Glu Ser Gly Gly Gly Ser Val Gln Ala Gly Gly
1               5                   10                  15
```

```
Ser Leu Arg Leu Ser Cys Ala Ala Ser Gly Asn Ile Ile Arg Val Arg
                20                  25                  30
```

```
Cys Met Ala Trp Phe Arg Gln Ala Pro Gly Lys Glu Arg Glu Arg Gly
            35                  40                  45
```

```
Pro Asn Ile Leu Thr Thr Thr Ile Ser Thr Tyr Leu Ala Asp Ser Val
    50                  55                  60
```

```
Lys Gly Arg Phe Thr Ile Ser Gln Asn Asn Ala Lys Ser Thr Val Tyr
65                  70                  75                  80
```

-continued

```
Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
               100                 105                 110

Gly Ala Phe Gln Tyr Trp Gly Gln Gly Thr Gln Val Thr Val Ser Ser
               115                 120                 125

Gly Ala Pro Gln Val Gln Leu Val Glu Ser Gly Gly Gly Leu Val Gln
           130                 135                 140

Pro Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Gly Leu
               165                 170                 175

Glu Gly Val Ala Ala Ile Tyr Ile Gly Gly Gly Ser Thr Tyr Tyr Ala
               180                 185                 190

Asp Ser Val Lys Gly Arg Phe Thr Ile Ser Arg Asp Asn Ser Lys Asn
           195                 200                 205

Thr Leu Tyr Leu Gln Met Asn Ser Leu Arg Ala Glu Asp Thr Ala Val
           210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Leu Val Thr
               245                 250                 255

Val Ser Ser Glu Pro Lys Ser Ser Asp Lys Thr His Thr Cys Pro Pro
               260                 265                 270

Cys Pro Ala Pro Glu Leu Leu Gly Gly Pro Ser Val Phe Leu Phe Pro
               275                 280                 285

Pro Lys Pro Lys Asp Thr Leu Met Ile Ser Arg Thr Pro Glu Val Thr
           290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
               325                 330                 335

Glu Glu Gln Tyr Asn Ser Thr Tyr Arg Val Val Ser Val Leu Thr Val
               340                 345                 350

Leu His Gln Asp Trp Leu Asn Gly Lys Glu Tyr Lys Cys Lys Val Ser
           355                 360                 365

Asn Lys Ala Leu Pro Ala Pro Ile Glu Lys Thr Ile Ser Lys Ala Lys
           370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
               405                 410                 415

Tyr Pro Ser Asp Ile Ala Val Glu Trp Glu Ser Asn Gly Gln Pro Glu
               420                 425                 430

Asn Asn Tyr Lys Thr Thr Pro Pro Val Leu Asp Ser Asp Gly Ser Phe
           435                 440                 445

Phe Leu Tyr Ser Lys Leu Thr Val Asp Lys Ser Arg Trp Gln Gln Gly
           450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys
               485                 490
```

```
<210> SEQ ID NO 47
<211> LENGTH: 487
<212> TYPE: PRT
<213> ORGANISM: Artificial Sequence
<220> FEATURE:
<223> OTHER INFORMATION: aPDL1.6-dAb-Fc

<400> SEQUENCE: 47

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
            20                  25                  30

Cys Met Ala Trp Phe Arg Gln Ala Pro Gly Lys Glu Arg Glu Arg Gly
        35                  40                  45

Pro Asn Ile Leu Thr Thr Thr Ile Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
            85                  90                  95

Ala Ala Asp Ser Phe Gly Tyr Pro Thr Cys Pro Gly Pro Ala Ser Ser
            100                 105                 110

Gly Ala Phe Gln Tyr Trp Gly Gln Gly Thr Gln Val Thr Val Ser Ser
            115                 120                 125

Gly Ala Pro Gln Val Gln Leu Gln Glu Ser Gly Gly Gly Ser Val Gln
    130                 135                 140

Ala Gly Gly Ser Leu Arg Leu Ser Cys Glu Ala Ser Gly Tyr Thr Tyr
145                 150                 155                 160

Cys Met Gly Trp Phe Arg Gln Ala Pro Gly Lys Glu Arg Glu Gly Val
            165                 170                 175

Ala Leu Ala Val Thr Gly Ile Ser Ile Pro Tyr Tyr Ala Asp Ser Val
            180                 185                 190

Lys Gly Arg Phe Thr Ile Ser Gln Asp Asn Val Lys Asn Thr Leu Tyr
            195                 200                 205

Leu Gln Met Asn Ser Leu Lys Pro Glu Asp Ala Ala Met Tyr Tyr Cys
    210                 215                 220

Ala Ala Ser Thr Ile Arg Tyr Val Cys Pro Gly Leu Asn Arg Gly Asp
225                 230                 235                 240

Gln Phe Lys Asn Trp Gly Gln Gly Thr Gln Val Thr Val Ser Ser Glu
            245                 250                 255

Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
            355                 360                 365
```

-continued

```
Pro Ala Pro Ile Glu Lys Thr Ile Ser Lys Ala Lys Gly Gln Pro Arg
    370             375             380

Glu Pro Gln Val Tyr Thr Leu Pro Pro Ser Arg Asp Glu Leu Thr Lys
385             390             395             400

Asn Gln Val Ser Leu Thr Cys Leu Val Lys Gly Phe Tyr Pro Ser Asp
                405             410             415

Ile Ala Val Glu Trp Glu Ser Asn Gly Gln Pro Glu Asn Asn Tyr Lys
            420             425             430

Thr Thr Pro Pro Val Leu Asp Ser Asp Gly Ser Phe Phe Leu Tyr Ser
            435             440             445

Lys Leu Thr Val Asp Lys Ser Arg Trp Gln Gln Gly Asn Val Phe Ser
    450             455             460

Cys Ser Val Met His Glu Ala Leu His Asn His Tyr Thr Gln Lys Ser
465             470             475             480

Leu Ser Leu Ser Pro Gly Lys
            485
```

<210> SEQ ID NO 48
<211> LENGTH: 491
<212> TYPE: PRT
<213> ORGANISM: Artificial Sequence
<220> FEATURE:
<223> OTHER INFORMATION: aPDL1.m3-aCTLA4.34-Fc

<400> SEQUENCE: 48

```
Gln Val Gln Leu Gln Glu Ser Gly Gly Gly Leu Val Gln Pro Gly Gly
1               5               10              15

Ser Leu Arg Leu Ser Cys Ala Ala Ser Gly Lys Met Ser Ser Arg Arg
            20              25              30

Cys Met Ala Trp Phe Arg Gln Ala Pro Gly Lys Glu Arg Glu Arg Val
        35              40              45

Ala Asp Val Asn Pro Asn Ser Gly Gly Ser Ile Tyr Asn Gln Arg Phe
    50              55              60

Lys Gly Arg Phe Thr Ile Ser Gln Asn Asn Ala Lys Ser Thr Val Tyr
65              70              75              80

Leu Gln Met Asn Ser Leu Lys Pro Glu Asp Thr Ala Met Tyr Tyr Cys
                85              90              95

Ala Ala Asp Ser Phe Glu Asp Pro Thr Cys Thr Leu Val Thr Ser Ser
            100             105             110

Gly Ala Phe Gln Tyr Trp Gly Gln Gly Thr Gln Val Thr Val Ser Ser
        115             120             125

Gly Ala Pro Gln Val Gln Leu Val Glu Ser Gly Gly Gly Leu Val Gln
    130             135             140

Pro Gly Gly Ser Leu Arg Leu Ser Cys Ala Ala Ser Gly Tyr Ile Tyr
145             150             155             160

Ser Ala Tyr Cys Met Gly Trp Phe Arg Gln Ala Pro Gly Lys Gly Leu
                165             170             175

Glu Gly Val Ala Ala Ile Tyr Ile Gly Gly Gly Ser Thr Tyr Tyr Ala
            180             185             190

Asp Ser Val Lys Gly Arg Phe Thr Ile Ser Arg Asp Asn Ser Lys Asn
            195             200             205

Thr Leu Tyr Leu Gln Met Asn Ser Leu Arg Ala Glu Asp Thr Ala Val
    210             215             220

Tyr Tyr Cys Ala Ala Asp Val Ile Pro Thr Glu Thr Cys Leu Gly Gly
225             230             235             240
```

-continued

```
Ser Trp Ser Gly Pro Phe Gly Tyr Trp Gly Gln Gly Thr Leu Val Thr
                245                 250                 255

Val Ser Ser Glu Pro Lys Ser Ser Asp Lys Thr His Thr Cys Pro Pro
            260                 265                 270

Cys Pro Ala Pro Glu Leu Leu Gly Gly Pro Ser Val Phe Leu Phe Pro
            275                 280                 285

Pro Lys Pro Lys Asp Thr Leu Met Ile Ser Arg Thr Pro Glu Val Thr
        290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
    370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
            405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
            435                 440                 445

Phe Leu Tyr Ser Lys Leu Thr Val Asp Lys Ser Arg Trp Gln Gln Gly
    450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys
            485                 490
```

```
<210> SEQ ID NO 49
<211> LENGTH: 487
<212> TYPE: PRT
<213> ORGANISM: Artificial Sequence
<220> FEATURE:
<223> OTHER INFORMATION: aPDL1.m3-dAb-Fc

<400> SEQUENCE: 49

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Asp Val Asn Pro Asn Ser Gly Gly Ser Ile Tyr Asn Gln Arg Phe
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110
```

-continued

```
Gly Ala Phe Gln Tyr Trp Gly Gln Gly Thr Gln Val Thr Val Ser Ser
        115                 120                 125

Gly Ala Pro Gln Val Gln Leu Gln Glu Ser Gly Gly Gly Ser Val Gln
    130                 135                 140

Ala Gly Gly Ser Leu Arg Leu Ser Cys Glu Ala Ser Gly Tyr Thr Tyr
145                 150                 155                 160

Cys Met Gly Trp Phe Arg Gln Ala Pro Gly Lys Glu Arg Glu Gly Val
                165                 170                 175

Ala Leu Ala Val Thr Gly Ile Ser Ile Pro Tyr Tyr Ala Asp Ser Val
                180                 185                 190

Lys Gly Arg Phe Thr Ile Ser Gln Asp Asn Val Lys Asn Thr Leu Tyr
                195                 200                 205

Leu Gln Met Asn Ser Leu Lys Pro Glu Asp Ala Ala Met Tyr Tyr Cys
    210                 215                 220

Ala Ala Ser Thr Ile Arg Tyr Val Cys Pro Gly Leu Asn Arg Gly Asp
225                 230                 235                 240

Gln Phe Lys Asn Trp Gly Gln Gly Thr Gln Val Thr Val Ser Ser Glu
                245                 250                 255

Pro Lys Ser Ser Asp Lys Thr His Thr Cys Pro Pro Cys Pro Ala Pro
                260                 265                 270

Glu Leu Leu Gly Gly Pro Ser Val Phe Leu Phe Pro Pro Lys Pro Lys
                275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
                340                 345                 350

Trp Leu Asn Gly Lys Glu Tyr Lys Cys Lys Val Ser Asn Lys Ala Leu
                355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Tyr Ser
                435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485
```

```
<210> SEQ ID NO 50
<211> LENGTH: 491
<212> TYPE: PRT
<213> ORGANISM: Artificial Sequence
<220> FEATURE:
<223> OTHER INFORMATION: aPDL1.9-aCTLA4.13-Fc
```

-continued

```
<400> SEQUENCE: 50

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

Gly Ala Pro Gln Val Gln Leu Gln Glu Ser Gly Gly Gly Ser Val Gln
    130                 135                 140

Ala Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Glu Arg
                165                 170                 175

Val Gly Val Ala Ala Ile Ser Ile Gly Gly Gly Ser Thr Tyr Tyr Ala
            180                 185                 190

Asp Ser Val Lys Gly Arg Phe Thr Ile Ser Gln Asp Asn Ala Lys Asn
            195                 200                 205

Thr Leu Tyr Leu Gln Met Asn Ser Leu Lys Pro Glu Asp Thr Ala Met
    210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Gln Val Thr
            245                 250                 255

Val Ser Ser Glu Pro Lys Ser Ser Asp Lys Thr His Thr Cys Pro Pro
            260                 265                 270

Cys Pro Ala Pro Glu Leu Leu Gly Gly Pro Ser Val Phe Leu Phe Pro
            275                 280                 285

Pro Lys Pro Lys Asp Thr Leu Met Ile Ser Arg Thr Pro Glu Val Thr
    290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
            325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
            355                 360                 365

Asn Lys Ala Leu Pro Ala Pro Ile Glu Lys Thr Ile Ser Lys Ala Lys
    370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
```

-continued

```
               405              410              415

Tyr Pro Ser Asp Ile Ala Val Glu Trp Glu Ser Asn Gly Gln Pro Glu
            420              425              430

Asn Asn Tyr Lys Thr Thr Pro Pro Val Leu Asp Ser Asp Gly Ser Phe
            435              440              445

Phe Leu Tyr Ser Lys Leu Thr Val Asp Lys Ser Arg Trp Gln Gln Gly
        450              455              460

Asn Val Phe Ser Cys Ser Val Met His Glu Ala Leu His Asn His Tyr
465              470              475              480

Thr Gln Lys Ser Leu Ser Leu Ser Pro Gly Lys
                485              490

<210> SEQ ID NO 51
<211> LENGTH: 487
<212> TYPE: PRT
<213> ORGANISM: Artificial Sequence
<220> FEATURE:
<223> OTHER INFORMATION: dAb-aCTLA4.13-Fc

<400> SEQUENCE: 51

Gln Val Gln Leu Gln Glu Ser Gly Gly Gly Ser Val Gln Ala Gly Gly
1               5               10               15

Ser Leu Arg Leu Ser Cys Glu Ala Ser Gly Tyr Thr Tyr Cys Met Gly
            20               25               30

Trp Phe Arg Gln Ala Pro Gly Lys Glu Arg Glu Gly Val Ala Leu Ala
            35               40               45

Val Thr Gly Ile Ser Ile Pro Tyr Tyr Ala Asp Ser Val Lys Gly Arg
        50               55               60

Phe Thr Ile Ser Gln Asp Asn Val Lys Asn Thr Leu Tyr Leu Gln Met
65               70               75               80

Asn Ser Leu Lys Pro Glu Asp Ala Ala Met Tyr Tyr Cys Ala Ala Ser
            85               90               95

Thr Ile Arg Tyr Val Cys Pro Gly Leu Asn Arg Gly Asp Gln Phe Lys
            100              105              110

Asn Trp Gly Gln Gly Thr Gln Val Thr Val Ser Ser Gly Ala Pro Gln
        115              120              125

Val Gln Leu Gln Glu Ser Gly Gly Gly Ser Val Gln Ala Gly Gly Ser
    130              135              140

Leu Arg Leu Ser Cys Ala Ala Ser Gly Tyr Ile Tyr Ser Ala Tyr Cys
145              150              155              160

Met Gly Trp Phe Arg Gln Ala Pro Gly Lys Glu Arg Val Gly Val Ala
            165              170              175

Ala Ile Ser Ile Gly Gly Gly Ser Thr Tyr Tyr Ala Asp Ser Val Lys
            180              185              190

Gly Arg Phe Thr Ile Ser Gln Asp Asn Ala Lys Asn Thr Leu Tyr Leu
        195              200              205

Gln Met Asn Ser Leu Lys Pro Glu Asp Thr Ala Met Tyr Tyr Cys Ala
    210              215              220

Ala Asp Val Ile Pro Thr Glu Thr Cys Leu Gly Gly Ser Trp Ser Gly
225              230              235              240

Pro Phe Gly Tyr Trp Gly Gln Gly Thr Gln Val Thr Val Ser Ser Glu
            245              250              255

Pro Lys Ser Ser Asp Lys Thr His Thr Cys Pro Pro Cys Pro Ala Pro
            260              265              270

Glu Leu Leu Gly Gly Pro Ser Val Phe Leu Phe Pro Pro Lys Pro Lys
```

-continued

```
                275                 280                 285
Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
                340                 345                 350

Trp Leu Asn Gly Lys Glu Tyr Lys Cys Lys Val Ser Asn Lys Ala Leu
                355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Tyr Ser
                435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 52
<211> LENGTH: 357
<212> TYPE: PRT
<213> ORGANISM: Artificial Sequence
<220> FEATURE:
<223> OTHER INFORMATION: CTLA4-muFc

<400> SEQUENCE: 52

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
                35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Gly Ser Met
                115                 120                 125

Asp Pro Lys Ser Ser Asp Lys Thr His Thr Cys Pro Pro Cys Pro Ala
    130                 135                 140

Pro Glu Val Ser Ser Val Phe Ile Phe Pro Pro Lys Pro Lys Asp Val
```

-continued

```
145                 150                 155                 160

Leu Thr Ile Thr Leu Thr Pro Lys Val Thr Cys Val Val Val Asp Ile
                165                 170                 175

Ser Lys Asp Asp Pro Glu Val Gln Phe Ser Trp Phe Val Asp Asp Val
            180                 185                 190

Glu Val His Thr Ala Gln Thr Gln Pro Arg Glu Glu Gln Phe Asn Ser
        195                 200                 205

Thr Phe Arg Ser Val Ser Glu Leu Pro Ile Met His Gln Asp Trp Leu
    210                 215                 220

Asn Gly Lys Glu Phe Lys Cys Arg Val Asn Ser Ala Ala Phe Pro Ala
225                 230                 235                 240

Pro Ile Glu Lys Thr Ile Ser Lys Thr Lys Gly Arg Pro Lys Ala Pro
                245                 250                 255

Gln Val Tyr Thr Ile Pro Pro Pro Lys Glu Gln Met Ala Lys Asp Lys
            260                 265                 270

Val Ser Leu Thr Cys Met Ile Thr Asp Phe Phe Pro Glu Asp Ile Thr
        275                 280                 285

Val Glu Trp Gln Trp Asn Gly Gln Pro Ala Glu Asn Tyr Lys Asn Thr
    290                 295                 300

Gln Pro Ile Met Asn Thr Asn Gly Ser Tyr Phe Val Tyr Ser Lys Leu
305                 310                 315                 320

Asn Val Gln Lys Ser Asn Trp Glu Ala Gly Asn Thr Phe Thr Cys Ser
                325                 330                 335

Val Leu His Glu Gly Leu His Asn His His Thr Glu Lys Ser Leu Ser
                340                 345                 350

His Ser Pro Gly Lys
                355

<210> SEQ ID NO 53
<211> LENGTH: 452
<212> TYPE: PRT
<213> ORGANISM: Artificial Sequence
<220> FEATURE:
<223> OTHER INFORMATION: PD-L1-muFc

<400> SEQUENCE: 53

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
                20                  25                  30

Ala Leu Ile Val Tyr Trp Glu Met Glu Asp Lys Asn Ile Ile Gln Phe
            35                  40                  45

Val His Gly Glu Glu Asp Leu Lys Val Gln His Ser Ser Tyr Arg Gln
        50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
            115                 120                 125

Thr Ser Glu His Glu Leu Thr Cys Gln Ala Glu Gly Tyr Pro Lys Ala
    130                 135                 140

Glu Val Ile Trp Thr Ser Ser Asp His Gln Val Leu Ser Gly Lys Thr
```

-continued

```
145              150              155              160

Thr Thr Thr Asn Ser Lys Arg Glu Glu Asn Leu Phe Asn Val Thr Ser
             165              170              175

Thr Leu Arg Ile Asn Thr Thr Thr Asn Glu Ile Phe Tyr Cys Thr Phe
             180              185              190

Arg Arg Leu Asp Pro Glu Glu Asn His Thr Ala Glu Leu Val Ile Pro
             195              200              205

Glu Leu Pro Leu Ala His Pro Pro Asn Glu Arg Thr Gly Ser Met Asp
             210              215              220

Pro Lys Ser Ser Asp Lys Thr His Thr Cys Pro Pro Cys Pro Ala Pro
225              230              235              240

Glu Val Ser Ser Val Phe Ile Phe Pro Pro Lys Pro Lys Asp Val Leu
             245              250              255

Thr Ile Thr Leu Thr Pro Lys Val Thr Cys Val Val Val Asp Ile Ser
             260              265              270

Lys Asp Asp Pro Glu Val Gln Phe Ser Trp Phe Val Asp Asp Val Glu
             275              280              285

Val His Thr Ala Gln Thr Gln Pro Arg Glu Glu Gln Phe Asn Ser Thr
             290              295              300

Phe Arg Ser Val Ser Glu Leu Pro Ile Met His Gln Asp Trp Leu Asn
305              310              315              320

Gly Lys Glu Phe Lys Cys Arg Val Asn Ser Ala Ala Phe Pro Ala Pro
             325              330              335

Ile Glu Lys Thr Ile Ser Lys Thr Lys Gly Arg Pro Lys Ala Pro Gln
             340              345              350

Val Tyr Thr Ile Pro Pro Pro Lys Glu Gln Met Ala Lys Asp Lys Val
             355              360              365

Ser Leu Thr Cys Met Ile Thr Asp Phe Phe Pro Glu Asp Ile Thr Val
             370              375              380

Glu Trp Gln Trp Asn Gly Gln Pro Ala Glu Asn Tyr Lys Asn Thr Gln
385              390              395              400

Pro Ile Met Asn Thr Asn Gly Ser Tyr Phe Val Tyr Ser Lys Leu Asn
             405              410              415

Val Gln Lys Ser Asn Trp Glu Ala Gly Asn Thr Phe Thr Cys Ser Val
             420              425              430

Leu His Glu Gly Leu His Asn His His Thr Glu Lys Ser Leu Ser His
             435              440              445

Ser Pro Gly Lys
    450

<210> SEQ ID NO 54
<211> LENGTH: 448
<212> TYPE: PRT
<213> ORGANISM: Artificial Sequence
<220> FEATURE:
<223> OTHER INFORMATION: PD-L1-huFc

<400> SEQUENCE: 54

Thr Val Thr Val Pro Lys Asp Leu Tyr Val Val Glu Tyr Gly Ser Asn
1                5               10              15

Met Thr Ile Glu Cys Lys Phe Pro Val Glu Lys Gln Leu Asp Leu Ala
             20              25              30

Ala Leu Ile Val Tyr Trp Glu Met Glu Asp Lys Asn Ile Ile Gln Phe
             35              40              45

Val His Gly Glu Glu Asp Leu Lys Val Gln His Ser Ser Tyr Arg Gln
```

-continued

```
          50                    55                    60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
                100                 105                 110

Ala Pro Tyr Asn Lys Ile Asn Gln Arg Ile Leu Val Val Asp Pro Val
                115                 120                 125

Thr Ser Glu His Glu Leu Thr Cys Gln Ala Glu Gly Tyr Pro Lys Ala
                130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Thr Asn Glu Ile Phe Tyr Cys Thr Phe
                180                 185                 190

Arg Arg Leu Asp Pro Glu Glu Asn His Thr Ala Glu Leu Val Ile Pro
                195                 200                 205

Glu Leu Pro Leu Ala His Pro Pro Asn Glu Arg Thr Asp Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 55
<211> LENGTH: 442
<212> TYPE: PRT
<213> ORGANISM: Artificial Sequence -continued

```
<220> FEATURE:
<223> OTHER INFORMATION: CD80-muFc

<400> SEQUENCE: 55

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
            195                 200                 205

Ile Glu Gly Arg Met Asp Pro Lys Ser Ser Asp Lys Thr His Thr Cys
    210                 215                 220

Pro Pro Cys Pro Ala Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
            245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
            275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
            325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asn Thr Asn Gly Ser Tyr Phe
385                 390                 395                 400
```

-continued

```
Val Tyr Ser Lys Leu Asn Val Gln Lys Ser Asn Trp Glu Ala Gly Asn
            405                 410                 415

Thr Phe Thr Cys Ser Val Leu His Glu Gly Leu His Asn His His Thr
            420                 425                 430

Glu Lys Ser Leu Ser His Ser Pro Gly Lys
            435                 440

<210> SEQ ID NO 56
<211> LENGTH: 357
<212> TYPE: PRT
<213> ORGANISM: Artificial Sequence
<220> FEATURE:
<223> OTHER INFORMATION: CTLA4-huFc

<400> SEQUENCE: 56

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
            85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Cys Pro Pro Cys Pro Ala Pro Glu Leu
            130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320
```

-continued

```
Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 57
<211> LENGTH: 449
<212> TYPE: PRT
<213> ORGANISM: Artificial Sequence
<220> FEATURE:
<223> OTHER INFORMATION: CD86-muFc

<400> SEQUENCE: 57

Tyr Phe Asn Glu Thr Ala Asp Leu Pro Cys Gln Phe Ala Asn Ser Gln
1               5                   10                  15

Asn Gln Ser Leu Ser Glu Leu Val Val Phe Trp Gln Asp Gln Glu Asn
            20                  25                  30

Leu Val Leu Asn Glu Val Tyr Leu Gly Lys Glu Lys Phe Asp Ser Val
        35                  40                  45

His Ser Lys Tyr Met Gly Arg Thr Ser Phe Asp Ser Asp Ser Trp Thr
    50                  55                  60

Leu Arg Leu His Asn Leu Gln Ile Lys Asp Lys Gly Leu Tyr Gln Cys
65                  70                  75                  80

Ile Ile His His Lys Lys Pro Thr Gly Met Ile Arg Ile His Gln Met
                85                  90                  95

Asn Ser Glu Leu Ser Val Leu Ala Asn Phe Ser Gln Pro Glu Ile Val
            100                 105                 110

Pro Ile Ser Asn Ile Thr Glu Asn Val Tyr Ile Asn Leu Thr Cys Ser
        115                 120                 125

Ser Ile His Gly Tyr Pro Glu Pro Lys Lys Met Ser Val Leu Leu Arg
    130                 135                 140

Thr Lys Asn Ser Thr Ile Glu Tyr Asp Gly Ile Met Gln Lys Ser Gln
145                 150                 155                 160

Asp Asn Val Thr Glu Leu Tyr Asp Val Ser Ile Ser Leu Ser Val Ser
            165                 170                 175

Phe Pro Asp Val Thr Ser Asn Met Thr Ile Phe Cys Ile Leu Glu Thr
            180                 185                 190

Asp Lys Thr Arg Leu Leu Ser Ser Pro Phe Ser Ile Glu Leu Glu Asp
        195                 200                 205

Pro Gln Pro Pro Asp His Ile Pro Gly Ser Met Asp Pro Lys Ser
    210                 215                 220

Ser Asp Lys Thr His Thr Cys Pro Pro Cys Pro Ala Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320
```

-continued

```
Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
                340                 345                 350

Ile Pro Pro Pro Lys Glu Gln Met Ala Lys Asp Lys Val Ser Leu Thr
                355                 360                 365

Cys Met Ile Thr Asp Phe Phe Pro Glu Asp Ile Thr Val Glu Trp Gln
        370                 375                 380

Trp Asn Gly Gln Pro Ala Glu Asn Tyr Lys Asn Thr Gln Pro Ile Met
385                 390                 395                 400

Asn Thr Asn Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
                420                 425                 430

Gly Leu His Asn His His Thr Glu Lys Ser Leu Ser His Ser Pro Gly
        435                 440                 445

Lys

<210> SEQ ID NO 58
<211> LENGTH: 381
<212> TYPE: PRT
<213> ORGANISM: Artificial Sequence
<220> FEATURE:
<223> OTHER INFORMATION: PD1-muFc

<400> SEQUENCE: 58

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
                35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
        130                 135                 140

Gln Phe Gln Ile Glu Gly Arg Met Asp Pro Lys Ser Ser Asp Lys Thr
145                 150                 155                 160

His Thr Cys Pro Pro Cys Pro Ala Pro Glu Val Ser Ser Val Phe Ile
                165                 170                 175

Phe Pro Pro Lys Pro Lys Asp Val Leu Thr Ile Thr Leu Thr Pro Lys
                180                 185                 190

Val Thr Cys Val Val Val Asp Ile Ser Lys Asp Asp Pro Glu Val Gln
        195                 200                 205

Phe Ser Trp Phe Val Asp Asp Val Glu Val His Thr Ala Gln Thr Gln
        210                 215                 220
```

-continued

```
Pro Arg Glu Glu Gln Phe Asn Ser Thr Phe Arg Ser Val Ser Glu Leu
225                 230                 235                 240

Pro Ile Met His Gln Asp Trp Leu Asn Gly Lys Glu Phe Lys Cys Arg
                245                 250                 255

Val Asn Ser Ala Ala Phe Pro Ala Pro Ile Glu Lys Thr Ile Ser Lys
                260                 265                 270

Thr Lys Gly Arg Pro Lys Ala Pro Gln Val Tyr Thr Ile Pro Pro Pro
                275                 280                 285

Lys Glu Gln Met Ala Lys Asp Lys Val Ser Leu Thr Cys Met Ile Thr
                290                 295                 300

Asp Phe Phe Pro Glu Asp Ile Thr Val Glu Trp Gln Trp Asn Gly Gln
305                 310                 315                 320

Pro Ala Glu Asn Tyr Lys Asn Thr Gln Pro Ile Met Asn Thr Asn Gly
                325                 330                 335

Ser Tyr Phe Val Tyr Ser Lys Leu Asn Val Gln Lys Ser Asn Trp Glu
                340                 345                 350

Ala Gly Asn Thr Phe Thr Cys Ser Val Leu His Glu Gly Leu His Asn
                355                 360                 365

His His Thr Glu Lys Ser Leu Ser His Ser Pro Gly Lys
    370                 375                 380

<210> SEQ ID NO 59
<211> LENGTH: 448
<212> TYPE: PRT
<213> ORGANISM: Artificial Sequence
<220> FEATURE:
<223> OTHER INFORMATION: Ipilimumab HC

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
                35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205
```

-continued

```
Asn Thr Lys Val Asp Lys Lys Val Glu Pro Lys Ser Cys Asp Lys Thr
    210             215                 220

His Thr Cys Pro Pro Cys Pro Ala Pro Glu Leu Leu Gly Gly Pro Ser
225             230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305             310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
    435                 440                 445
```

```
<210> SEQ ID NO 60
<211> LENGTH: 215
<212> TYPE: PRT
<213> ORGANISM: Artificial Sequence
<220> FEATURE:
<223> OTHER INFORMATION: Ipilimumab LC

<400> SEQUENCE: 60

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

-continued

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 61
<211> LENGTH: 451
<212> TYPE: PRT
<213> ORGANISM: Artificial Sequence
<220> FEATURE:
<223> OTHER INFORMATION: Durvalumab HC

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

-continued

```
Glu Asp Pro Glu Val Lys Phe Asn Trp Tyr Val Asp Gly Val Glu Val
    275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Pro Ala Pro Ile
                325             330             335

Glu Lys Thr Ile Ser Lys Ala Lys Gly Gln Pro Arg Glu Pro Gln Val
                340             345             350

Tyr Thr Leu Pro Pro Ser Arg Asp Glu Leu Thr Lys Asn Gln Val Ser
            355             360             365

Leu Thr Cys Leu Val Lys Gly Phe Tyr Pro Ser Asp Ile Ala Val Glu
    370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
                405             410             415

Asp Lys Ser Arg Trp Gln Gln Gly Asn Val Phe Ser Cys Ser Val Met
                420             425             430

His Glu Ala Leu His Asn His Tyr Thr Gln Lys Ser Leu Ser Leu Ser
            435             440             445

Pro Gly Lys
    450

<210> SEQ ID NO 62
<211> LENGTH: 215
<212> TYPE: PRT
<213> ORGANISM: Artificial Sequence
<220> FEATURE:
<223> OTHER INFORMATION: Durvalumab LC

<400> SEQUENCE: 62

Glu Ile Val Leu Thr Gln Ser Pro Gly Thr Leu Ser Leu Ser Pro Gly
1               5               10              15

Glu Arg Ala Thr Leu Ser Cys Arg Ala Ser Gln Arg Val Ser Ser Ser
                20              25              30

Tyr Leu Ala Trp Tyr Gln Gln Lys Pro Gly Gln Ala Pro Arg Leu Leu
            35              40              45

Ile Tyr Asp Ala Ser Ser Arg Ala Thr Gly Ile Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Gly Ser Leu Pro
                85              90              95

Trp Thr Phe Gly Gln Gly Thr Lys Val Glu Ile Lys Arg Thr Val Ala
            100             105             110

Ala Pro Ser Val Phe Ile Phe Pro Pro Ser Asp Glu Gln Leu Lys Ser
        115             120             125

Gly Thr Ala Ser Val Val Cys Leu Leu Asn Asn Phe Tyr Pro Arg Glu
    130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
            165             170             175
```

-continued

```
Ser Ser Thr Leu Thr Leu Ser Lys Ala Asp Tyr Glu Lys His Lys Val
        180             185             190

Tyr Ala Cys Glu Val Thr His Gln Gly Leu Ser Ser Pro Val Thr Lys
        195             200             205

Ser Phe Asn Arg Gly Glu Cys
    210             215

<210> SEQ ID NO 63
<211> LENGTH: 220
<212> TYPE: PRT
<213> ORGANISM: Artificial Sequence
<220> FEATURE:
<223> OTHER INFORMATION: human PD-L1 extracellular domain

<400> SEQUENCE: 63

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
        20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125

Thr Ser Glu His Glu Leu Thr Cys Gln Ala Glu Gly Tyr Pro Lys Ala
    130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Thr Asn Glu Ile Phe Tyr Cys Thr Phe
            180                 185                 190

Arg Arg Leu Asp Pro Glu Glu Asn His Thr Ala Glu Leu Val Ile Pro
        195                 200                 205

Glu Leu Pro Leu Ala His Pro Pro Asn Glu Arg Thr
    210                 215                 220

<210> SEQ ID NO 64
<211> LENGTH: 127
<212> TYPE: PRT
<213> ORGANISM: Artificial Sequence
<220> FEATURE:
<223> OTHER INFORMATION: N-terminal IgV domain of human PD-L1

<400> SEQUENCE: 64

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45
```

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr
            115                 120                 125

<210> SEQ ID NO 65
<211> LENGTH: 214
<212> TYPE: PRT
<213> ORGANISM: Artificial Sequence
<220> FEATURE:
<223> OTHER INFORMATION: Synthetic peptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 66
<211> LENGTH: 214
<212> TYPE: PRT
<213> ORGANISM: Artificial Sequence
<220> FEATURE:
<223> OTHER INFORMATION: Synthetic peptide

<400> SEQUENCE: 66

Asp Ile Gln Met Thr Gln Ser Pro Ser Ser Leu Ser Ala Ser Val Gly

-continued

```
1               5                   10                  15

Asp Arg Val Thr Ile Thr Cys Arg Ala Ser Gln Asp Val Asn Ile Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 67
<211> LENGTH: 214
<212> TYPE: PRT
<213> ORGANISM: Artificial Sequence
<220> FEATURE:
<223> OTHER INFORMATION: Synthetic peptide

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Tyr Pro Pro
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

-continued

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 68
<211> LENGTH: 214
<212> TYPE: PRT
<213> ORGANISM: Artificial Sequence
<220> FEATURE:
<223> OTHER INFORMATION: Synthetic peptide

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ile Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Tyr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 69
<211> LENGTH: 214
<212> TYPE: PRT
<213> ORGANISM: Artificial Sequence
<220> FEATURE:
<223> OTHER INFORMATION: Synthetic peptide

<400> SEQUENCE: 69

```
Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 70
<211> LENGTH: 214
<212> TYPE: PRT
<213> ORGANISM: Artificial Sequence
<220> FEATURE:
<223> OTHER INFORMATION: Synthetic peptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 71
gacatccaga tgacccagag ccccagcagc ctgagcgcca gcgtgggcga ccgcgtgacc        60
atcacctgcc gcgccagcca ggacgtgaac actgccgttg catggtacca gcagaagccc       120
ggcaaggccc ccaagctgct gatctacagc gccagcttcc tgtacagcgg cgtgcccagc       180
cgcttcagcg gcagccgcag cggcaccgac ttcaccctga ccatcagcag cctgcagccc       240
gaggacttcg ccacctacta ctgccagcag cactatacta ctcctccaac attcggccag       300
ggcaccaagg tggagatcaa gcgcaccgtg gccgccccca gcgtgttcat cttcccccccc     360 agcgacgagc agctcaagag cggcaccgcc agcgtggtgt gcctgctgaa caacttctac       420
ccccgcgagg ccaaggtgca gtggaaggtg gacaacgccc tgcagagcgg caacagccag       480
gagagcgtga ccgagcagga cagcaaggac agcacctaca gcctgagcag caccctgacc       540
ctgagcaagg ccgactacga gaagcacaag gtgtacgcct gcgaggtgac ccaccagggc       600
ctgagcagcc ccgtgaccaa gagcttcaac cgcggcgagt gc                          642

<210> SEQ ID NO 72
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 72
gacatccaga tgacccagag ccccagcagc ctgagcgcca gcgtgggcga ccgcgtgacc        60
atcacctgcc gcgccagcca ggacgtgaac attgccgttg catggtacca gcagaagccc       120
ggcaaggccc ccaagctgct gatctacagc gccagcttcc tgtacagcgg cgtgcccagc       180
cgcttcagcg gcagccgcag cggcaccgac ttcaccctga ccatcagcag cctgcagccc       240
gaggacttcg ccacctacta ctgccagcag cactatacta ctcctccaac attcggccag       300
ggcaccaagg tggagatcaa gcgcaccgtg gccgccccca gcgtgttcat cttcccccccc     360 agcgacgagc agctcaagag cggcaccgcc agcgtggtgt gcctgctgaa caacttctac       420
ccccgcgagg ccaaggtgca gtggaaggtg gacaacgccc tgcagagcgg caacagccag       480
gagagcgtga ccgagcagga cagcaaggac agcacctaca gcctgagcag caccctgacc       540
ctgagcaagg ccgactacga gaagcacaag gtgtacgcct gcgaggtgac ccaccagggc       600
ctgagcagcc ccgtgaccaa gagcttcaac cgcggcgagt gc                          642

<210> SEQ ID NO 73
<211> LENGTH: 642
```

<212> TYPE: DNA
<213> ORGANISM: Artificial Sequence
<220> FEATURE:
<223> OTHER INFORMATION: Synthetic oligonucleotide

<400> SEQUENCE: 73

```
gacatccaga tgacccagag ccccagcagc ctgagcgcca gcgtgggcga ccgcgtgacc        60
atcacctgcc gcgccagcca ggacgtgaac actgccgttg catggtacca gcagaagccc       120
ggcaaggccc ccaagctgct gatctacagc gccagcttcc tgtacagcgg cgtgcccagc       180
cgcttcagcg gcagccgcag cggcaccgac ttcaccctga ccatcagcag cctgcagccc       240
gaggacttcg ccacctacta ctgccagcag cactatactt atcctccaac attcggccag       300
ggcaccaagg tggagatcaa gcgcaccgtg gccgcccca gcgtgttcat cttccccccc        360
agcgacgagc agctcaagag cggcaccgcc agcgtggtgt gcctgctgaa caacttctac       420
ccccgcgagg ccaaggtgca gtggaaggtg dacaacgccc tgcagagcgg caacagccag       480
gagagcgtga ccgagcagga cagcaaggac agcacctaca gcctgagcag caccctgacc       540
ctgagcaagg ccgactacga gaagcacaag gtgtacgcct gcgaggtgac ccaccagggc       600
ctgagcagcc ccgtgaccaa gagcttcaac cgcggcgagt gc                          642
```

<210> SEQ ID NO 74
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 74

```
gacatccaga tgacccagag ccccagcagc ctgagcgcca gcgtgggcga ccgcgtgacc        60
atcacctgcc gcgccagcca ggacgtgaac attgccgttg catggtacca gcagaagccc       120
ggcaaggccc ccaagctgct gatctacagc gccagcttcc tgtacagcgg cgtgcccagc       180
cgcttcagcg gcagccgcag cggcaccgac ttcaccctga ccatcagcag cctgcagccc       240
gaggacttcg ccacctacta ctgccagcag cactatactt atcctccaac attcggccag       300
ggcaccaagg tggagatcaa gcgcaccgtg gccgccccca gcgtgttcat cttccccccc       360
agcgacgagc agctcaagag cggcaccgcc agcgtggtgt gcctgctgaa caacttctac       420
ccccgcgagg ccaaggtgca gtggaaggtg dacaacgccc tgcagagcgg caacagccag       480
gagagcgtga ccgagcagga cagcaaggac agcacctaca gcctgagcag caccctgacc       540
ctgagcaagg ccgactacga gaagcacaag gtgtacgcct gcgaggtgac ccaccagggc       600
ctgagcagcc ccgtgaccaa gagcttcaac cgcggcgagt gc                          642
```

<210> SEQ ID NO 75
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 75

```
gacatccaga tgacccagag ccccagcagc ctgagcgcca gcgtgggcga ccgcgtgacc        60
atcacctgca aggccagcca ggacgtgagc atcggcgtgg cctggtacca gcagaagccc       120
ggcaaggccc ccaagctgct gatctacagc gccagctacc gctacaccgg cgtgcccagc       180
cgcttcagcg gcagcggcag cggcaccgac ttcaccctga ccatcagcag cctgcagccc       240
```

-continued

```
gaggacttcg ccacctacta ctgccagcag tactacatct acccctacac cttcggccag      300
ggcaccaagg tggagatcaa gcgcaccgtg gccgccccca gcgtgttcat cttccccccc      360
agcgacgagc agctcaagag cggcaccgcc agcgtggtgt gcctgctgaa caacttctac      420
ccccgcgagg ccaaggtgca gtggaaggtg acaacgccc tgcagagcgg caacagccag       480
gagagcgtga ccgagcagga cagcaaggac agcacctaca gcctgagcag caccctgacc      540
ctgagcaagg ccgactacga gaagcacaag gtgtacgcct gcgaggtgac ccaccagggc      600
ctgagcagcc ccgtgaccaa gagcttcaac cgcggcgagt gc                         642
```

```
<210> SEQ ID NO 76
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 76
```

```
gacatccaga tgacccagag ccccagcagc ctgagcgcca gcgtgggcga ccgcgtgacc       60
atcacctgca aggccagcca ggacgtgagc atcggcgtgg cctggtacca gcagaagccc      120
ggcaaggccc ccaagctgct gatctacagc gccagctacc gctacaccgg cgtgcccagc      180
cgcttcagcg gcagcggcag cggcaccgac ttcaccctga ccatcagcag cctgcagccc      240
gaggacttcg ccacctacta ctgccagcag tactacatca cccctacac cttcggccag       300 ggcaccaagg tggagatcaa gcgcaccgtg gccgccccca gcgtgttcat cttcccccc       360 agcgacgagc agctcaagag cggcaccgcc agcgtggtgt gcctgctgaa caacttctac      420
ccccgcgagg ccaaggtgca gtggaaggtg acaacgccc tgcagagcgg caacagccag       480
gagagcgtga ccgagcagga cagcaaggac agcacctaca gcctgagcag caccctgacc      540
ctgagcaagg ccgactacga gaagcacaag gtgtacgcct gcgaggtgac ccaccagggc      600
ctgagcagcc ccgtgaccaa gagcttcaac cgcggcgagt gc                         642
```

```
<210> SEQ ID NO 77
<211> LENGTH: 630
<212> TYPE: PRT
<213> ORGANISM: Artificial Sequence
<220> FEATURE:
<223> OTHER INFORMATION: Synthetic peptide

<400> SEQUENCE: 77
```

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125
```

-continued

```
Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
                180                 185                 190

Leu Thr Arg Thr Val Cys Ala Gly Gly Cys Ala Arg Cys Lys Gly Pro
                195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

Cys Val Thr Ala Cys Pro Tyr Asn Tyr Leu Ser Thr Asp Val Gly Ala
                275                 280                 285

Cys Thr Leu Val Cys Pro Leu Ala Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
                340                 345                 350

Ala Phe Leu Pro Glu Ser Phe Asp Gly Asp Pro Ala Ser Asn Thr Ala
                355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
                420                 425                 430

Leu Arg Ser Leu Arg Glu Leu Gly Ser Gly Leu Ala Leu Ile His His
                435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
                500                 505                 510

Leu Arg Gly Gln Glu Cys Val Glu Glu Cys Arg Val Leu Gln Gly Leu
                515                 520                 525

Pro Arg Glu Tyr Val Asn Ala Arg His Cys Leu Pro Cys His Pro Glu
    530                 535                 540
```

-continued

___

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
                580                 585                 590

Lys Phe Pro Asp Glu Glu Gly Ala Cys Gln Pro Cys Pro Ile Asn Cys
                595                 600                 605

Thr His Ser Cys Val Asp Leu Asp Asp Lys Gly Cys Pro Ala Glu Gln
                610                 615                 620

Arg Ala Ser Pro Leu Thr
625                 630

<210> SEQ ID NO 78
<211> LENGTH: 630
<212> TYPE: PRT
<213> ORGANISM: Artificial Sequence
<220> FEATURE:
<223> OTHER INFORMATION: Synthetic peptide

<400> SEQUENCE: 78

Thr Gln Val Cys Thr Gly Thr Asp Met Lys Leu Arg Leu Pro Ala Ser
1                   5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
                35                  40                  45

Leu Ser Phe Leu Gln Asp Ile Gln Glu Val Gln Gly Tyr Val Leu Ile
                50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
                100                 105                 110

Gly Gly Leu Arg Glu Leu Gln Leu Arg Ser Leu Thr Glu Ile Leu Lys
                115                 120                 125

Gly Gly Val Leu Ile Gln Arg Asn Pro Gln Leu Cys Tyr Gln Asp Thr
                130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
                180                 185                 190

Leu Thr Arg Thr Val Cys Ala Gly Gly Cys Ala Arg Cys Lys Gly Pro
                195                 200                 205

Leu Pro Thr Asp Cys Cys His Glu Gln Cys Ala Ala Gly Cys Thr Gly
                210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

-continued

```
Cys Val Thr Ala Cys Pro Tyr Asn Tyr Leu Ser Thr Asp Val Gly Ser
        275             280             285

Cys Thr Leu Val Cys Pro Leu His Asn Gln Glu Val Thr Ala Glu Asp
        290             295             300

Gly Thr Gln Arg Cys Glu Lys Cys Ser Lys Pro Cys Ala Arg Val Cys
305             310             315             320

Tyr Gly Leu Gly Met Glu His Leu Arg Glu Val Arg Ala Val Thr Ser
            325             330             335

Ala Asn Ile Gln Glu Phe Ala Gly Cys Lys Lys Ile Phe Gly Ser Leu
            340             345             350

Ala Phe Leu Pro Glu Ser Phe Asp Gly Asp Pro Ala Ser Asn Thr Ala
        355             360             365

Pro Leu Gln Pro Glu Gln Leu Gln Val Phe Glu Thr Leu Glu Glu Ile
    370             375             380

Thr Gly Tyr Leu Tyr Ile Ser Ala Trp Pro Asp Ser Leu Pro Asp Leu
385             390             395             400

Ser Val Phe Gln Asn Leu Gln Val Ile Arg Gly Arg Ile Leu His Asn
            405             410             415

Gly Ala Tyr Ser Leu Thr Leu Gln Gly Leu Gly Ile Ser Trp Leu Gly
            420             425             430

Leu Arg Ser Leu Arg Glu Leu Gly Ser Gly Leu Ala Leu Ile His His
        435             440             445

Asn Thr His Leu Cys Phe Val His Thr Val Pro Trp Asp Gln Leu Phe
    450             455             460

Arg Asn Pro His Gln Ala Leu Leu His Thr Ala Asn Arg Pro Glu Asp
465             470             475             480

Glu Cys Val Gly Glu Gly Leu Ala Cys His Gln Leu Cys Ala Arg Gly
            485             490             495

His Cys Trp Gly Pro Gly Pro Thr Gln Cys Val Asn Cys Ser Gln Phe
            500             505             510

Leu Arg Gly Gln Glu Cys Val Glu Glu Cys Arg Val Leu Gln Gly Leu
        515             520             525

Pro Arg Glu Tyr Val Asn Ala Arg His Cys Leu Pro Cys His Pro Glu
    530             535             540

Cys Gln Pro Gln Asn Gly Ser Val Thr Cys Phe Gly Pro Ala Ala Asp
545             550             555             560

Gln Cys Val Ala Cys Ala His Tyr Lys Asp Pro Ala Phe Cys Val Ala
            565             570             575

Arg Cys Pro Ser Gly Val Lys Pro Asp Leu Ser Tyr Met Pro Ile Trp
            580             585             590

Lys Phe Pro Asp Glu Glu Gly Ala Cys Gln Pro Cys Pro Ile Asn Cys
        595             600             605

Thr His Ser Cys Val Asp Leu Asp Asp Lys Gly Cys Pro Ala Glu Gln
    610             615             620

Arg Ala Ser Pro Leu Thr
625             630
```

<210> SEQ ID NO 79
<211> LENGTH: 630
<212> TYPE: PRT
<213> ORGANISM: Artificial Sequence
<220> FEATURE:
<223> OTHER INFORMATION: Synthetic peptide
<400> SEQUENCE: 79

-continued

```
Thr Gln Val Cys Thr Gly Thr Asp Met Lys Leu Arg Leu Pro Ala Ser
1               5                  10                 15

Pro Glu Thr His Leu Asp Met Leu Arg His Leu Tyr Gln Gly Cys Gln
            20                 25                 30

Val Val Gln Gly Asn Leu Glu Leu Thr Tyr Leu Pro Thr Asn Ala Ser
        35                 40                 45

Leu Ser Phe Leu Gln Asp Ile Gln Glu Val Gln Gly Tyr Val Leu Ile
    50                 55                 60

Ala His Asn Gln Val Arg Gln Val Pro Leu Gln Arg Leu Arg Ile Val
65                 70                 75                 80

Arg Gly Thr Gln Leu Phe Glu Asp Asn Tyr Ala Leu Ala Val Leu Asp
                85                 90                 95

Asn Gly Asp Pro Leu Asn Asn Thr Thr Pro Val Thr Gly Ala Ser Pro
            100                105                110

Gly Gly Leu Arg Glu Leu Gln Leu Arg Ser Leu Thr Glu Ile Leu Lys
            115                120                125

Gly Gly Val Leu Ile Gln Arg Asn Pro Gln Leu Cys Tyr Gln Asp Thr
    130                135                140

Ile Leu Trp Lys Asp Ile Phe His Lys Asn Asn Gln Leu Ala Leu Thr
145                150                155                160

Leu Ile Asp Thr Asn Arg Ser Arg Ala Cys His Pro Cys Ser Pro Met
            165                170                175

Cys Lys Gly Ser Arg Cys Trp Gly Glu Ser Ser Glu Asp Cys Gln Ser
            180                185                190

Leu Thr Arg Thr Val Cys Ala Gly Gly Cys Ala Arg Cys Lys Gly Pro
            195                200                205

Leu Pro Thr Asp Cys Cys His Glu Gln Cys Ala Ala Gly Cys Thr Gly
    210                215                220

Pro Lys His Ser Asp Cys Leu Ala Cys Leu His Phe Asn His Ser Gly
225                230                235                240

Ile Cys Glu Leu His Cys Pro Ala Leu Val Thr Tyr Asn Thr Asp Thr
            245                250                255

Phe Glu Ser Met Pro Asn Pro Glu Gly Arg Tyr Thr Phe Gly Ala Ser
            260                265                270

Cys Val Thr Ala Cys Pro Tyr Asn Tyr Leu Ser Thr Asp Val Gly Ser
    275                280                285

Cys Thr Leu Val Cys Pro Leu His Asn Gln Glu Val Thr Ala Glu Asp
    290                295                300

Gly Thr Gln Arg Cys Glu Lys Cys Ser Lys Pro Cys Ala Arg Val Cys
305                310                315                320

Tyr Gly Leu Gly Met Glu His Leu Arg Glu Val Arg Ala Val Thr Ser
            325                330                335

Ala Asn Ile Gln Glu Phe Ala Gly Cys Lys Lys Ile Phe Gly Ser Leu
            340                345                350

Ala Phe Leu Pro Glu Ser Phe Asp Gly Asp Pro Ala Ser Asn Thr Ala
            355                360                365

Pro Leu Gln Pro Glu Gln Leu Gln Val Phe Glu Thr Leu Glu Glu Ile
    370                375                380

Thr Gly Tyr Leu Tyr Ile Ser Ala Trp Pro Asp Ser Leu Pro Asp Leu
385                390                395                400

Ser Val Phe Gln Asn Leu Gln Val Ile Arg Gly Arg Ile Leu His Asn
            405                410                415

Gly Ala Tyr Ser Leu Thr Leu Gln Gly Leu Gly Ile Ser Trp Leu Gly
```

-continued

```
                420              425              430
Leu Arg Ser Leu Arg Glu Leu Gly Ser Gly Leu Ala Leu Ile His His
            435              440              445

Asn Thr His Leu Cys Phe Val His Thr Val Pro Trp Asp Gln Leu Phe
    450              455              460

Arg Asn Pro His Gln Ala Leu Leu His Thr Ala Asn Arg Pro Glu Asp
465              470              475              480

Glu Cys Val Gly Glu Gly Leu Ala Cys His Gln Leu Cys Ala Arg Gly
                485              490              495

His Cys Trp Gly Pro Gly Pro Thr Gln Cys Val Asn Cys Ser Gln Phe
                500              505              510

Leu Arg Gly Gln Glu Cys Val Glu Glu Cys Arg Val Leu Gln Gly Leu
            515              520              525

Pro Arg Glu Tyr Val Asn Ala Arg His Cys Leu Pro Cys His Pro Glu
            530              535              540

Cys Gln Pro Gln Asn Gly Ser Val Thr Cys Phe Gly Pro Glu Ala Asp
545              550              555              560

Gln Cys Val Ala Cys Ala His Tyr Lys Asp Ala Ala Phe Cys Val Ala
                565              570              575

Arg Cys Pro Ser Gly Val Lys Pro Asp Leu Ser Tyr Met Pro Ile Trp
            580              585              590

Lys Phe Pro Asp Glu Glu Gly Ala Cys Gln Pro Cys Pro Ile Asn Cys
            595              600              605

Thr His Ser Cys Val Asp Leu Asp Asp Lys Gly Cys Pro Ala Glu Gln
    610              615              620

Arg Ala Ser Pro Leu Thr
625              630
```

<210> SEQ ID NO 80
<211> LENGTH: 1350
<212> TYPE: DNA
<213> ORGANISM: Artificial Sequence
<220> FEATURE:
<223> OTHER INFORMATION: Synthetic oligonucleotide

<400> SEQUENCE: 80

```
gaggtgcagc tcgtggagag cggcggcggc ctggtgcagc ccggcggcag cctgcgcctg      60
agctgcgccg ccagcggctt caacatcaag gacacctaca tccactgggt gcgccaggcc     120
cccggcaagg gcctggagtg ggtggcccgc atctacccca ccaacggcta cacccgctac     180
gccgacagcg tgaagggccg cttcaccatc agcgccgaca ccagcaagaa caccgcctac     240
ctgcagatga acagcctgcg cgccgaggac accgccgtgt actactgcag ccgctggggc     300
ggcgacggct tctacgccat ggactactgg ggccagggca ccctggtgac cgtgagcagc     360
gccagcacca agggccccag cgtgttcccc ctggcccca gcagcaagag caccagcggc     420
ggcaccgccg ccctgggctg cctggtgaag gactacttcc ccgagcccgt gaccgtgagc     480
tggaacagcg gcgccctgac cagcggcgtg cacaccttcc ccgccgtgct gcagagcagc     540
ggcctgtaca gcctgagcag cgtggtgacc gtgcccagca gcagcctggg cacccagacc     600
tacatctgca acgtgaacca caagcccagc aacaccaagg tggacaagaa ggtggagccc     660
aagagctgcg acaagaccca cacctgcccc cctgccccg ccccgagct gctgggcggc     720 cccagcgtgt tcctgttccc ccccaagccc aaggacaccc tgatgatcag ccgcacccc     780 gaggtgacct gcgtggtggt ggacgtgagc cacgaggacc ccgaggtgaa gttcaactgg     840
```

-continued

```
tacgtggacg gcgtggaggt gcacaacgcc aagaccaagc cccgcgagga gcagtacaac      900
agcacctacc gcgtggtgag cgtgctgacc gtgctgcacc aggactggct gaacggcaag      960
gagtacaagt gcaaggtgag caacaaggcc ctgcccgccc ccatcgagaa gaccatcagc     1020
aaggccaagg gccagccccg cgagcccag gtgtacaccc tgcccccag ccgcgaggag       1080 atgaccaaga accaggtgag cctgacctgc ctggtgaagg gcttctaccc cagcgacatc     1140
gccgtggagt gggagagcaa cggccagccc gagaacaact acaagaccac cccccccgtg     1200
ctggacagcg acggcagctt cttcctgtac agcaagctga ccgtggacaa gagccgctgg     1260
cagcagggca cgtgttctc gtgcagcgtg atgcacgagg ccctgcacaa ccactacacc     1320
cagaagagcc tgagcctgag ccccggcaag                                     1350
```

```
<210> SEQ ID NO 81
<211> LENGTH: 1347
<212> TYPE: DNA
<213> ORGANISM: Artificial Sequence
<220> FEATURE:
<223> OTHER INFORMATION: Synthetic oligonucleotide

<400> SEQUENCE: 81
gaggtgcagc tcgtggagag cggcggcggc ctggtgcagc ccggcggcag cctgcgcctg       60
agctgcgccg ccagcggctt caccttcacc gactacacca tggactgggt gcgccaggcc      120
cccggcaagg gcctggagtg ggtggccgac gtgaaccca acagcggcgg cagcatctac      180
aaccagcgct tcaagggccg cttcacccctg agcgtggacc gcagcaagaa caccctgtac      240
ctgcagatga acagcctgcg cgccgaggac accgccgtgt actactgcgc cgcaacctg      300 ggccccagct tctacttcga ctactggggc cagggcaccc tggtgaccgt gagcagcgcc      360
agcaccaagg gccccagcgt gttccccctg gcccccagca gcaagagcac cagcggcggc      420
accgccgccc tgggctgcct ggtgaaggac tacttccccg agcccgtgac cgtgagctgg      480
aacagcggcg ccctgaccag cggcgtgcac accttccccg ccgtgctgca gagcagcggc      540
ctgtacagcc tgagcagcgt ggtgaccgtg cccagcagca gcctgggcac ccagacctac      600
atctgcaacg tgaaccacaa gcccagcaac accaaggtgg acaagaaggt ggagcccaag      660
agctgcgaca gacccacac ctgcccccccc tgccccgccc ccgagctgct gggcggcccc      720
agcgtgttcc tgttcccccc caagcccaag gacaccctga tgatcagccg cacccccgag      780
gtgacctgcg tggtggtgga cgtgagccac gaggacccg aggtgaagtt caactggtac      840
gtggacggcg tggaggtgca caacgccaag accaagcccc gcgaggagca gtacaacagc      900
acctaccgcg tggtgagcgt gctgaccgtg ctgcaccagg actggctgaa cggcaaggag      960
tacaagtgca aggtgagcaa caaggccctg cccgccccca tcgagaagac catcagcaag     1020
gccaagggcc agccccgcga gccccaggtg tacaccctgc ccccagccg cgaggagatg      1080 accaagaacc aggtgagcct gacctgcctg gtgaagggct ctacccccag cgacatcgcc     1140
gtggagtggg agagcaacgg ccagcccgag aacaactaca agaccacccc ccccgtgctg      1200
gacagcgacg gcagcttctt cctgtacagc aagctgaccg tggacaagag ccgctggcag     1260
cagggcaacg tgttctcgtg cagcgtgatg cacgaggccc tgcacaacca ctacacccag      1320
aagagcctga gcctgagccc cggcaag                                        1347
```

```
<210> SEQ ID NO 82
<211> LENGTH: 630
<212> TYPE: PRT
<213> ORGANISM: Artificial Sequence
```

-continued

```
<220> FEATURE:
<223> OTHER INFORMATION: Synthetic HER2-ECD

<400> SEQUENCE: 82

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
            115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
            195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
            275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
            325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
            355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400
```

-continued

```
Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
            595                 600                 605

Thr His Ser Cys Val Asp Leu Asp Asp Lys Gly Cys Pro Ala Glu Gln
    610                 615                 620

Arg Ala Ser Pro Leu Thr
625                 630

<210> SEQ ID NO 83
<211> LENGTH: 450
<212> TYPE: PRT
<213> ORGANISM: Artificial Sequence
<220> FEATURE:
<223> OTHER INFORMATION: Synthetic peptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135             140

Leu Gly Cys Leu Val Lys Asp Tyr Phe Pro Glu Pro Val Thr Val Ser
145                 150             155                 160

Trp Asn Ser Gly Ala Leu Thr Ser Gly Val His Thr Phe Pro Ala Val
                165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
    210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Cys Arg Asp Glu Leu Thr Lys Asn Gln Val Ser Leu
            355             360             365

Trp Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450

<210> SEQ ID NO 84
<211> LENGTH: 449
<212> TYPE: PRT
<213> ORGANISM: Artificial Sequence
<220> FEATURE:
<223> OTHER INFORMATION: Synthetic peptide

<400> SEQUENCE: 84

Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Thr Asp Tyr
        20              25              30
```

-continued

```
Thr Met Asp Trp Val Arg Gln Ala Pro Gly Lys Gly Leu Glu Trp Val
        35              40              45

Ala Asp Val Asn Pro Asn Ser Gly Gly Ser Ile Tyr Asn Gln Arg Phe
    50              55              60

Lys Gly Arg Phe Thr Leu Ser Val Asp Arg Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Asn Leu Gly Pro Ser Phe Tyr Phe Asp Tyr Trp Gly Gln Gly
                100             105             110

Thr Leu Val Thr Val Ser Ser Ala Ser Thr Lys Gly Pro Ser Val Phe
            115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
                165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
            195             200             205

Ser Asn Thr Lys Val Asp Lys Lys Val Glu Pro Lys Ser Cys Asp Lys
    210             215             220

Thr His Thr Cys Pro Pro Cys Pro Ala Pro Glu Leu Leu Gly Gly Pro
225             230             235             240

Ser Val Phe Leu Phe Pro Pro Lys Pro Lys Asp Thr Leu Met Ile Ser
                245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Cys Thr
                340             345             350

Leu Pro Pro Ser Arg Asp Glu Leu Thr Lys Asn Gln Val Ser Leu Ser
            355             360             365

Cys Ala Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Val Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445
```

-continued

Lys

<210> SEQ ID NO 85
<211> LENGTH: 450
<212> TYPE: PRT
<213> ORGANISM: Artificial Sequence
<220> FEATURE:
<223> OTHER INFORMATION: Synthetic peptide

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu

-continued

```
              355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 86
<211> LENGTH: 449
<212> TYPE: PRT
<213> ORGANISM: Artificial Sequence
<220> FEATURE:
<223> OTHER INFORMATION: Synthetic peptide

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Thr Met Asp Trp Val Arg Gln Ala Pro Gly Lys Gly Leu Glu Trp Val
                35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

-continued

```
              260              265              270

Pro Glu Val Lys Phe Asn Trp Tyr Val Asp Gly Val Glu Val His Asn
        275              280              285

Ala Lys Thr Lys Pro Arg Glu Glu Gln Tyr Asn Ser Thr Tyr Arg Val
    290              295              300

Val Ser Val Leu Thr Val Leu His Gln Asp Trp Leu Asn Gly Lys Glu
305              310              315              320

Tyr Lys Cys Lys Val Ser Asn Lys Ala Leu Pro Ala Pro Ile Glu Lys
            325              330              335

Thr Ile Ser Lys Ala Lys Gly Gln Pro Arg Glu Pro Gln Val Tyr Thr
            340              345              350

Leu Pro Pro Ser Arg Asp Glu Leu Thr Lys Asn Gln Val Ser Leu Thr
            355              360              365

Cys Leu Val Lys Gly Phe Tyr Pro Ser Asp Ile Ala Val Glu Trp Glu
    370              375              380

Ser Asn Gly Gln Pro Glu Asn Asn Tyr Asp Thr Thr Pro Pro Val Leu
385              390              395              400

Lys Ser Asp Gly Ser Phe Phe Leu Tyr Ser Asp Leu Thr Val Asp Lys
            405              410              415

Ser Arg Trp Gln Gln Gly Asn Val Phe Ser Cys Ser Val Met His Glu
            420              425              430

Ala Leu His Asn His Tyr Thr Gln Lys Ser Leu Ser Leu Ser Pro Gly
            435              440              445

Lys

<210> SEQ ID NO 87
<211> LENGTH: 120
<212> TYPE: PRT
<213> ORGANISM: Artificial Sequence
<220> FEATURE:
<223> OTHER INFORMATION: Synthetic peptide

<400> SEQUENCE: 87

Glu Val Gln Leu Val Glu Ser Gly Gly Gly Leu Val Gln Pro Gly Gly
1                5               10               15

Ser Leu Arg Leu Ser Cys Ala Ala Ser Gly Phe Asn Ile Lys Asp Thr
            20               25               30

Tyr Ile His Trp Val Arg Gln Ala Pro Gly Lys Gly Leu Glu Trp Val
        35               40               45

Ala Arg Ile Tyr Pro Thr Asn Gly Tyr Thr Arg Tyr Ala Asp Ser Val
    50               55               60

Lys Gly Arg Phe Thr Ile Ser Ala Asp Thr Ser Lys Asn Thr Ala Tyr
65               70               75               80

Leu Gln Met Asn Ser Leu Arg Ala Glu Asp Thr Ala Val Tyr Tyr Cys
            85               90               95

Ser Arg Trp Gly Gly Asp Gly Phe Tyr Ala Met Asp Tyr Trp Gly Gln
            100              105              110

Gly Thr Leu Val Thr Val Ser Ser
        115              120

<210> SEQ ID NO 88
<211> LENGTH: 119
<212> TYPE: PRT
<213> ORGANISM: Artificial Sequence
<220> FEATURE:
<223> OTHER INFORMATION: Synthetic peptide
```

-continued

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 89
<211> LENGTH: 227
<212> TYPE: PRT
<213> ORGANISM: Artificial Sequence
<220> FEATURE:
<223> OTHER INFORMATION: Synthetic peptide

<400> SEQUENCE: 89

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys

```
225

<210> SEQ ID NO 90
<211> LENGTH: 227
<212> TYPE: PRT
<213> ORGANISM: Artificial Sequence
<220> FEATURE:
<223> OTHER INFORMATION: Synthetic peptide

<400> SEQUENCE: 90

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225
```

COMBINATION OF BISPECIFIC FUSION PROTEIN AND ANTI-Her2 ANTIBODY FOR TUMOR TREATMENT

CROSS REFERENCE TO RELATED APPLICATIONS

This application is a National Stage Application and claims priority under 35 U.S.C. § 371 to Patent Cooperation Treaty application PCT/CN2020/133667, filed Dec. 3, 2020, which claims the benefit of Patent Cooperation Treaty application PCT/CN2020/127559, filed Nov. 9, 2020, and Patent Cooperation Treaty application PCT/CN2019/123070, filed Dec. 4, 2019. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2022 Jun. 3 262790-510725 ST25", is 192,692 bytes in size and was created on Jun. 3, 2022, and filed electronically herewith.

BACKGROUND OF THE INVENTION

The immune system plays an important role in the anti-tumor effect of anti-Her2 antibodies, such as the ADCC effect of anti-Her2 antibodies and is related to T cell function. A patient with a higher level of TILs have a better response to anti-Her2 antibodies. Conversely, patients who don't achieve pathological complete remission (pCR) have increased Treg level, and present to be immunosuppressed.

Animal experiments have also shown that Tratuzumab can cause an increased IFN-$\gamma$ secretion, thereby induce the PDL1 expression. And the pathway may become one of the mechanisms of Trastuzumab resistance.

Preclinical experiments have confirmed that the therapeutic effect of Her2 target depends on the body's adaptive immune response. Thus, combination with tumor immune-related (target such as PD1/PDL1, CTLA4 or 4-1BB can enhance the anti-tumor effect of drugs synergistically.

SUMMARY OF THE INVENTION

The present disclosure provides a use of an immune checkpoint inhibitor in combination with a Her2 inhibitor in the preparation of a medicament for treating tumor in a subject in need thereof, wherein said immune checkpoint inhibitor is capable of specifically binding to PD-L1 and CTLA4, and also provides a pharmaceutical composition comprising an effective amount of said immune checkpoint inhibitor and an effective amount of said Her2 inhibitor, and optionally a pharmaceutically acceptable excipient, as well as a use of the pharmaceutical composition in the preparation of a medicament for treating tumor in a subject in need thereof.

In one aspect, the present disclosure provides a use of an immune checkpoint inhibitor in combination with a Her2 inhibitor in the preparation of a medicament for treating tumor in a subject in need thereof, wherein said immune checkpoint inhibitor is capable of specifically binding to PD-L1 and CTLA4.

In some embodiments, said immune checkpoint inhibitor is a bispecific antibody or an antigen binding fragment thereof.

In some embodiments, said immune checkpoint inhibitor is a bispecific antibody, and said bispecific antibody is a fully human antibody.

In some embodiments, said immune checkpoint inhibitor is an antigen binding fragment, and said antigen binding fragment comprises Fab, Fab', F(ab)$_2$, Fv fragment, F(ab')$_2$, scFv, di-scFv and/or dAb.

In some embodiments, said immune checkpoint inhibitor is a dimer, and said dimer formed by two polypeptide chains, with each of said two polypeptide chains comprising an antibody Fc subunit, wherein said dimer comprises two or more immunoglobulin single variable domains (ISVDs), at least one of said ISVDs is specific for PD-L1, and at least one of said ISVDs is specific for CTLA4.

In some embodiments, at least one of said two polypeptide chains comprise both an ISVD specific for PD-L1 and an ISVD specific for CTLA4.

In some embodiments, each of said two polypeptide chains comprises both an ISVD specific for PD-L1 and an ISVD specific for CTLA4.

In some embodiments, for one or both of said two polypeptide chains, said ISVD specific for PD-L1 is fused to said ISVD specific for CTLA4, optionally via a linker.

In some embodiments, for one or both of said two polypeptide chains: said ISVD specific for PD-L1 is fused to said ISVD specific for CTLA4, optionally via a linker; and said ISVD specific for CTLA4 is fused to said antibody Fc subunit, optionally via a linker.

In some embodiments, for one or both of said two polypeptide chains: C terminus of said ISVD specific for PD-L1 is fused to N terminus of said ISVD specific for CTLA4, optionally via a linker; and C terminus of said ISVD specific for CTLA4 is fused to N terminus of said antibody Fc subunit, optionally via a linker.

In some embodiments, for one or both of said two polypeptide chains: said ISVD specific for PD-L1 is fused to said ISVD specific for CTLA4, optionally via a linker; and said ISVD specific for PD-L1 is fused to said antibody Fc subunit, optionally via a linker.

In some embodiments, for one or both of said two polypeptide chains: C terminus of said ISVD specific for CTLA4 is fused to N terminus of said ISVD specific for PD-L1, optionally via a linker; and C terminus of said ISVD specific for PD-L1 is fused to N terminus of said antibody Fc subunit, optionally via a linker.

In some embodiments, said antibody Fc subunit is derived from an IgG Fc subunit.

In some embodiments, said IgG is human IgG1.

In some embodiments, said antibody Fc subunit comprises an amino acid sequence as set forth in any one of SEQ ID NO: 35, 38 and 39.

In some embodiments, said ISVD specific for PD-L1 is capable of binding to N-terminal IgV domain of human PD-L1.

In some embodiments, said ISVD specific for PD-L1 is capable of binding to residues I54, Y56, E58, Q66 and/or R113 of human PD-L1 N-terminal IgV domain, wherein said human PD-L1 N-terminal IgV domain comprises an amino acid sequence as set forth in SEQ ID NO: 64.

In some embodiments, said ISVD specific for PD-L1 is capable of further binding to residues D61, N63, V68, M115, S117, Y123 and/or R125 of human PD-L1 N-terminal IgV domain, wherein said human PD-L1 N-terminal IgV domain comprises an amino acid sequence as set forth in SEQ ID NO: 64.

In some embodiments, said ISVD specific for PD-L1 is capable of binding to a conformational epitope of human PD-L1 N-terminal IgV domain, wherein said conformational epitope comprises residues I54, Y56, E58, Q66 and R113 of said human PD-L1 N-terminal IgV domain, and wherein said human PD-L1 N-terminal IgV domain comprises an amino acid sequence as set forth in SEQ ID NO: 64.

In some embodiments, said ISVD specific for PD-L1 is capable of binding to a conformational epitope of human PD-L1 N-terminal IgV domain, wherein said conformational epitope comprises residues I54, Y56, E58, Q66, R113, D61, N63, V68, M115, S117, Y123 and R125 of said human PD-L1 N-terminal IgV domain, and wherein said human PD-L1 N-terminal IgV domain comprises an amino acid sequence as set forth in SEQ ID NO: 64.

In some embodiments, said ISVD specific for PD-L1 is capable of blocking binding of PD-L1 to PD1.

In some embodiments, said ISVD specific for PD-L1 is capable of blocking binding of PD-L1 to CD80.

In some embodiments, said ISVD specific for PD-L1 cross-competes for binding to PD-L1 with a reference anti-PD-L1 antibody, wherein said reference anti-PD-L1 antibody comprises a heavy chain CDR3 comprising an amino acid sequence as set forth in SEQ ID NO: 1.

In some embodiments, said reference anti-PD-L1 antibody comprises a heavy chain CDR3 comprising an amino acid sequence as set forth in any one of SEQ ID NO: 5 and 9.

In some embodiments, said reference anti-PD-L1 antibody comprises a heavy chain CDR1 comprising an amino acid sequence as set forth in SEQ ID NO: 2.

In some embodiments, said reference anti-PD-L1 antibody comprises a heavy chain CDR1 comprising an amino acid sequence as set forth in any one of SEQ ID NO: 3 and 7.

In some embodiments, said reference anti-PD-L1 antibody comprises a heavy chain CDR2 comprising an amino acid sequence as set forth in any one of SEQ ID NO: 4, 8 and 11.

In some embodiments, said reference anti-PD-L1 antibody is an ISVD specific for PD-L1.

In some embodiments, said reference anti-PD-L1 antibody comprises a heavy chain variable domain comprising an amino acid sequence as set forth in any one of SEQ ID NO: 6, 10, 12, 13, 14 and 15.

In some embodiments, said reference anti-PD-L1 antibody comprises a heavy chain variable domain comprising an amino acid sequence as set forth in SEQ ID NO: 6.

In some embodiments, said ISVD specific for PD-L1 comprises a heavy chain CDR3 comprising an amino acid sequence as set forth in SEQ ID NO: 1.

In some embodiments, said ISVD specific for PD-L1 comprises a heavy chain CDR3 comprising an amino acid sequence as set forth in any one of SEQ ID NO: 5 and 9.

In some embodiments, said ISVD specific for PD-L1 comprises a heavy chain CDR1 comprising an amino acid sequence as set forth in SEQ ID NO: 2.

T In some embodiments, said ISVD specific for PD-L1 comprises a heavy chain CDR1 comprising an amino acid sequence as set forth in any one of SEQ ID NO: 3 and 7.

In some embodiments, said ISVD specific for PD-L1 comprises a heavy chain CDR2 comprising an amino acid sequence as set forth in any one of SEQ ID NO: 4, 8 and 11.

In some embodiments, said ISVD specific for PD-L1 comprises a heavy chain variable domain comprising an amino acid sequence as set forth in any one of SEQ ID NO: 6, 10, 12, 13, 14 and 15.

In some embodiments, said ISVD specific for PD-L1 comprises a heavy chain variable domain comprising an amino acid sequence as set forth in SEQ ID NO: 6.

In some embodiments, said ISVD specific for CTLA4 is capable of specifically binding to human CTLA4.

In some embodiments, said ISVD specific for CTLA4 is capable of blocking binding of CTLA4 to CD80.

In some embodiments, said ISVD specific for CTLA4 is capable of blocking binding of CTLA4 to CD86.

In some embodiments, said ISVD specific for CTLA4 cross-competes for binding to CTLA4 with a reference anti-CTLA4 antibody, wherein said reference anti-CTLA4 antibody comprises a heavy chain CDR3 comprising an amino acid sequence as set forth in SEQ ID NO: 19.

In some embodiments, reference anti-CTLA4 antibody comprises a heavy chain CDR1 comprising an amino acid sequence as set forth in SEQ ID NO: 17.

In some embodiments, said reference anti-CTLA4 antibody comprises a heavy chain CDR2 comprising an amino acid sequence as set forth in SEQ ID NO: 16.

In some embodiments, said reference anti-CTLA4 antibody comprises a heavy chain CDR2 comprising an amino acid sequence as set forth in any one of SEQ ID NO: 18, 21 and 23.

In some embodiments, said reference anti-CTLA4 antibody is an ISVD specific for CTLA4.

In some embodiments, said reference anti-CTLA4 antibody comprises a heavy chain variable domain comprising an amino acid sequence as set forth in any one of SEQ ID NO: 20, 22, and 24-32.

In some embodiments, said reference anti-CTLA4 antibody comprises a heavy chain variable domain comprising an amino acid sequence as set forth in SEQ ID NO: 20.

In some embodiments, said ISVD specific for CTLA4 comprises a heavy chain CDR3 comprising an amino acid sequence as set forth in SEQ ID NO: 19.

In some embodiments, said ISVD specific for CTLA4 comprises a heavy chain CDR1 comprising an amino acid sequence as set forth in SEQ ID NO: 17.

In some embodiments, said ISVD specific for CTLA4 comprises a heavy chain CDR2 comprising an amino acid sequence as set forth in SEQ ID NO: 16.

In some embodiments, said ISVD specific for CTLA4 comprises a heavy chain CDR2 comprising an amino acid sequence as set forth in any one of SEQ ID NO: 18, 21 and 23.

In some embodiments, said ISVD specific for CTLA4 comprises a heavy chain variable domain comprising an amino acid sequence as set forth in any one of SEQ ID NO: 20, 22, and 24-32.

In some embodiments, said ISVD specific for CTLA4 comprises a heavy chain variable domain comprising an amino acid sequence as set forth in SEQ ID NO: 20.

In some embodiments, said dimer is a homodimer.

In some embodiments, said linker comprises an amino acid sequence as set forth in any one of SEQ ID NO: 33-34.

In some embodiments, one or both of said two polypeptide chains comprises an amino acid sequence as set forth in any one of SEQ ID NO: 40-43, 46, 48 and 50.

In some embodiments, one or both of said two polypeptide chains comprises an amino acid sequence as set forth in SEQ ID NO 40.

In some embodiments, said dimer is capable of blocking binding of PD-L1 to PD-1.

In some embodiments, said dimer is capable of blocking binding of PD-L1 to CD80.

In some embodiments, said dimer is capable of blocking binding of CTLA4 to CD80.

In some embodiments, said dimer is capable of blocking binding of CTLA4 to CD86.

In some embodiments, said Her2 inhibitor is capable of inhibiting human Her2.

In some embodiments, said Her2 inhibitor is a Her2 antibody or an antigen binding portion thereof and/or a conjugate thereof.

In some embodiments, a Her2 antibody is selected from a group consisting of Pertuzumab, Trastuzumab and Margetuximab.

In some embodiments, said conjugate is selected from a group consisting of DS8201a and T-DM1.

In some embodiments, said Her2 inhibitor is a bispecific antibody or an antigen binding portion thereof, and is capable of binding to different epitopes of human Her2.

In some embodiments, said Her2 inhibitor is a bispecific antibody or the antigen binding portion thereof, and said bispecific antibody or the antigen binding portion thereof has a common light chain, and wherein said common light chain refers to two light chains having the same sequence.

In some embodiments, heavy chains thereof are capable of correctly assembling with said light chains respectively under physiological conditions or during in vitro protein expression.

In some embodiments, the common light chain is capable of assembling with a heavy chain of Pertuzumab and a heavy chain of Trastuzumab, respectively.

In some embodiments, the common light chain is selected from a light chain of Pertuzumab, a light chain of Trastuzumab, or a mutant thereof.

In some embodiments, a sequence of a variable region of the common light chain comprises a sequence selected from those as set forth in amino acid positions 1 to 107 of SEQ ID NO: 65~SEQ ID NO: 70.

In some embodiments, heavy chain variable regions thereof are a heavy chain variable region of Pertuzumab and a heavy chain variable region of Trastuzumab, respectively, for example, the heavy chain variable regions comprise sequences as set forth in SEQ ID NO: 87 and SEQ ID NO: 88, respectively.

In some embodiments, Fc fragment sequences of the heavy chains comprise sequences as set forth in SEQ ID: 89 and SEQ ID NO: 90, respectively.

In some embodiments, two heavy chains thereof comprise a sequence as set forth in SEQ ID NO: 83 and SEQ ID NO: 84, respectively.

In some embodiments, said Her2 inhibitor is administrated at dose of 0.01 mg/kg to 100 mg/kg.

In some embodiments, said Her2 inhibitor is administrated at dose of 20 mg/kg to 30 mg/kg.

In some embodiments, said immune checkpoint inhibitor is administrated at dose of 0.01 mg/kg to 100 mg/kg.

In some embodiments, said immune checkpoint inhibitor is administrated at dose of 3 mg/kg to 5 mg/kg.

In some embodiments, said Her2 inhibitor is administrated at a dosing frequency of four times a week, twice a week, once a week, once every two weeks, once every three weeks, once every four weeks, once every five weeks, once every six weeks, once every eight weeks or once every twelve weeks.

In some embodiments, said Her2 inhibitor is administrated once every two weeks or once every three weeks or with a loading dose.

In some embodiments, said immune checkpoint inhibitor is administrated at a dosing frequency of four times a week, twice a week, once a week, once every two weeks, once every three weeks, once every four weeks, once every five weeks, once every six weeks, once every eight weeks or once every twelve weeks.

In some embodiments, said immune checkpoint inhibitor is administrated once every two weeks or once every three weeks.

In some embodiments, said Her2 inhibitor is administrated intravenously, intramuscularly, subcutaneously, topically, orally, transdermally, intraperitoneally, intraorbitally, by implantation, by inhalation, intrathecally, intraventricularly, or intranasally.

In some embodiments, said Her2 inhibitor is administrated by intravenous administration.

In some embodiments, said immune checkpoint inhibitor is administrated intravenously, intramuscularly, subcutaneously, topically, orally, transdermally, intraperitoneally, intraorbitally, by implantation, by inhalation, intrathecally, intraventricularly, or intranasally.

In some embodiments, said immune checkpoint inhibitor is administrated by intravenous administration.

In some embodiments, said tumor is selected from a group consisting of a solid tumor and a hematologic tumor.

In some embodiments, said tumor is selected from a group consisting of NSCLC, breast cancer, gastric cancer, gastroesophageal junction adenocarcinoma, esophageal adenocarcinoma, colorectal, cervical, ovarian, endometrial, biliary tract, colorectal and urothelial cancer.

In some embodiments, said tumor is selected from a group consisting of Her2 aberrated solid tumor and Her2-positive cancer.

In some embodiments, said subject has been administrated anti-Her2 antibody and/or anti-PD1 agent. In some embodiments, said anti-Her2 antibody comprises trastuzumab.

In some embodiments, said subject has been administrated chemotherapy.

In some embodiments, said chemotherapy comprises first line chemotherapy and/or second line chemotherapy. In some embodiments, said second line chemotherapy comprises paclitaxel plus ramucirumab, paclitaxel, docetaxel and/or irinotecan monotherapy.

In another aspect, the present disclosure provides a pharmaceutical composition comprising an effective amount of said immune checkpoint inhibitor of the present disclosure and an effective amount of said Her2 inhibitor, and optionally a pharmaceutically acceptable excipient.

In another aspect, the present disclosure provides a use of the pharmaceutical composition in the preparation of a medicament for treating tumor in a subject in need thereof.

In some embodiments, said pharmaceutical composition is administrated at a dosing frequency of four times a week, twice a week, once a week, once every two weeks, once every three weeks, once every four weeks, once every five weeks, once every six weeks, once every eight weeks or once every twelve weeks.

In some embodiments, said pharmaceutical composition is administrated intravenously, intramuscularly, subcutaneously, topically, orally, transdermally, intraperitoneally, intraorbitally, by implantation, by inhalation, intrathecally, intraventricularly, or intranasally.

In some embodiments, said pharmaceutical composition is administered at dose of 0.01 mg/kg to 100 mg/kg.

In some embodiments, said tumor selected from a group consisting of a solid tumor and a hematologic tumor.

In some embodiments, said tumor selected from a group consisting of NSCLC, breast cancer, gastric cancer, gastroesophageal junction adenocarcinoma, esophageal adenocarcinoma, colorectal, cervical, ovarian, endometrial, biliary tract, colorectal and urothelial cancer.

In some embodiments, said tumor selected from a group consisting of Her2 aberrated solid tumor and Her2-positive cancer.

In some embodiments, a subject suffering said tumor has been administered anti-Her2 antibody and/or anti-PD1 agent. In some embodiments, said anti-Her2 antibody comprises trastuzumab.

In some embodiments, said subject has been administrated chemotherapy.

In some embodiments, said chemotherapy comprises first line chemotherapy and/or second line chemotherapy. In some embodiments, said second line chemotherapy comprises paclitaxel plus ramucirumab, paclitaxel, docetaxel and/or irinotecan monotherapy.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

Figure 1:
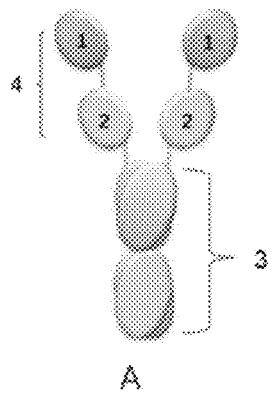
FIG. 1 illustrates examples of the dimers of the present disclosure.
Figure 1:
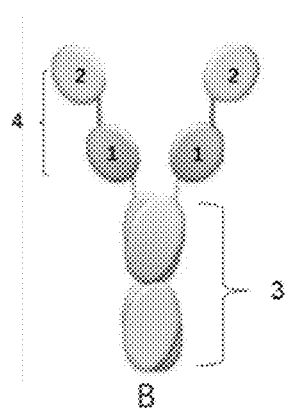

A and B of FIG. 1 provide examples of the dimer of the present disclosure, wherein 1 indicates the ISVD specific for PD-L1, 2 indicates the ISVD specific for CTLA4, 3 indicates the Fc domain comprising the Fc subunits, and 4 indicates the bi-specific binding moiety.

Figure 2:
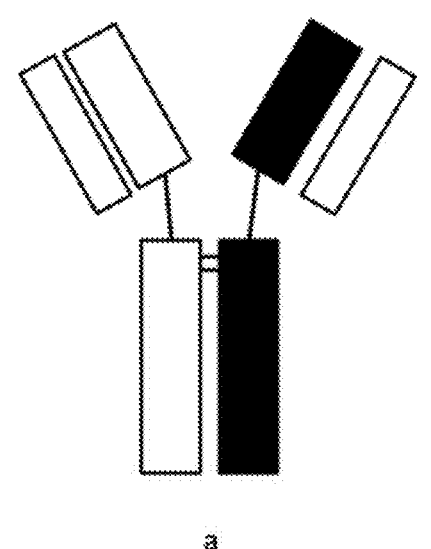
Figure 2:
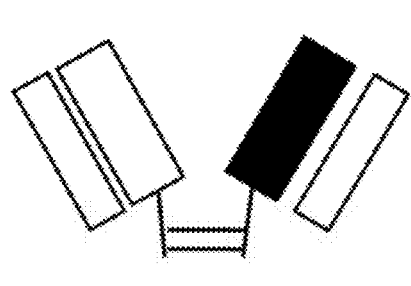

FIG. 2 illustrate a schematic diagram of heterodimer protein fusion. Panel a illustrates a heterodimer Fc fusion technology, and Panel b illustrates a "Fab" technology.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "antibody," as used herein, generally refers to an immunoglobulin or a fragment or a derivative thereof, and encompasses any polypeptide comprising an antigen-binding site, regardless whether it is produced in vitro or in vivo. The term includes, but is not limited to, polyclonal, mono-clonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, $F(ab')_2$, Fv, scFv, Fd, dAb, and other antibody fragments that retain antigen-binding function, i.e., the ability to bind, for example, CTLA-4, or PD-L1 specifically. Typically, such fragments would comprise an antigen-binding domain.

The term "variable region" or "variable domain" of an antibody, as used herein, generally refers to the amino-terminal domains of the heavy or light chain of an antibody. The variable domains of the heavy chain and light chain may be referred to as "VH" and "VL", respectively. These domains are generally the most variable parts of the antibody (relative to other antibodies of the same class) and contain the antigen binding sites.

The term "variable", as used herein, generally refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (CDRs or HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al, Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "CDR," "HVR," or "HV," as used herein, generally refers to the regions of an antibody variable domain which are hypervariable in sequence and/or form structurally defined loops. Generally, antibodies comprise six CDRs; three in the VH (HCDR1, HCDR2, HCDR3), and three in the VL (LCDR1, LCDR2, LCDR3). The ISVD of the present disclosure may only comprise 3 CDRs (e.g., in the VH, HCDR1, HCDR2 and HCDR3). In native antibodies, HCDR3 and LCDR3 display the most diversity of the six CDRs, and HCDR3 in particular is believed to play a unique role in conferring fine specificity to antibodies. See, e.g., Xu et al, Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al, Nature Struct. Biol. 3:733-736 (1996).

A number of CDR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM CDRs represent a compromise between the Kabat HVRs and Chothia structural loops, and are used by Oxford Molecular's AbM antibody modeling software.

The "contact" CDRs are based on an analysis of the available complex crystal structures. The residues from each of these CDRs are noted in Table 1:

TABLE 1

| Loop | Kabat | AbM | Chothia | Contact |
|------|-------|-----|---------|---------|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1(Kabat Numbering) | H31-H35B | H26-H35B | H26-H32 | H30-H35B |
| HCDR1(Chothia Numbering) | H31-H35 | H26-H35 | H26-H32 | H30-H35 |
| HCDR2 | H50-H65 | H50-H58 | H53-H55 | H47-H58 |
| HCDR3 | H95-H102 | H95-H102 | H96-H101 | H93-H101 |

CDRs may comprise "extended CDRs" as follows: 24-36 or 24-34 (LCDR1), 46-56 or 50-56 (LCDR2) and 89-97 or 89-96 (LCDR3) in the VL and 26-35 (HCDR1), 50-65 or 49-65 (HCDR2) and 93-102, 94-102, or 95-102 (HCDR3) in the VH. The variable domain residues are numbered according to Kabat et al., supra, for each of these definitions.

The expression "variable-domain residue-numbering as in Kabat" or "amino-acid-position numbering as in Kabat," and variations thereof, generally refers to the numbering system used for heavy-chain variable domains or light-chain variable domains of the compilation of dimer/polypeptide chain in Kabat et al., supra. The Kabat numbering of residues may be determined for a given polypeptide by alignment at regions of homology of the sequence of the polypeptide with a "standard" Kabat numbered sequence.

"Framework" or "FR" residues are those variable-domain residues other than the CDR residues as herein defined. A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al, supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain preexisting amino acid sequence changes. In some embodiments, the number of pre-existing amino acid changes are 10 or less, 9 or less, 8 or less, 7 or less, 6 or less, 5 or less, 4 or less, 3 or less, or 2 or less.

The term "homology," "homologous" or "sequence identity," as used herein, generally refers to sequence similarity or interchangeability between two or more polynucleotide sequences or between two or more polypeptide sequences. When using a program (e.g. Emboss Needle or BestFit) to determine sequence identity, similarity or homology between two different amino acid sequences, the default settings may be used, or an appropriate scoring matrix, such as blosum45 or blosum80, may be selected to optimize identity, similarity or homology scores. In some embodiments, polynucleotides that are homologous are those which hybridize under stringent conditions and have at least 60%, at least 65%, at least 70%, at least 80%, at least 90%, at least 95%, at least 97%, at least 98%, at least 99%, and even 100% sequence identity with a reference sequence. Polypeptides that are homologous may have a sequence identity of at least 80%, or at least 90%, or at least 95%, or at least 97%, or at least 98%, or at least 99% with each other when sequences of comparable length are optimally aligned.

The term "percent (%) sequence identity," as used in the context of polypeptide sequences identified herein, generally refers to the percentage of amino acid residues or nucleotides in a query sequence that are identical with the amino acid residues or nucleotides of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid/nucleotide sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide/polynucleotide sequence, or may be measured over a shorter length, for example, over the length of a fragment taken from a larger, defined polypeptide/polynucleotide sequence. It is understood that any fragment length supported by the sequences shown herein, in the tables, figures or Sequence Listing, may be used to describe a length over which percentage identity may be measured.

In the present application, the term "bispecific antibody" refers to an antibody that can respectively bind with two antigens or antigen epitopes, comprising a light chain and a heavy chain of an antibody capable of specifically binding to a first antigen or antigen epitope, and a light chain and a heavy chain of an antibody capable of specifically binding to a second antigen or antigen epitope. In one embodiment, in the bispecific antibody, the antibody light chain capable of specifically binding to a first antigen or antigen epitope and the antibody light chain capable of specifically binding to a second antigen or antigen epitope have the same sequences. In one embodiment, in the bispecific antibody, the antibody heavy chain capable of specifically binding to a first antigen or antigen epitope and the antibody heavy chain capable of specifically binding to a second antigen or antigen epitope have different sequences.

The term "PD-L1," as used herein, generally refers to the Programmed Death Ligand 1 protein, its functional variant and/or its functional fragments. PD-L1 is also known as cluster of differentiation 274 (CD274) or B7 homolog 1 (B7-H1), and is a protein encoded by the CD274 gene (in human). PD-L1 binds to its receptor, programmed cell death protein 1 (PD-1), which is expressed in activated T cells, B cells, and macrophages (Ishida et al., 1992 EMBO J, 11:3887-3395; Okazaki et al., Autoimmune dilated cardiomyopathy in PD-1 receptor-deficient mice. *Science,* 2001; 291: 319-22). The complexation of PD-L1 and PD-1 exerts immunosuppressive effects by inhibiting T cell proliferation and cytokine production of IL-2 and IFN-γ (Freeman et al., Engagement of PD-1 immunoinhibitory receptor by a novel B7 family member leads to negative regulation of lymphocyte activation, *J. Exp. Med.* 2000, 192:1027-1034; Carter et al., PD-1: PD-L inhibitory pathway affects both CD4(+) and CD8(+) T cells and is overcome by IL-2. *Eur. J. Immunol.* 2002, 32:634-643). For example, the term "PD-L1" may comprise a polypeptide or a fragment thereof having at least about 85% amino acid sequence identity to NCBI Accession No. Q9NZQ7 and that specifically binds PD1. The term PD-L1 includes the entire PD-L1 ligand, soluble PD-L1 ligand, and fusion proteins comprising a functionally active portion of PD-L1 ligand covalently linked to a second moiety, e.g., a protein domain. Also included within the definition of PD-L1 are variants which vary in amino acid sequence from naturally occurring PD-L1 but which retain the ability to specifically bind to the receptor PD1. Further included within the definition of PD-L1 are variants which enhance the biological activity of PD1. PD-L1 sequences are known in the art and are provided, for example, at GenBank Accession Numbers 29126. The term "PD-L1" as used herein includes human PD-L1 (hPD-L1), variants, isoforms, and species homologs of hPD-L1, and analogs having at least one common epitope with hPD-L1. For example, the term "PD-L1" also encompasses PD-L1 from other species, such as other mammals, for example, rat, mouse, rabbit, non-human primate, pig, or bovine. The complete hPD-L1 sequence can be found under GenBank Accession No. 29126.

The term "N-terminal IgV domain of human PD-L1," as used herein, generally refers to an extracellular domain of human PD-L1 located in its N-terminus. The term "N-terminal IgV domain of human PD-L1" may also refer to epitopes within said domain. The N-terminal IgV domain of the human PD-L1 protein (including the signal peptide) may comprise an amino acid sequence as set forth in SEQ ID NO: 64.

The term "CTLA4," as used herein, generally refers to the Cytotoxic T-Lymphocyte-Associated protein 4, its functional variant and/or its functional fragments. CTLA4 is an immunoinhibitory receptor belonging to the CD28 family. CTLA4 is expressed exclusively on T cells (CD 4$^+$ and CD 8$^+$ cells) in vivo, and binds to two ligands, CD80 and CD86 (also called B7-1 and B7-2, respectively). For example, the term "CTLA4" may comprise a polypeptide or a fragment thereof having at least about 85% amino acid sequence identity to NCBI Accession No. AAL07473.1 and that specifically binds to CD80 and/or CD86. The term "CTLA4" includes the entire CTLA4 receptor, its extracellular domain, and fusion proteins comprising a functionally active portion of CTLA4 covalently linked to a second moiety, e.g., a protein domain. Also included within the definition of CTLA4 are variants which vary in amino acid sequence from naturally occurring CTLA4 but which retain the ability to specifically bind to the ligand CD80 and/or CD86. CTLA4 sequences are known in the art and are provided, for example, at GenBank Accession No. 1493. The term "CTLA4" as used herein includes human CTLA4 (hCTLA4), variants, isoforms, and species homologs of hCTLA4, and analogs having at least one common epitope with hCTLA4. For example, the term "CTLA4" also encompasses CTLA4 from other species, such as other mammals, for example, rat, mouse, rabbit, non-human primate, pig, or bovine. The complete hCTLA4 sequence can be found under GenBank Accession No. 1493.

The term "antibody Fc subunit," as used herein, generally refers to a component of an antibody Fc domain. For example, an antibody Fc domain may be formed by two or more members, and each member may be considered as one Fc subunit. The term "Fc domain," as used herein, generally refers to an Fc part or Fc fragment of an antibody heavy chain. For example, it may refer to the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(-CH4). CH4 is present in IgM, which has no hinge region. The Fc domain or Fc subunit useful in the present disclosure may comprise a CH3 domain. For example, the Fc domain or Fc subunit may comprise a CH2 domain and a CH3 domain. In some embodiments, the Fc domain or Fc subunit may also comprise an immunoglobulin hinge region. For example, the Fc domain or Fc subunit may comprise or consist of, from N-terminus to C-terminus, a CH2 domain and a CH3 domain. In another example, the Fc domain or Fc subunit may comprise or consist of, from N-terminus to C-terminus, an immunoglobulin hinge region, a CH2 domain and a CH3 domain. Amino acid residue positions within the Fc domain or Fc subunit may be determined according to Kabat, E. A. et al., (1991) Sequences of Proteins of Immunological Interest, 5th ed., NIH Publication No. 91-3242.

The term "Fc domain", as used herein, generally refers to a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

Unless indicated otherwise herein, the numbering of the residues in an immunoglobulin chain is that of the EU index as in Kabat et al., Sequences of Proteins of Immunological Interest, 5$^{th}$ Ed. Public Health Service, National Institutes of Health, Bethesda, Md. (1991). The "EU index as in Kabat" refers to the residue numbering of the human IgG1 EU antibody.

The term "dimer," as used herein, generally refers to a macromolecular complex formed by two, usually non-covalently bound, monomer units. Each monomer unit may be a macromolecule, such as a polypeptide chain or a polynucleotide. The term "homodimer," as used herein, generally refers to a dimer composed of or formed by two substantially identical monomers, such as two substantially identical polypeptide chains. In some cases, the two monomers of a homodimer may be different at one or more regions or positions, however, such difference does not cause significant alteration in the function or structure of the monomer. For example, one of ordinary skills in the art would consider the difference between the two monomers to be of little or no biological and/or statistical significance within the context of the biological characteristic considered in the present disclosure. The structural/compositional difference between said two monomers may be, for example, less than about 50%, less than about 40%, less than about 30%, less than about 20%, less than about 10%, less than about 5%, or less.

The term "fused" or "fusion," as used herein, generally refers the covalent linkage between two polypeptides. The polypeptides are typically joined via a peptide bond, either directly to each other or via an amino acid linker. Optionally, the peptides can be joined via non-peptide covalent linkages known to those of skill in the art.

The term "fusion protein" as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "immunoglobulin single variable domain (ISVD)," as used herein, generally refers to antigen-binding domains or fragments such as VHH domains or VH or VL domains, respectively. The terms antigen-binding molecules or antigen-binding protein are used interchangeably and include also the term Nanobodies. The immunoglobulin single variable domains further are light chain variable domain sequences (e.g., a VL-sequence), or heavy chain variable domain sequences (e.g., a VH-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs," or immunoglobulin sequences that are suitable for use as dAbs, or Nanobodies, including but not limited to VHH sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FRs," which are referred to in the art and herein as "Framework region 1" or "FR1"; as "Framework region 2" or "FR2"; as "Framework region 3" or "FR3"; and as "Framework region 4" or "FR4," respectively; which framework regions are interrupted by three complementary determining regions or "CDRs," which are referred to in the art as "Complementarity Determining Region 1" or "CDR1"; as "Complementarity Determining Region 2" or "CDR2"; and as "Complementarity Determining Region 3" or "CDR3," respectively.

The term "humanized," as used herein, generally refers to an antibody or a fragment thereof, in which some, most or all of the amino acids outside the CDR domains of a non-human antibody are replaced with corresponding amino acids derived from human immunoglobulins. For example, in a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to its specific antigen/epitope. A humanized antibody may retain an antigenic specificity similar to that of the original antibody.

The term "epitope" or "antigenic determinant," as used herein, generally refers to a site on an antigen to which an antibody bind. Epitopes can be formed both from contiguous amino acids (linear epitope) or noncontiguous amino acids juxtaposed by tertiary folding of a protein (conformational epitopes). Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "conformational epitope," as used herein, generally refers to noncontiguous amino acid residues of the antigen (such as the PD-L1 antigen) that are juxtaposed by tertiary folding of a protein. These noncontiguous amino acid residues may come together on the surface when the polypeptide chain folds to form the native protein. The conformation epitope contains, but is not limited to, the functional epitope.

In the present application, 20 conventional amino acids and abbreviations thereof comply with conventional rules. Reference may be made to, Immunology—A Synthesis (Edition II, E. S. Golub and D. R. Gren, Eds., Sinauer Associates, Sunderland, Mass. (1991)), which is incorporated herein by reference.

The term "functional epitope," as used herein, generally refers to amino acid residues of an antigen that contribute energetically to the binding of an antibody, i.e. forming an "energetic epitope". Mutation of any one of the energetically contributing residues of the antigen to alanine will disrupt the binding of the antibody such that the relative $K_D$ ratio ($K_D$ mutant/$K_D$ wildtype) of the antibody may be e.g., greater than 2 folds, such as greater than 3 folds, greater than 4 folds, greater than 6 folds, greater than 10 folds, greater than 20 folds, greater than 30 folds, greater than 40 folds, greater than 50 folds, greater than 60 folds, greater than 70 folds, greater than 80 folds, greater than 90 folds, greater than 100 folds, greater than 150 folds, greater than 200 folds, or more.

The term "extracellular domain," as used herein, generally refers to part of a protein (e.g., a membrane protein, such as a receptor) protruding from the outer membrane of a cell organelle and/or a cell. If the polypeptide chain crosses the bilayer several times, the extracellular domain comprises loops entwined through the membrane. An extracellular domain may recognize and respond to a specific ligand.

The term "linker," as used herein, generally refers to a synthetic amino acid sequence that connects or links two polypeptide sequences, e.g., that links two polypeptide domains. A linker may connect two amino acid sequences via peptide bonds. In some embodiments, a linker of the present disclosure connects a biologically active moiety to a second moiety in a linear sequence. For example, a peptide linker may be non-immunogenic and flexible, such as those comprising serine and glycine sequences or repeats of Ala-Ala-Ala. Depending on the particular construct of the dimer, a peptide linker may comprise, e.g., 3-30 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30) amino acid residues.

The term "N-terminal" may be used interchangeably with "N-terminus," and as used herein, they generally refer to the amino terminus/end of a polypeptide chain.

The term "C-terminal" may be used interchangeably with "C-terminus," and as used herein, they generally refer to the carboxyl terminus/end of a polypeptide chain.

The term "about," as used herein, generally refers to a variation that is within a range of normal tolerance in the art, and generally means within ±10%, such as within 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The terms "co-administration", "co-administered" or "co-administering", as used herein, generally refers that one active ingredient (e.g. a dimer) is administered with another active ingredient (e.g. an immune check point inhibitor). The administration of one active ingredient can be carried out either as one single formulation or as two separate formulations (e.g., one for the dimer and one for the immune check point inhibitor). The co-administration can be simultaneous or sequential in either order.

The term "specifically binds to" or "is specific for", as used herein, generally refers to measurable and reproducible inter actions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant ($K_D$) of $<1\times10^{-6}M$, $<1\times10^{-7}M$, $<1\times10^{-8}M$, $<1\times10^{-9}M$, or $<1\times10^{-10}$ M. In certain embodiments, an antibody specifically binds to an epitope on a protein that is conserved among the protein from different species. In another embodiment, specific binding can include, but does not require exclusive binding.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for u and c isotypes. Each L chain has at the N-terminus, a variable domain (VL) followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgK1.

In the present application, the term "antigen binding portion" of the antibody refers to one or more portions of a full-length antibody, the antigen binding portion maintains the ability of binding to an antigen (such as Her2) that is the same as that bound by the antibody, and competes with the full-length antibody for the specific binding to an antigen. General reference is made to Fundamental Immunology, Ch. 7 (Paul, W., ed., edition II, Raven Press, N.Y. (1989), which is incorporated herein by reference in its entirety and for all purposes. The antigen binding portion can be produced using a recombinant DNA technology or through enzymatic or chemical breakage of a full-length antibody. In some cases, the antigen binding portion comprises a polypeptide such as a Fab, a Fab', a F(ab')2, a Fd, a Fv, a dAb, a complementary determining region (CDR) fragment, a single-chain antibody (such as a scFv), a chimeric antibody, and a diabody, and it comprises at least the part of the antibody sufficiently endowing the polypeptide with the specific antigen binding ability. The antigen binding portion (such as the above antibody fragment) of the antibody may be obtained from a given antibody (such as monoclonal antibody 2E12) using a conventional technology (such as recombinant DNA technology or enzymatic or chemical breakage process) known to those skilled in the art, and are screened for its specificity in a process that is the same for screening full-length antibodies.

The term "polypeptide chain," as used herein, generally refers to a macromolecule comprising two or more covalently connected peptides. The peptides within a polypeptide chain may be connected with each other via a peptide bond. Each polypeptide chain may comprise one N-terminus or amino terminus and one C-terminus or carboxy terminus.

The term "CD80," as used herein, generally refers to a ligand for CD28/CTLA4, also known as B7.1, its functional variant and/or its functional fragments. CD80 is generally expressed on the surface of professional antigen presenting cells (APC). For example, the term "CD80" may comprise a polypeptide or a fragment thereof having at least about 85% amino acid sequence identity to NCBI Accession No.

P33681 and that specifically binds CTLA4. Also included within the definition of CD80 are variants which vary in amino acid sequence from naturally occurring CD80 but which retain the ability to specifically bind to CTLA4. Further included within the definition of CD80 are variants which enhance the biological activity of CTLA4. CD80 sequences are known in the art and are provided, for example, at GenBank Accession Numbers P33681. The term "CD80" as used herein includes human CD80 (hCD80), variants, isoforms, and species homologs of hCD80, and analogs having at least one common epitope with hCD80. For example, the term "CD80" also encompasses CD80 from other species, such as other mammals, for example, rat, mouse, rabbit, non-human primate, pig, or bovine. The complete hCD80 sequence can be found under GenBank Accession No. P33681.

The term "CD86," as used herein, generally refers to a ligand for CD28/CTLA4, also known as B7.2, its functional variant and/or its functional fragments. CD86 is generally expressed on the surface of professional antigen presenting cells (APC). For example, the term "CD86" may comprise a polypeptide or a fragment thereof having at least about 85% amino acid sequence identity to NCBI Accession No. P42081 and that specifically binds CTLA4. Also included within the definition of CD86 are variants which vary in amino acid sequence from naturally occurring CD86 but which retain the ability to specifically bind to CTLA4. Further included within the definition of CD86 are variants which enhance the biological activity of CTLA4. CD86 sequences are known in the art and are provided, for example, at GenBank Accession Numbers U04343. The term "CD86" as used herein includes human CD86 (hCD86), variants, isoforms, and species homologs of hCD86, and analogs having at least one common epitope with hCD86. For example, the term "CD86" also encompasses CD86 from other species, such as other mammals, for example, rat, mouse, rabbit, non-human primate, pig, or bovine. The complete hCD86 sequence can be found under GenBank Accession No. U04343.

The term "PD1," as used herein, generally refers to programmed death-1 receptor, also known as CD279, its functional variant and/or its functional fragments. PD1 is generally expressed on T cells, B cells, natural killer T cells, activated monocytes and dendritic cells (DCs). PD1 may bind to its ligands PD-L1 and PD-L2. For example, the term "PD1" may comprise a polypeptide or a fragment thereof having at least about 85% amino acid sequence identity to NCBI Accession No P42081 and that specifically binds PD-L1. Also included within the definition of PD1 are variants which vary in amino acid sequence from naturally occurring PD1 but which retain the ability to specifically bind to PD-L1. Further included within the definition of PD1 are variants which enhance the biological activity of PD-L1. PD1 sequences are known in the art and are provided, for example, at GenBank Accession Number Q15116.3. The term "PD1" as used herein includes human PD1 (hPD1), variants, isoforms, and species homologs of hPD1, and analogs having at least one common epitope with hPD1. For example, the term "PD1" also encompasses PD1 from other species, such as other mammals, for example, rat, mouse, rabbit, non-human primate, pig, or bovine. The complete hPD1 sequence can be found under GenBank Accession No. Q15116.3.

The term "blocking", as used herein, generally refers to an inhibition or reduction of the binding activity between a molecule and its specific binding partner, such as between a ligand and its specific receptor.

The term "blocking antibody" and "antagonist antibody" are used interchangeably herein and generally refers to an antibody that inhibits or reduces a biological activity of the antigen it binds to. In some embodiments, blocking antibodies or antagonist antibodies substantially or completely inhibit the biological activity of the antigen. The PD-L1 specific ISVD or the CTLA4 specific ISVD of the present disclosure may be blocking or antagonistic ISVDs. For example, the PD-L1 specific ISVD of the present disclosure may block the interaction between PD-L1 and its receptor PD-1, and thus the signaling through PD-1 so as to restore a functional response by T-cells from a dysfunctional state to antigen stimulation. The CTLA4 specific ISVD of the present disclosure may block the interaction between CTLA4 and CD80/CD86, and thus the signaling through CTLA4 so as to restore a functional response by T-cells from a dysfunctional state to antigen stimulation.

The term "cross-competes for binding", "cross-competition", "cross-block", "cross-blocked" and "cross-blocking" are used interchangeably herein and generally refers to the ability of an antibody or fragment thereof to interfere with the binding directly or indirectly through allosteric modulation of another antibody of the invention (e.g., the PD-L1 specific ISVD or the CTLA4 specific ISVD of the present disclosure) to the target/antigen (e.g., PD-L1 or CTLA4, respectively). The extent to which an antibody or fragment thereof is able to interfere with the binding of another to the target, and therefore whether it can be said to cross-block or cross-compete according to the invention, can be determined using competition binding assays. One particularly suitable quantitative cross-competition assay uses a FACS-based or an AlphaScreen-based approach to measure competition between the labelled (e.g. His tagged, biotinylated or radio-active labelled) an antibody or fragment thereof and the other an antibody or fragment thereof in terms of their binding to the target. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the invention is up to 100% (e.g. in FACS based competition assay) of the maximum theoretical displacement (e.g. displacement by cold (e.g. unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, such as between 50% to 100%.

The term "substantially reduced," or "substantially different," as used herein, generally refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_D$ values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, generally refers to a sufficiently high degree of similarity between two numeric values (for example, one associated with a molecule of the present disclosure and the other associated with a reference/comparator molecule), such that one of skill in the art would consider the difference between the two values to be of little or no biological and/or statistical significance within the context of the biological characteristic measured by said values {e.g., $K_D$ values). The difference between said two values is, for example, less than about 50%, less than about 40%, less than about 30%, less than about 20%, and/or less than about 10% as a function of the reference/comparator value.

In the present disclosure, an amino acid sequence or nucleotide sequence as set forth in a specific SEQ ID NO. also encompasses homologs or variants thereof having substantially the same function/property thereto. For example, a sequence having at least 90%, at least 91%, at least 92%, at least 93%, at least 94%, at least 95%, at least 96%, at least 97%, at least 98%, at least 99%, or higher sequence identity thereto; and/or a variant having one or more (e.g., a few, such as 1-10, 1-9, 1-8, 1-7, 1-6, 1-5, 1-4, 1-3, 1-2) amino acid or nucleotide addition, deletion or substitution.

The term "tumor," as used herein, generally refers to tumor growth or metastasis, by any clinically measurable degree. The tumor can be a solid tumor, a hematologic tumor, or a lymphoma. For example, the tumor may be selected from lung cancer (such as non-small-cell lung cancer), breast cancer (such as Triple-Negative Breast Cancer), kidney cancer (such as renal cell carcinoma), melanoma, cervical cancer, uterus cancer, pancreatic cancer, peritoneal carcinoma, ovarian cancer, gastric cancer, gastroesophageal junction adenocarcinoma, esophageal adenocarcinoma, biliary tract, urothelial cancer and colon cancer. The tumor may be advanced or metastatic tumor.

The term "subject," as used herein, generally refers to a human or non-human animal, including, but not limited to, a cat, dog, horse, pig, cow, sheep, goat, rabbit, mouse, rat, or monkey.

The term "treating" as used herein, generally refers to having a therapeutic effect and at least partially alleviating or abrogating an abnormal condition in the organism. The term "treating" refers to ameliorating a symptom of a medicament condition in a group of patients to whom the medicament is administered relative to a control group that does not receive the medicament. The effect of the treatment can be monitored by measuring a change or an absence of a change in cell phenotype, a change or an absence of a change in cell proliferation, a change or an absence of a change in the tumor size, a change or an absence of a change in tumor size, a change or an absence of a change in a progressive disease, a change or an absence of a change in a stable disease, a change or an absence of a change in a disease control rate, a change or an absence of a change in a partial response. The term "treating" or "treatment" does not necessarily mean total cure. Any alleviation of any undesired symptom of the disease to any extent or the slowing down of the progress of the disease can be considered treatment. Furthermore, treatment may include acts which may worsen the patient's overall feeling of well being or appearance.

The term "pharmaceutically acceptable excipients", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329).

Except insofar as any conventional carrier is incompatible with the active ingredient, its use in the therapeutic or pharmaceutical compositions is contemplated.

The term "an effective amount" of a compound of the present disclosure, generally refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

The terms "antigen binding fragment", as used herein, generally refers to a part of an antibody molecule that comprises amino acids responsible for the specific binding between antibody and antigen. The part of the antigen that is specifically recognized and bound by the antibody is referred to as the "epitope" as described herein above. As mentioned above, an antigen-binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of antigen-binding fragments of an antibody include (1) a Fab fragment, a monovalent fragment having the VL, VH, constant light (CL) and CH1 domains; (2) a F(ab') 2 fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., "Binding Activities of a Repertoire of Single Immunoglobulin Variable Domains Secreted From *Escherichia coli*," Nature 341:544-546 (1989), which is hereby incorporated by reference) which has a VH domain; (6) an isolated complementarity determining region (CDR), and (7) a single chain Fv (scFv), for example, derived from a scFV-library. Although the two domains of the Fv fragment, VL and VH are coded for by separate genes, they can be joined, using recombinant methods, by a synthetic linker that enables them to be made as a single protein chain in which the VL and VH regions pair to form monovalent molecules (known as single chain Fv (scFv) (see e.g., Huston et al., "Protein Engineering of Antibody Binding Sites: Recovery of Specific Activity in an Anti-Digoxin Single-Chain Fv Analogue Produced in *Escherichia coli*," Proc. Natl. Acad. Sci. USA 85:5879-5883 (1988), which is hereby incorporated by reference in its entirety). These antibody fragments are obtained using conventional techniques known to those with skill in the art, and the fragments are evaluated for function in the same manner as are intact antibodies.

The term a first agent "in combination with" a second agent, as used herein, generally refers to a co-administration of a first agent and a second agent, which for example may be dissolved or intermixed in the same pharmaceutically acceptable carrier, or administration of a first agent, followed by the second agent, or administration of the second agent, followed by the first agent. The present disclosure, therefore, includes methods of combination therapeutic treatment and combination pharmaceutical compositions.

The term "Her2" as used herein, generally refers to the type I transmembrane protein, also known as c-erbB2, ErbB2 or Neu, belonging to the family of epidermal growth factor receptors. In the context of the present disclosure, the term "Her2" also encompasses homologues, variants and isoforms, including splice isoforms, of Her2. The term "Her2" further encompasses proteins having the sequence of one or more of a Her2 homologue, variant and isoform, as well as fragments of the sequences, provided that the variant proteins (including isoforms), homologous proteins and/or fragments are recognized by one or more Her2 specific antibodies, such as provided as Pertuzumab, Trastuzumab and Margetuximab. The Her2 may be a human Her2. The human Her2 gene is mapped to chromosomal location 17q12, and the genomic sequence of Her2 gene can be found in GenBank at NG 007503.1. In human, there are five Her2 isoforms: A, B, C, D, and E; the term "Her2" is used herein to refer collectively to all Her2 isoforms.

Dimers

In one aspect, the present disclosure provides use of an immune checkpoint inhibitor in combination with a Her2 inhibitor in the preparation of a medicament for treating tumor in a subject in need thereof, wherein said immune checkpoint inhibitor may be capable of specifically binding to PD-L1 and CTLA4.

In some embodiments, the immune checkpoint inhibitor may a dimer. The dimer may be formed by two polypeptide chains, with each of the two polypeptide chains comprising an antibody Fc subunit. For example, the dimer may consist of two polypeptide chains with each polypeptide chain comprising an antibody Fc subunit, and the antibody Fc subunit of one polypeptide chain may associate with the antibody Fc subunit of the other polypeptide chain to form the dimer. In an example, the two polypeptide chains of the dimer do not fuse (e.g., via a peptide linker or by a peptide bond) with each other to become one single polypeptide chain.

The dimer may comprise two or more immunoglobulin single variable domains (ISVDs). For example, one polypeptide chain of the dimer may comprise two or more ISVDs, and the other polypeptide chain of the dimer does not comprise any ISVD. In another example, each of the two polypeptide chains may comprise one or more ISVDs. In yet another example, each of the two polypeptide chains may comprise two or more ISVDs.

At least one of the ISVDs may be specific for PD-L1, and at least one of the ISVDs may be specific for CTLA4. For example, one polypeptide chain of the dimer may comprise one or more ISVDs specific for PD-L1 and one or more ISVDs specific for CTLA4, and the other polypeptide chain of the dimer does not comprise any ISVD. In another example, one polypeptide chain of the dimer may comprise one or more ISVDs specific for PD-L1, and the other polypeptide chain of the dimer may comprise one or more ISVDs specific for CTLA4. In another example, one polypeptide chain of the dimer may comprise one or more ISVDs specific for PD-L1 and one or more ISVDs specific for CTLA4, and the other polypeptide chain of the dimer may comprise one or more ISVDs specific for PD-L1 and/or one or more ISVDs specific for CTLA4.

The one or more ISVDs specific for PD-L1 may be identical or different. The one or more ISVDs specific for CTLA4 may be identical or different.

In some cases, the ISVD specific for PD-L1 does not comprise any antibody light chain CDR. In some cases, the ISVD specific for PD-L1 does not comprise any antibody light chain variable region. In some cases, the ISVD specific for PD-L1 does not comprise any antibody light chain or any fragment thereof. In some cases, the ISVD specific for PD-L1 comprises at least heavy chain CDR3. In some cases, the ISVD specific for PD-L1 comprises heavy chain CDR1. In some cases, the ISVD specific for PD-L1 comprises heavy chain CDR2. In some cases, the ISVD specific for PD-L1 comprises a heavy chain variable region. In some cases, the ISVD specific for PD-L1 is an anti-PD-L1 VHH. The ISVD specific for PD-L1 may be humanized.

In some cases, the ISVD specific for CTLA4 does not comprise any antibody light chain CDR. In some cases, the ISVD specific for CTLA4 does not comprise any antibody light chain variable region. In some cases, the ISVD specific for CTLA4 does not comprise any antibody light chain or any fragment thereof. In some cases, the ISVD specific for CTLA4 comprises at least heavy chain CDR3. In some cases, the ISVD specific for CTLA4 comprises heavy chain CDR1. In some cases, the ISVD specific for CTLA4 comprises heavy chain CDR2. In some cases, the ISVD specific for CTLA4 comprises a heavy chain variable region. In some cases, the ISVD specific for CTLA4 is an anti-CTLA4 VHH. The ISVD specific for CTLA4 may be humanized.

In some cases, at least one of the two polypeptide chains may comprise both an ISVD specific for PD-L1 and an ISVD specific for CTLA4. For example, one of the two polypeptide chains may comprise one or more ISVDs specific for PD-L1 and one or more ISVDs specific for CTLA4. In another example, each of the two polypeptide chains may comprise one or more ISVDs specific for PD-L1 and one or more ISVDs specific for CTLA4.

For one or both of the two polypeptide chains, the ISVD specific for PD-L1 may be fused to the ISVD specific for CTLA4, optionally via a linker. For example, in one or both of the two polypeptide chains, there may be one or more ISVDs specific for PD-L1, and one or more ISVDs specific for CTLA4. When two or more ISVDs specific for PD-L1 are present in a single polypeptide chain, they may be fused to each other (e.g., directly or via a peptide linker), and one or more of them may further be fused to one or more ISVDs specific for CTLA4. When two or more ISVDs specific for CTLA4 are present in a single polypeptide chain, they may be fused to each other (e.g., directly or via a peptide linker), and one or more of them may further be fused to one or more ISVDs specific for PD-L1. One or more linkers (e.g., peptide linker) may be present between any two ISVDs, for example, between two ISVDs specific for PD-L1, between two ISVDs specific for CTLA4, or between one ISVD specific from PD-L1 and one ISVD specific for CTLA4.

For one or both of the two polypeptide chains, the ISVD specific for PD-L1 may be fused to the ISVD specific for CTLA4, optionally via a linker; and the ISVD specific for CTLA4 may in turn be fused to the antibody Fc subunit, optionally via a linker. For example, in a single polypeptide chain, the ISVD specific for PD-L1 may be fused to the ISVD specific for CTLA4 directly (e.g., in frame) or via a linker, and the ISVD specific for CTLA4 may be fused to the antibody Fc subunit directly (e.g., in frame) or via a linker. When there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, and at least one ISVD specific for CTLA4 may be fused to the antibody Fc subunit directly (e.g., in frame) or via a linker. For example, for one or both of the two polypeptide chains, C terminus of the ISVD specific for PD-L1 may be fused to N terminus of the ISVD specific for CTLA4, optionally via a linker; and C terminus of the ISVD specific for CTLA4 may be fused to N terminus of the antibody Fc subunit, optionally via a linker. For example, in a single polypeptide chain, C terminus of one of the ISVDs specific for PD-L1 may be fused to N terminus of one of the ISVDs specific for CTLA4, either directly (e.g., in frame) or via a linker, and C terminus of one of the ISVDs specific for CTLA4 may be fused to N terminus of the antibody Fc subunit, either directly (e.g., in frame) or via a linker. In an example, when there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, however, C terminus of at least one ISVD specific for PD-L1 may be fused to N terminus of at least one ISVD specific for CTLA4, either directly (e.g., in frame) or via a linker, and C terminus of at least one ISVD specific for CTLA4 may be fused to N terminus of the antibody Fc subunit, either directly (e.g., in frame) or via a linker.

For one or both of the two polypeptide chains, the ISVD specific for CTLA4 may be fused to the ISVD specific for PD-L1, optionally via a linker; and the ISVD specific for PD-L1 may in turn be fused to the antibody Fc subunit, optionally via a linker. For example, in a single polypeptide chain, the ISVD specific for CTLA4 may be fused to the ISVD specific for PD-L1 directly (e.g., in frame) or via a linker, and the ISVD specific for PD-L1 may be fused to the antibody Fc subunit directly (e.g., in frame) or via a linker. When there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, and at least one ISVD specific for PD-L1 may be fused to the antibody Fc subunit directly (e.g., in frame) or via a linker. For example, for one or both of the two polypeptide chains, C terminus of the ISVD specific for CTLA4 may be fused to N terminus of the ISVD specific for PD-L1, optionally via a linker; and C terminus of the ISVD specific for PD-L1 may be fused to N terminus of the antibody Fc subunit, optionally via a linker. For example, in a single polypeptide chain, C terminus of one of the ISVDs specific for CTLA4 may be fused to N terminus of one of the ISVDs specific for PD-L1, either directly (e.g., in frame) or via a linker, and C terminus of one of the ISVDs specific for PD-L1 may be fused to N terminus of the antibody Fc subunit, either directly (e.g., in frame) or via a linker. In an example, when there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, however, C terminus of at least one ISVD specific for CTLA4 may be fused to N terminus of at least one ISVD specific for PD-L1, either directly (e.g., in frame) or via a linker, and C terminus of at least one ISVD specific for PD-L1 may be fused to N terminus of the antibody Fc subunit, either directly (e.g., in frame) or via a linker.

The linker (e.g., a peptide linker) employed in the present application (e.g., as comprised by the dimer of the present application) may be a synthetic amino acid sequence that connects or links two polypeptide sequences, e.g., via peptide bonds. For example, the peptide linker may comprise 1-10 amino acids (e.g., 1, 2, 3, 4, 5, 6, 7, 8, 9, 10 or more amino acids), 1-15 amino acids (e.g., 1-10, 11, 12, 13, 14 or 15 amino acids), 1-20 amino acids (e.g., 1-15, 16, 17, 18, 19, or 20 amino acids), 1-30 amino acids or more (e.g., 1-20, 21, 22, 23, 24, 25, 26, 27, 28, 29, 30 or more amino acids). For example, the peptide linker may comprise an amino acid sequence as set forth in any of SEQ ID NO: 33-34.

The antibody Fc subunit may be derived from an IgG Fc subunit. For example, the IgG may be selected from the group consisting of IgG1, IgG2, IgG3 and IgG4. In some embodiments, the IgG is a human IgG1, and the IgG Fc subunit is a human IgG1 Fc subunit. In some embodiments, the Fc subunit comprises an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 35, 38 and 39. For example, the Fc subunit may comprise an amino acid sequence having one or more (e.g., 1-2, 1-3, 1-4, 1-5, 1-6, 1-7, 1-8, 1-9, 1-10, or more) amino acid deletion, insertion and/or substitution in the amino acid sequence as set forth in any one of SEQ ID NO: 35, 38 and 39.

In some embodiments, the Fc subunit may be a variant of the IgG Fc subunit (e.g., a variant of the human IgG1 Fc subunit). For example, the variant may comprise one or more amino acid mutations that enhance or reduce the ADCC or CDC activities. As another example, the variant may comprise one or more amino acid mutations that affect FcRn binding activity and/or the half-life of the molecule comprising the variant. As yet another example, the variant may comprise one or more amino acid mutations that affect an interaction (e.g., association) between two or more Fc subunits (or Fc monomers) and/or increase or decrease an efficiency of Fc heterodimer formation, for example, the variant may comprise one or more of the amino acid substitutions as described in CN102558355A, CN103388013A, CN105820251A, or CN106883297A, each of which is incorporated by reference herein.

The ISVD specific for PD-L1 may be capable of specifically binding to human PD-L1. For example, the ISVD specific for PD-L1 may be capable of specifically binding to an epitope in an extracellular domain of the human PD-L1. Such epitopes are known in the art, for example, as shown by Gang Hao et al., *J. Mol. Recognit.* 2015; 28: 269-276, Zhang et al., Oncotarget. 2017 October; 08 (52): 90215-90224, and Zhang et al., Cell Discov. 2017 Mar. 7; 3:17004.

For example, the ISVD specific for PD-L1 may be capable of binding to N-terminal IgV domain of human PD-L1. The N-terminal IgV domain of human PD-L1 (including the signal peptide) may comprise an amino acid sequence as set forth in SEQ ID NO: 64. In the present disclosure, the ISVD specific for PD-L1 may be capable of binding to residues I54, Y56, E58, Q66 and/or R113 of human PD-L1 N-terminal IgV domain. In a specific embodiment, the ISVD specific for PD-L1 is capable of binding to residues I54, Y56, E58, Q66 and R113 of human PD-L1 N-terminal IgV domain (e.g., amino acid residue I54, Y56, E58, Q66 and/or R113 of SEQ ID NO: 64). The ISVD specific for PD-L1 may be capable of further binding to residues D61, N63, V68, M115, S117, Y123 and/or R125 of human PD-L1 N-terminal IgV domain (e.g., amino acid residue D61, N63, V68, M115, S117, Y123 and/or R125 of SEQ ID NO: 64). In some cases, the ISVD specific for PD-L1 may be capable of binding to residues I54, Y56, E58, Q66, R113, D61, N63, V68, M115, S117, Y123 and/or R125 of human PD-L1 N-terminal IgV domain (e.g., amino acid residue I54, Y56, E58, Q66, R113, D61, N63, V68, M115, S117, Y123 and/or R125 of SEQ ID NO: 64). In some cases, the ISVD specific for PD-L1 is capable of binding to a conformational epitope of human PD-L1 N-terminal IgV domain, the conformational epitope may comprise residues I54, Y56, E58, Q66 and/or R113 of the human PD-L1 N-terminal IgV domain (e.g., amino acid residue I54, Y56, E58, Q66 and/or R113 of SEQ ID NO: 64). In some cases, the ISVD specific for PD-L1 is capable of binding to a conformational epitope of human PD-L1 N-terminal IgV domain, the conformational epitope may comprise residue I54, Y56, E58, Q66, R113, D61, N63, V68, M115, S117, Y123 and/or R125 of the human PD-L1 N-terminal IgV domain (e.g., amino acid residue I54, Y56, E58, Q66, R113, D61, N63, V68, M115, S117, Y123 and/or R125 of SEQ ID NO: 64).

The ISVDs specific for PD-L1 of the present disclosure (e.g., PD-L1 ISVD-9 and the humanized variants thereof) bind to the N-terminal IgV domain of human PD-L1. Taking PD-L1 ISVD-9 as an example, the residue Phe101 of PD-L1 ISVD-9 (SEQ ID NO: 6) interacts with Tyr56 of human PD-L1 N-terminal IgV domain, and when the Tyr56 of human PD-L1 N-terminal IgV domain was substituted by Ala, the binding affinity between PD-L1 ISVD-9 and PD-L1 was reduced by over 200 folds. When the Ile54 of human PD-L1 N-terminal IgV domain was substituted by Ala, the binding affinity between PD-L1 ISVD-9 and PD-L1 was reduced by about 40 folds. The residue Asp99 of PD-L1 ISVD-9 (SEQ ID NO: 6) interacts with Arg113 of human PD-L1 N-terminal IgV domain, and when the Arg113 of human PD-L1 N-terminal IgV domain was substituted by Ala, the binding affinity between PD-L1 ISVD-9 and PD-L1 was reduced by about 90 folds. The residue Ser100 of PD-L1 ISVD-9 (SEQ ID NO: 6) interacts with Glu58 of human PD-L1 N-terminal IgV domain, and when the Glu58 of human PD-L1 N-terminal IgV domain was substituted by Ala, the binding affinity between PD-L1 ISVD-9 and PD-L1 was reduced by about 25 folds. The residue Thr105 of PD-L1 ISVD-9 (SEQ ID NO: 6) interacts with Gln66 of human PD-L1 N-terminal IgV domain, and when the Gln66 of human PD-L1 N-terminal IgV domain was substituted by Ala, the binding affinity between PD-L1 ISVD-9 and PD-L1 was reduced by about 82 folds. In addition, residues D61, N63, V68, M115, S117, Y123 and R125 of human PD-L1 N-terminal IgV domain may be involved in the interaction between PD-L1 ISVD-9 and human PD-L1, substituting these residues with Ala resulted in a reduction of binding affinity by about 2-10 folds. These results are summarized in Table 2 below.

TABLE 2

| Effects of Substitutions in human PD-L1 for binding of PD-L1 ISVD-9 | | |
| --- | --- | --- |
| Human PD-L1 mutation | $K_D$ (M) | $K_{D, mutant}/K_{D, WT}$ |
| WT | 5.92E-09 | 1 |
| I54A | 2.42E-07 | 40.9 |
| Y56A | 1.24E-06 | 209.5 |
| E58A | 1.49E-07 | 25.2 |
| D61A | 1.99E-08 | 3.4 |
| N63A | 2.30E-08 | 3.9 |
| Q66A | 4.88E-07 | 82.4 |
| V68A | 2.76E-08 | 4.7 |
| R113A | 5.34E-07 | 90.2 |
| M115A | 5.51E-08 | 9.3 |
| S117A | 1.26E-08 | 2.1 |
| Y123A | 4.24E-08 | 7.2 |
| R125A | 2.97E-08 | 5.0 |

The ISVD specific for PD-L1 may be capable of blocking binding of PD-L1 to PD1. In some cases, the ISVD specific for PD-L1 may be capable of blocking binding of PD-L1 to CD80.

The ISVD specific for PD-L1 may cross-compete for binding to PD-L1 with a reference anti-PD-L1 antibody.

The reference anti-PD-L1 antibody may comprise a heavy chain CDR3. The heavy chain CDR3 may comprise an amino acid sequence as set forth in DSFX$_1$X$_2$PTCX$_3$X$_4$X$_5$X$_6$SSGAFQY (SEQ ID NO: 1), wherein X$_1$ may be E or G; X2 may be D or Y; X3 may be T or P; X4 may be L or G; X5 may be V or P; and X6 may be T or A. In some cases, the reference anti-PD-L1 antibody may comprise a heavy chain CDR3 comprising an amino acid sequence as set forth in any one of SEQ ID NO: 5 and 9. The reference anti-PD-L1 antibody may also comprise a heavy chain CDR1. The heavy chain CDR1 may comprise an amino acid sequence as set forth in GX$_1$X$_2$X$_3$X$_4$X$_5$RCMA (SEQ ID NO: 2), wherein X$_1$ may be K or N; X2 may be M or I; X3 may be S or I; X4 may be S or R; and X5 may be R or V. For example, the reference anti-PD-L1 antibody may comprise a heavy chain CDR1 comprising an amino acid sequence as set forth in any one of SEQ ID NO: 3 and 7. In some cases, the reference anti-PD-L1 antibody may comprise a heavy chain CDR2. The heavy chain CDR2 may comprise an amino acid sequence as set forth in any one of SEQ ID NO: 4, 8 and 11. In some cases, the reference anti-PD-L1 antibody is an ISVD specific for PD-L1, such as an anti-PD-L1 VHH. The reference anti-PD-L1 antibody may comprise a heavy chain variable domain. The reference anti-PD-L1 antibody may comprise a heavy chain variable domain comprising an amino acid sequence as set forth in any one of SEQ ID NO: 6, 10, 12, 13, 14 and 15. For example, the heavy chain variable domain may comprise an amino acid sequence as set forth in SEQ ID NO: 6.

In the present disclosure, the ISVD specific for PD-L1 (e.g., as comprised in the dimer of the present disclosure) may comprise a heavy chain CDR3. The heavy chain CDR3 may comprise an amino acid sequence as set forth in DSFX$_1$X$_2$PTCX$_3$X$_4$X$_5$X$_6$SSGAFQY (SEQ ID NO: 1), wherein X$_1$ may be E or G; X2 may be D or Y; X3 may be T or P; X4 may be L or G; X5 may be V or P; and X6 may be T or A. For example, the ISVD specific for PD-L1 may comprise a heavy chain CDR3 comprising an amino acid sequence as set forth in any one of SEQ ID NO: 5 and 9.

For example, the ISVD specific for PD-L1 may comprise a heavy chain CDR3 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 5 and 9. In some cases, the heavy chain CDR3 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 5 and 9.

In the present disclosure, the ISVD specific for PD-L1 (e.g., as comprised in the dimer of the present disclosure) may also comprise a heavy chain CDR1. The heavy chain CDR1 may comprise an amino acid sequence as set forth in GX$_1$X$_2$X$_3$X$_4$X$_5$RCMA (SEQ ID NO: 2), wherein X$_1$ may be K or N; X$_2$ may be M or I; X$_3$ may be S or I; X$_4$ may be S or R; and X$_5$ may be R or V. For example, the ISVD specific for PD-L1 may comprise a heavy chain CDR1 comprising an amino acid sequence as set forth in any one of SEQ ID NO: 3 and 7.

For example, the ISVD specific for PD-L1 may comprise a heavy chain CDR1 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 3 and 7. In some cases, the heavy chain CDR1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 3 and 7.

In the present disclosure, the ISVD specific for PD-L1 (e.g., as comprised in the dimer of the present disclosure) may further comprise a heavy chain CDR2. The heavy chain CDR2 may comprise any suitable amino acid sequence. In some case, the ISVD specific for PD-L1 may comprise a heavy chain CDR2 comprising an amino acid sequence as set forth in any one of SEQ ID NO: 4, 8 and 11.

For example, the ISVD specific for PD-L1 may comprise a heavy chain CDR2 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 4, 8 and 11. In some cases, the heavy chain CDR2 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 4, 8 and 11.

In the present disclosure, the ISVD specific for PD-L1 (as comprised in the dimer of the present disclosure) may comprise a heavy chain variable domain. The ISVD specific for PD-L1 may comprise a heavy chain variable domain comprising an amino acid sequence as set forth in any one of SEQ ID NO: 6, 10, 12, 13, 14 and 15. For example, the heavy chain variable domain may comprise an amino acid sequence as set forth in SEQ ID NO: 6.

For example, the ISVD specific for PD-L1 may comprise a heavy chain variable domain comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 6, 10, 12, 13, 14 and 15. In some cases, the ISVD specific for PD-L1 may comprise a heavy chain variable domain comprising an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 6, 10, 12, 13, 14 and 15.

In the present disclosure, the ISVD specific for PD-L1 may comprise an amino acid sequence as set forth in any one of SEQ ID NO: 6, 10, 12, 13, 14 and 15. For example, the ISVD specific for PD-L1 (as comprised in the dimer of the present disclosure) may comprise an amino acid sequence as set forth in SEQ ID NO: 6. For example, the ISVD specific for PD-L1 may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 6, 10, 12, 13, 14 and 15. In some cases, the ISVD specific for PD-L1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 6, 10, 12, 13, 14 and 15.

In some cases, the ISVD specific for PD-L1 comprises or consists of a heavy chain variable domain (VH or VHH).

For example, the ISVD specific for PD-L1 may be selected from PD-L1 ISVD-9, PD-L1 ISVD-6, PD-L1 ISVD-m3, PD-L1 ISVD-4, PD-L1 ISVD-11 and PD-L1 ISVD-13.

The ISVD specific for CTLA4 may be capable of specifically binding to human CTLA4. For example, the ISVD specific for CTLA4 may be capable of specifically binding to an epitope in an extracellular domain of the human CTLA4, such an epitope may include those described in CN107400166A, and those described by Udupi A. Ramagopal, et. al., *PNAS* 2017 May, 114 (21)

The ISVD specific for CTLA4 may be capable of blocking binding of CTLA4 to CD80. In some cases, the ISVD specific for CTLA4 may be capable of blocking binding of CTLA4 to CD86. In some cases, the ISVD specific for CTLA4 may be humanized.

The ISVD specific for CTLA4 may cross-compete for binding to CTLA4 with a reference anti-CTLA4 antibody.

The reference anti-CTLA4 antibody may comprise a heavy chain CDR3. The heavy chain CDR3 may comprise an amino acid sequence as set forth in SEQ ID NO: 19. The reference anti-CTLA4 antibody may also comprise a heavy chain CDR1. The heavy chain CDR1 may comprise an amino acid sequence as set forth in SEQ ID NO: 17. In some cases, the reference anti-CTLA4 antibody may comprise a heavy chain CDR2. The heavy chain CDR2 may comprise an amino acid sequence as set forth in $AIX_1X_2GGGSTYYADSVKG$ (SEQ ID NO: 16), wherein $X_1$ may be Y or S; and $X_2$ may be I or L. For example, the heavy chain CDR2 may comprise an amino acid sequence as set forth in any one of SEQ ID NO: 18, 21 and 23. In some cases, the reference anti-CTLA4 antibody is an ISVD specific for CTLA4, such as an anti-CTLA4 VHH. The reference anti-CTLA4 antibody may comprise a heavy chain variable domain. The reference anti-CTLA4 antibody may comprise a heavy chain variable domain comprising an amino acid sequence as set forth in any one of SEQ ID NO: 20, 22, and 24-32. For example, the heavy chain variable domain may comprise an amino acid sequence as set forth in SEQ ID NO: 20.

In the present disclosure, the ISVD specific for CTLA4 (e.g., as comprised in the dimer of the present disclosure) may comprise a heavy chain CDR3. The heavy chain CDR3 may comprise an amino acid sequence as set forth in SEQ ID NO: 19.

In some cases, the ISVD specific for CTLA4 may comprise a heavy chain CDR3 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in SEQ ID NO: 19. In some cases, the heavy chain CDR3 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in SEQ ID NO: 19.

In the present disclosure, the ISVD specific for CTLA4 (e.g., as comprised in the dimer of the present disclosure)

may also comprise a heavy chain CDR1. The heavy chain CDR1 may comprise an amino acid sequence as set forth in SEQ ID NO: 17.

In some cases, the ISVD specific for CTLA4 may comprise a heavy chain CDR1 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in SEQ ID NO: 17. In some cases, the heavy chain CDR1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in SEQ ID NOs: 17.

In the present disclosure, the ISVD specific for CTLA4 (e.g., as comprised in the dimer of the present disclosure) may further comprise a heavy chain CDR2. The heavy chain CDR2 may comprise an amino acid sequence as set forth in AIX$_1$X$_2$GGGSTYYADSVKG (SEQ ID NO: 16), wherein X$_1$ may be Y or S; and X2 may be I or L. In some case, the ISVD specific for CTLA4 may comprise a heavy chain CDR2 comprising an amino acid sequence as set forth in any one of SEQ ID NO: 18, 21 and 23.

For example, the ISVD specific for CTLA4 may comprise a heavy chain CDR2 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 18, 21 and 23. In some cases, the heavy chain CDR2 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 18, 21 and 23.

In the present disclosure, the ISVD specific for CTLA4 (as comprised in the dimer of the present disclosure) may comprise a heavy chain variable domain. The ISVD specific for CTLA4 may comprise a heavy chain variable domain comprising an amino acid sequence as set forth in any one of SEQ ID NO: 20, 22, and 24-32. For example, the heavy chain variable domain may comprise an amino acid sequence as set forth in SEQ ID NO: 20.

For example, the ISVD specific for CTLA4 may comprise a heavy chain variable domain comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 20, 22, and 24-32. In some cases, the ISVD specific for CTLA4 may comprise a heavy chain variable domain comprising an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 20, 22, and 24-32.

In the present disclosure, the ISVD specific for CTLA4 may comprise an amino acid sequence as set forth in any one of SEQ ID NO: 20, 22, and 24-32. For example, the ISVD specific for CTLA4 (as comprised in the dimer of the present disclosure) may comprise an amino acid sequence as set forth in SEQ ID NO: 20.

For example, the ISVD specific for CTLA4 may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 20, 22, and 24-32. In some cases, the ISVD specific for CTLA4 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 20, 22, and 24-32.

In some cases, the ISVD specific for CTLA4 comprises or consists of a heavy chain variable domain (VH or VHH).

For example, the ISVD specific for CTLA4 may be selected from CTLA4 ISVD-34, CTLA4 ISVD-C1, CTLA4 ISVD-13, CTLA4 ISVD-26, CTLA4 ISVD-27, CTLA4 ISVD-28, CTLA4 ISVD-29, CTLA4 ISVD-30, CTLA4 ISVD-31, CTLA4 ISVD-32, and CTLA4 ISVD-33.

For example, the dimer of the present application may comprise or consist of two polypeptide chains. The amino acid sequence of the two polypeptide chains may be identical or different. In some cases, the dimer of the present disclosure may be homodimer.

In the present disclosure one or both of the two polypeptide chains of the dimer may comprise an amino acid sequence as set forth in SEQ ID NO: 40.

In specific examples, one or both of the two polypeptide chains of the dimer may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 40-43, 46, 48 and 50. In some cases, one or both of the two polypeptide chains of the dimer may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 40-43, 46, 48 and 50.

In an example, an ISVD specific for PD-L1 may be fused (directly or indirectly, e.g., via a linker, such as a peptide linker) to an N-terminal amino acid of an ISVD specific for CTLA4 to form a bi-specific binding moiety. Then, one such bi-specific binding moiety may be fused (directly or indirectly, e.g., via a linker, such as a peptide linker) to an N-terminal amino acid of one Fc subunit of the present disclosure to provide one polypeptide chain of the dimer. Then, another such bi-specific binding moiety may be fused (directly or indirectly, e.g., via a linker, such as a peptide linker) to an N-terminal amino acid of another Fc subunit of the present disclosure to provide the other polypeptide chain of the dimer. The two Fc subunits of the two polypeptide chains may associate with each other (e.g., via non-covalent interactions and/or disulfide bond or other covalent bond, in some cases, such covalent bond is not a peptide bond) to form the dimer. The two bi-specific binding moieties may be identical or different. The two Fc subunits may be identical or different.

In some embodiments, the dimer is a proteinaceous homodimer comprising two identical polypeptide chains, with each polypeptide chain comprising one of the bispecific binding moiety fused to one of the Fc subunits, and the two Fc subunits associate with each other to form the proteinaceous homodimer. The two Fc subunits may associate with each other via non-covalent interactions and/or disulfide bond or other covalent bond, in some cases, such covalent bond is not a peptide bond.

A and B of FIG. 1 provide examples of the dimer of the present disclosure, wherein 1 indicates the ISVD specific for PD-L1, 2 indicates the ISVD specific for CTLA4, 3 indicates the Fc domain comprising the Fc subunits, and 4 indicates the bi-specific binding moiety.

The dimer of the present disclosure may be capable of competing with CD80 and/or CD86 for binding to CTLA4. For example, the competition may be examined in an in vitro experiment using CTLA4 expressing cell lines, such as a CTLA4 expressing HEK293 cell line. As another example, the competition may be examined in an ELISA essay, such as a competition ELISA assay.

The dimer of the present disclosure may be capable of competing with PD1 and/or CD80 for binding to PD-L1. For example, the competition may be examined in an in vitro experiment using PD-L1 expressing cell lines, such as a PD-L1 expressing A375 cell line. As another example, the competition may be examined in an ELISA essay, such as a competition ELISA assay.

The dimer of the present disclosure may be capable of blocking binding of PD-L1 to PD-1. In some cases, the dimer of the present disclosure may be capable of blocking binding of PD-L1 to CD80. In some cases, the dimer of the present disclosure may be capable of blocking binding of CTLA4 to CD80. In some cases, the dimer of the present disclosure may be capable of blocking binding of CTLA4 to CD86.

The dimer of the present disclosure may bind to CTLA4 with a $K_D$ of a value no more than about $1\times10^{-6}$ M, for example, no more than about $1\times10^{-7}$ M, no more than about $1\times10^{-8}$ M, no more than about $0.5\times10^{-8}$ M, no more than about $1\times10^{-9}$ M, no more than about $1\times10^{-10}$ M or lower.

The dimer of the present disclosure may bind to PD-L1 with a $K_D$ of a value no more than about $1\times10^{-6}$ M, for example, no more than about $1\times10^{-7}$ M, no more than about $1\times10^{-8}$ M, no more than about $0.5\times10^{-8}$ M, no more than about $1\times10^{-9}$ M, no more than about $1\times10^{-10}$ M or lower.

The dimer of the present disclosure may be capable of stimulating the secretion of an immunoregulator (e.g., IL-2) by immune cells (e.g., PBMC cells).

For example, the dimer of the present disclosure may be selected from aPDL1.9-aCTLA4.34-Fc, aPDL1.9-L-aCTLA4.34-Fc, aCTLA4.34-aPDL1.9-Fc, aCTLA4.34-L-aPDL1.9-Fc, aPDL1.6-aCTLA4.34-Fc, aPDL1.m3-aCTLA4.34-Fc and aPDL1.9-aCTLA4.13-Fc.

For example, the dimer of the present disclosure may comprise the ISVD specific for CTLA4 and the ISVD specific for PDL1. The ISVD specific for PD-L1 may comprise the CDR3 comprising an amino acid sequence as set forth in SEQ ID NO. 5, the CDR2 comprising an amino acid sequence as set forth in SEQ ID NO. 4, the CDR1 comprising an amino acid sequence as set forth in SEQ ID NO. 3. And the ISVD specific for CTLA4 may comprise the CDR3 comprising an amino acid sequence as set forth in SEQ ID NO. 19, the CDR2 comprising an amino acid sequence as set forth in SEQ ID NO. 18, and the CDR1 comprising an amino acid sequence as set forth in SEQ ID NO. 17. And the dimer of the present disclosure may comprise the ISVD specific for PD-L1 comprising an amino acid sequence as set forth in SEQ ID NO.6, and the ISVD specific for CLTA4 comprising an amino acid sequence as set forth in SEQ ID NO. 20. For example, the dimer of the present disclosure may comprise an amino acid sequence of SEQ ID NO.40.

And the dimer of the present disclosure may be named as KN046.

Her2 Inhibitor

In the present disclosure, the Her2 inhibitor may be a Her2 antibody or an antigen binding portion thereof and/or a conjugate thereof.

In some embodiments, the Her2 inhibitor may be a bispecific antibody or the antigen binding portion thereof, wherein the bispecific antibody or the antigen binding portion thereof may have a common light chain, and wherein said common light chain refers to two light chains having the same sequence.

In some embodiments, heavy chains of the bispecific antibody or the antigen binding portion thereof may be capable of correctly assembling with said light chains respectively under physiological conditions or during in vitro protein expression.

The common light chain may be engineered from two original monoclonal antibodies (known monoclonal antibodies) that differed from at least the light chain sequence of one of the two original monoclonal antibodies. In some embodiments, the common light chain may be identical to or modified on the basis of one of the two original monoclonal antibodies (e.g., amino acid sequence modification), and the purpose of the modification is to maintain affinity with the respective antigen or epitope. In some embodiments, the amino acid sequence modification may comprise a mutation, deletion or addition of an amino acid, such as a mutation, deletion or addition of no more than 3 amino acids, preferably no more than 2 amino acids, more preferably no more than 1 amino acid.

In the present application, light chain sequences (especially variable region sequences) of two monoclonal antibodies (namely original antibodies) against different antigens or antigen epitopes may be analyzed and verified to obtain a common light chain capable of assembling with the heavy chains of the two monoclonal antibodies. After assembling with the heavy chains, the common light chain still can specifically bind to the antigens or antigen epitopes directed to by the original monoclonal antibodies.

In the present application, light chain sequences (especially variable region sequences) of two monoclonal antibodies (namely original antibodies) against different antigens or antigen epitopes may be analyzed and verified to obtain a common light chain capable of assembling with the heavy chains of the two monoclonal antibodies. After assembling with the heavy chains, the common light chain still can specifically bind to the antigens or antigen epitopes directed to by the original monoclonal antibodies.

In the present application, the common light chain can be used for expressing the bispecific antibody, and can also be used for expressing a mixture comprising two antibodies; when the bispecific antibody is expressed, the antibody comprises a light chain and a heavy chain which are capable of binding to a first antigen, and a light chain and a heavy chain which may be capable of binding to a second antigen, wherein the sequences of the two light chain are completely the same, namely, is a common light chain.

In the present application, light chain constant regions of the two original antibodies may be of κ type or λ type; the K-type light chain constant region comprises various allotypes, such as Km1, Km2 and Km3; the k-type light chain constant region comprises various allotypes, such as CL1, CL2, CL3, CL6 and CL7.

It is known in the art that the variable region may be crucial for specific binding between the antigen and the antibody, thus, during the process of modifying or obtaining an antibody, the selection and modification of the variable region sequences are critical. Hence, in the present application, in order to obtain the bispecific antibody or the antibody mixture having the common light chain, the variable regions of the common light chain may need to be obtained firstly. After selecting the light chain variable region of one original monoclonal antibody or a mutant thereof as the variable region of the common light chain according to the method discussed above, the constant region of the common light chain is determined. Normally, the common light chain constant region may be determined to be the light chain constant region of the monoclonal antibody from which the common light chain variable region is derived. In some cases, the light chain constant region of the other monoclonal antibody may be determined to be the common light chain constant region. When necessary, the original light chain constant region may be modified (e.g., by addition, deletion or mutation of amino acid, etc.) based on knowledge known in the art to obtain a more suitable constant region of the common light chain, for example, after modification, the common light chain constant region has a better ADCC, CDC, endocytosis, stability, immunogenicity or half-life etc.

In the present application, the heavy chain type of the two original antibodies may be the same or different, preferably, the heavy chains are of the same type. In one embodiment, when preparing the bispecific antibody and the antibody mixture, the sequences of the variable region and the CH1 domain of the heavy chain are unchanged comparing to that of the original antibodies.

In the present application, two arms of the bispecific antibody or the antibodies of the mixture containing two antibodies may be are both derived from two original monoclonal antibodies. When preparing the bispecific antibody or the antibody mixture, only sequences of the light chain variable region would be changed to obtain the common light chain, while sequences of the heavy chain variable region may not need to be changed. In other words, in the bispecific antibody or the antibody mixture prepared, sequences of the antibody heavy chain variable regions may be the same as that of the original antibody, but sequences of at least one light chain variable region shall be different from that of the original antibody.

In the present application, the two original monoclonal antibodies may be selected according to different demands or objectives, for example, the selected two monoclonal antibodies can be against different antigen epitopes of the same antigen; alternatively, one of selected antibodies may bind to a related antigen on the surface of a tumor cell while the other antibody may trigger an immunologic effector cell so as to further kill a cell.

In the present application, when preparing the bispecific antibody, the heavy chain (such as an Fc fragment) may be modified based on technologies known in the art to facilitate formation of the heterodimer protein during antibody expression.

In the present application, when preparing the antibody mixture, the heavy chain (such as an Fc fragment), may be modified based on technologies known in the art so as to facilitate formation of the homodimer protein during antibody expression.

In the present application, technologies for modifying an Fc fragment of the antibody heavy chain to facilitate formation of the homodimer protein or the heterodimer protein are known in the art, for example, reference may be made to, Ridgway, Presta et al. 1996, Carter 2001, Patent CN 102558355A and Patent CN 103388013A.

In the present application, technologies of fusing polypeptides recognizing different antigen epitopes may include but is not limited to, for example, a heterodimer Fc fusing technology as shown in the examples, it can also be an "Fab" technology, see FIG. 2.

In the present application, the heterodimer Fc fusing technology used in the present application may be based on a "knob"-"hole" model, and it may also be based on a "charge repulsion model", but is not limited to these two models.

In some embodiments, the heavy chain Fc segment of the bispecific antibody or antigen binding portion thereof may be engineered to be more advantageous for the formation of a heterodimeric protein.

In some embodiments, the two original monoclonal antibodies may be Pertuzumab and Trastuzumab.

In some embodiments, the common light chain may be capable of assembling with a heavy chain of Pertuzumab and a heavy chain of Trastuzumab, respectively.

In some embodiments, the common light chain may be selected from the light chain of Pertuzumab or Trastuzumab or a mutant thereof. In some embodiments, the heavy chain (including the variable region and the constant region) of the bispecific antibody or antigen binding portion thereof may be identical to the two original monoclonal antibodies or may be modified to facilitate formation. Heterodimeric protein; the modification is, for example, engineering the heavy chain Fc segment to facilitate formation of a heterodimeric protein.

In some embodiments, the sequence of the variable region of the common light chain may comprise a sequence selected from amino acids 1 to 107 of SEQ ID NO: 65 to SEQ ID NO: 70. In some embodiments, the sequence of the light chain constant region may comprise the sequence of amino acids 108 to 214 of SEQ ID NO: 65. For example, the variable region of the common light chain of the Her2 inhibitor may be the light chain variable region of Trastuzumab.

In one embodiment, heavy chain variable regions of the antibody or antigen binding portion thereof may be a heavy chain variable region of Pertuzumab and a heavy chain variable region of Trastuzumab, respectively; for example, the heavy chain variable regions may comprise sequences as set forth in SEQ ID NO: 87 and SEQ ID NO: 88, respectively.

In some embodiment, a sequence of a variable region of the two heavy chains may comprise a sequence as set forth in SEQ ID NO: 89 and SEQ ID NO: 90, respectively.

In one embodiment, two heavy chains thereof may comprise a sequence as set forth in SEQ ID NO: 83 and SEQ ID NO: 84, respectively.

For example, the common light chain of the Her2 inhibitor may comprise a sequence of amino acid as set forth in SEQ ID NO: 65; the heavy chain variable regions may comprise sequences as set forth in SEQ ID NO: 87 and SEQ ID NO: 88, respectively, and the variable region of the two heavy chains may comprise a sequence of the amino acid sequence as set forth in SEQ ID NO: 89 and SEQ ID NO: 90, respectively. The two heavy chains thereof may comprise a sequence as set forth in SEQ ID NO: 83 and SEQ ID NO: 84, respectively.

And the Her2 inhibitor of the present disclosure may be named as KN026.

Pharmaceutical Composition and Use

In the present disclosure, provided a pharmaceutical composition comprising an effective amount of said immune checkpoint inhibitor and an effective amount of the Her2 inhibitor of the present disclosure and optionally a pharmaceutically acceptable excipient.

In some embodiments, the term "an effective amount" refers to the amount of the immune checkpoint inhibitor or the Her2 inhibitor of the present disclosure that, when administered to a subject, is effective to at least partially alleviating, inhibiting, preventing and/or ameliorating a condition, or a disorder or a disease. An effective amount of the pharmaceutical composition may be administered for prevention or treatment of disease. The appropriate dosage of the pharmaceutical composition may be determined based on the type of disease to be treated, the type of the pharmaceutical composition, the severity and course of the disease, the clinical condition of the individual, the individual's clinical history and response to the treatment, and the discretion of the attending physician.

In another aspect, the present disclosure provides a use of the pharmaceutical composition in present disclosure in the preparation of a medicament for treating tumor in a subject.

In another aspect, the present disclosure provides the pharmaceutical composition in present disclosure, for a use in treating tumor in a subject.

In another aspect, the present disclosure provides a method of treating tumor in a subject, comprising the pharmaceutical composition in present disclosure.

In some embodiments, the treatment results in a sustained response in the individual after cessation of the treatment. The medicaments described herein may find use in treating conditions where enhanced immunogenicity is desired such as increasing tumor immunogenicity for the treatment of tumor. The pharmaceutical composition may also enhance immune function in an individual having tumor by administering to the individual an effective amount of the immune checkpoint and the Her2 inhibitor.

In the present disclosure, said tumor may be selected from a group consisting of a solid tumor and a hematologic tumor.

In the present disclosure, said tumor may be selected from a group consisting of NSCLC, breast cancer, gastric cancer, gastroesophageal junction adenocarcinoma, esophageal adenocarcinoma, cervical, ovarian, endometrial, biliary tract, colorectal and urothelial cancer.

In the present disclosure, said tumor may be selected from a group consisting of Her2 aberrated solid tumor and Her2-positive cancer.

In the present disclosure, said subject may have been administrated anti-Her2 antibody and/or anti-PD1 agent.

For example, said anti-Her2 antibody may comprise trastuzumab.

For example, said subject may have been administrated chemotherapy.

In some embodiments, said chemotherapy may comprise a first line chemotherapy and/or a second line chemotherapy. For example, said second line chemotherapy may comprise paclitaxel plus ramucirumab, paclitaxel, docetaxel and/or irinotecan monotherapy.

In present disclosure, said chemotherapy may refer to any treatment against said tumor by chemical agents. Said chemical agent may kill tumor cells, shrink a tumor and/or relieve signs and symptoms of cancer. For example, said chemotherapy may comprise a first line chemotherapy and/or a second line chemotherapy.

In present disclosure, said first line chemotherapy may refer to a chemotherapy regimen or regimens that are generally accepted by the medical establishment for initial treatment of a given type and stage of cancer. For example, said first line chemotherapy may comprise a platinum-based chemotherapy. In some embodiments, said first line platinum-based chemotherapy may comprise chemotherapy with a platinum (P) compound (cisplatin or carboplatin).

In present disclosure, said second line chemotherapy may refer to those tried when the first ones do not work adequately. For example, said second line chemotherapy may comprise paclitaxel plus ramucirumab, paclitaxel, docetaxel and/or irinotecan monotherapy.

In present disclosure, said Her2-positive cancer may refer to a cancer having tumor cells which have expression levels of Her2 higher than normal.

In present disclosure, said Her2 aberrated solid tumor may refer to solid tumor having Her2 aberrations, for example, said solid tumor may have abnormal Her2 gene amplification, Her2 gene mutations, and Her2 protein overexpression.

In present disclosure, said anti-PD1 agent may refer to any agent binds to PD1 and/or blocks the binding between PD1 and PD-L1. For example, said anti-PD1 agent may comprise an anti-PD1 antibody.

In present disclosure, said tumor may comprise said Her2 aberrated solid tumor, with which the subject thereof failed in previous trastuzumab therapy.

In present disclosure, said tumor may comprise Her2-positive GC (gastric cancer) and Her2-positive GEJ (gastroesophageal junction adenocarcinoma) with which the subject thereof failed in at least one prior line of systemic therapy (for example, failed in prior trastuzumab therapy, or failed in both trastuzumab and anti-PD-1 agent therapy).

The pharmaceutical composition may be administered by the same route of administration or by different routes of administration. In some embodiments, the pharmaceutical composition may be administered intravenously, intramuscularly, subcutaneously, topically, orally, transdermally, intraperitoneally, intraorbitally, by implantation, by inhalation, intrathecally, intraventricularly, or intranasally. In some embodiments, said Her2 inhibitor may be administered intravenously, intramuscularly, subcutaneously, topically, orally, transdermally, intraperitoneally, intraorbitally, by implantation, by inhalation, intrathecally, intraventricularly, or intranasally. In some embodiments, said immune checkpoint inhibitor may be administered intravenously, intramuscularly, subcutaneously, topically, orally, transdermally, intraperitoneally, intraorbitally, by implantation, by inhalation, intrathecally, intraventricularly, or intranasally.

In present disclosure, said Her2 inhibitor may be administrated by intravenous administration.

In present disclosure, said immune checkpoint inhibitor may be administrated by intravenous administration.

As a general proposition, an effective amount of the immune checkpoint inhibitor and an effective amount of the Her2 inhibitor administered to a subject may be in the range of about 0.01 to about 100 mg/kg of subject body weight whether by one or more administrations.

In some embodiments, the Her2 inhibitor may be used is about 0.01 to about 100 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 100 mg/kg, about 5 mg/kg to about 100 mg/kg, about 10 mg/kg to about 100 mg/kg administered, or about 20 mg/kg to about 100 mg/kg administered, for example. In some embodiments, said Her2 inhibitor may be administered at about 20 to about 30 mg/kg.

In some embodiments, the immune checkpoint inhibitor may be used is about 0.01 to about 100 mg/kg, about 0.01 mg/kg to about 80 mg/kg, about 0.01 mg/kg to about 60 mg/kg, about 0.01 mg/kg to about 40 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, about 0.01 mg/kg to about 4 mg/kg, or about 0.01 mg/kg to about 3 mg/kg administered. In some embodiments, said immune checkpoint inhibitor may be administered at about 1 to about 5 mg/kg. For example, said immune checkpoint inhibitor may be administered at dose of about 3 mg/kg to about 5 mg/kg.

For example, said immune checkpoint inhibitor may be administrated at dose of about 3 mg/kg and said Her2 inhibitor may be administered at about 20 mg/kg or 30 mg/kg. For example, said immune checkpoint inhibitor may be administrated at dose of about 5 mg/kg and said Her2 inhibitor may be administered at about 20 mg/kg.

The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

The pharmaceutical composition may be used is about 0.01 to about 100 mg/kg, about 0.01 mg/kg to about 80 mg/kg, about 0.01 mg/kg to about 60 mg/kg, about 0.01 mg/kg to about 40 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, about 0.01 mg/kg to about 4 mg/kg, or about 0.01 mg/kg to about 3 mg/kg administered.

The pharmaceutical composition may be administrated to a subject at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the Her2 inhibitor may be administrated to a subject at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the immune checkpoint may be administrated to a subject at a dosing frequency of about four times a week, twice a week, once a week, once every two weeks, once every three weeks, once every four weeks, once every five weeks, once every six weeks, once every eight weeks, once every nine weeks, once every twelve weeks, or less frequently so long as a therapeutic response is achieved.

In present disclosure, said Her2 inhibitor may be administrated once every two weeks or once every three weeks or with a loading dose. In present disclosure, said immune checkpoint inhibitor may be administrated once every two weeks or once every three weeks.

For example, said immune checkpoint inhibitor may be administrated once every two weeks and said Her2 inhibitor may be administrated once every two weeks. For example, said immune checkpoint inhibitor may be administrated once every three weeks and said Her2 inhibitor may be administrated once every two weeks. For example, said immune checkpoint inhibitor may be administrated once every three weeks and said Her2 inhibitor may be administrated once every three weeks.

In the present disclosure, provided a use of the immune checkpoint inhibitor in combination with the Her2 inhibitor in the preparation of a medicament for treating tumor in a subject in need thereof. The use of the term "in combination with" does not restrict the order in which therapies are administered to a subject in need thereof. The immune checkpoint inhibitor can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly or concurrently with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the Her2 inhibitor to a subject in need thereof.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Clinical Study of the Her2 Inhibitor in Combination with the Dimer of the Present Disclosure in Subjects with Her2 Positive Tumor This is an open-label, phase Ib, multicenter clinic study. The purpose of this study is to evaluate the safety and efficacy of the Her2 inhibitor in combination with the dimer of the present disclosure in subjects with Her2 positive tumor.

The study will include a dose escalation phase and a dose expansion phase. The dosage of the Her2 inhibitor in the dose escalation phase will be 20 mg/kg Q2W and 30 mg/kg Q2W; and the dosage of the dimer in the dose escalation phase will be 3 mg/kg Q2W. The mTPI (Modified Toxicity Probability Interval) will be perform in this phase. A mTPI-2 group subjects with increasing or decreasing dosage to determine the maximum tolerated dose (MTD) according to a calculated design. An isotonic regression of mTPI-2 will be applied to the observed DLT (dose limiting toxicity) to estimate the MTD as the dosage most close to the target DLT after the dose escalation phase.

A first dose group (the Her2 inhibitor 6 20 mg/kg Q2W+ the dimer 3 mg/kg Q2W) will engage 3-6 subjects. The SMC will be performed after DLT observing and the subjects of the first dose group will be grouped into a second group (the Her2 inhibitor 6 30 mg/kg Q2W+the dimer 3 mg/kg Q2W) if meeting the "ascending to a higher dose" criteria according to the mTPI-2 design table. The second group will engage 3-6 subject and the first dose group will expand to 12 subjects meanwhile. The second dose group will expand to 12 subjects when the subjects meet the "ascending to a higher dose" criteria or "maintain the original dose" criteria and the whole DLT observing of the dose escalation phase will end.

After dose escalation phase, a RP2D (Recommended Phase II Dose) will be determined by the SMC and the study will be in the dose expansion phase. The SMC will determine an original dose, increasing intermediate dose group, or increasing other groups (e.g., fixed-dose administration, different dosing intervals, such as Q3W) at the same dose level according to safety, PK data and/or other data of the Her2 inhibitor and the dimer; or, performing a higher dose study (e.g., the dimer 5 mg/kg).

Primary Study Endpoint:
the dose escalation phase: DLT (dose-limiting toxicity);
the dose expansion phase: ORR (objective response rate) determined by RECIST 1.1; and DOR (duration of response).

The results show that the Her2 inhibitor in combination with the dimer of the present disclosure will treat the Her2 positive tumor effectively in subjects.

Example 2 Preliminary Safety, Tolerability and
Efficacy Results of KN026 (a Her2-Targeted
Bispecific Antibody) in Combination with KN046
(an Anti-PD-L1/CTLA-4 Bispecific Antibody) in
Patients (Pts) with Her2 Aberrated Solid Tumor Background:

Her2 potently inhibits innate immunity through cGAS-STING signaling, meanwhile Her2 antibody induced ADCP will also lead to macrophage mediated immune suppression. Both preclinical and clinical studies have suggested a coordination of engagement of innate and adaptive immunity with the combination of an anti-Her2 antibody and an immune checkpoint blockade. KN026 is a novel bispecific antibody that simultaneously binds to two distinct Her2 epitopes. KN046 is a novel bispecific antibody that blocks both PD-L1 interaction with PD-1/CD80 and CTLA-4 interaction with CD80/CD86. Here we reported the interim results from an ongoing phase Ib dose escalation and expansion study assessing the safety, tolerability and preliminary efficacy for KN026 in combination with KN046 in Patients with Her2 aberrated solid tumors.

Methods:

This study enrolled pts with solid tumors who failed available standard of care, Her2 aberration status confirmed locally (Her2 mutation, Her2 amplification and/or Her2 overexpression). Eligible pts received combination of KN026 and KN046 at three dose levels until disease progression, unacceptable toxicity or withdrawal of informed consent (DL1: KN026 20 mg/kg Q2W+KN046 3 mg/kg Q2W; DL2: KN026 20 mg/kg Q2W with loading on Days 1, 8 of Cycle 1+KN046 5 mg/kg Q3W; DL3: KN026 30 mg/kg Q3W with loading on Days 1, 8 of Cycle 1+KN046 5 mg/kg Q3W). Tumor response was evaluated Q8W per RECIST 1.1. Primary endpoint was DLT and key secondary endpoints were efficacy parameters (ORR, DOR, PFS).

Results:

As of the Sep. 8, 2020, 25 pts were enrolled into DL1 (n=20, 3 for dose escalation), DL2 (n=3) and DL3 (n=2) (mGC/GEJ 15 pts; mCRC 8 pts; other solid tumors 2 pts). 15 pts remained on the study treatment and 10 pts discontinued treatment due to disease progression (n=5), death (n=2) and other reasons (n=3). 18 pts had Her2-positive status (12 of 18 failed previous trastuzumab therapy), 2 pts had Her2 mutation and 5 pts had Her2 low expression (without FISH amplification). No DLTs were observed. No pts experienced LVEF decreased or other clinically meaningful cardiac AEs. Treatment-related TEAEs occurred in 23 (92%) pts, of which 6 (24%) pts experienced grade 3 or above treatment-related TEAEs. 11 (44%) pts experienced irAEs, majority were of grade 1 or 2 except that 1 patient experienced grade 3 immune-mediated endocrinopathy. The most common (frequency≥15%) KN026 or KN046 related TEAEs were infusion related reaction (n=11, 44.0%), anaemia (n=9, 36.0%), white blood cell count decreased (n=6, 24.0%), diarrhea (n=5, 20.0%), AST increased (n=5, 20.0%), platelet count decreased (n=5, 20.0%), rash (n=5, 20.0%) and ALT increased (n=4, 16.0%). The objective response rate in pts with Her2-positive tumors (n=14 efficacy evaluable pts) was 9/14 (64.3%, 95% CI 35.187.2%) and disease control rate 13/14 (92.9%, 95% CI 66.199.8%). 4 out of 5 pts with Her2 mutation or low expression achieved SD including one patient with SD for more than 24 weeks. 2 death cases due to disease progression were reported, both only received one cycle of KN026 plus KN046 due to COVID-19 restriction.

Conclusions: KN026 combined with KN046 is well tolerated and has demonstrated profound anti-tumor activity in Her2-positive solid tumors preliminarily.

Clinical Trial Information: NCT04040699

Example 3 Preliminary Breakthrough Therapy
Designation Request (BTDR) Advice

This document will be used as a basis for the Division to comment on whether a request for a Breakthrough Therapy Designation (BTD) is appropriate, at this time, may be too preliminary, or does not currently meet the BTD criteria.

1. Provide Information Related to Whether the Indication is Serious and Life-Threatening. Briefly Describe the Indication and the Disease for which the Product is Intended:

Indication which the product is intended is Her2-positive (Her2 IHC3+ or Her2 IHC2+/FISH+) gastric/gastroesophageal junction adenocarcinoma and esophageal adenocarcinoma (GC/GEJ/EAC).

2. Briefly Describe the Drug, the Drug's Mechanism of Action (if Known), the Drug's Relation to Existing Therapy (ies):

KN026 is a Her2 bispecific antibody simultaneously targeting Her2 domains II and IV; KN046 is a PD-L1/CTLA-4 bispecific antibody blocking PD1/PD-L1 and CTLA-4 pathways.

3. Briefly Describe Available Therapies, if any:

Fluoropyrimidine, platinum and trastuzumab based regimen is commonly used as the first line therapy. Available second or later line therapies include paclitaxel plus ramucirumab, paclitaxel, docetaxel or irinotecan monotherapy, and best supportive care, inducing approx. 15-25% objective response rate. Median overall survival is about 8-9 months at second line and 4-6 month at late line with large unmet medical need.

4. Provide Information Related to the Preliminary Clinical Evidence*, Including Trial Design, Trial Endpoints, Treatment Groups, and Number of Subjects Enrolled:

KN046-IST-02 (NCT04040699) is an ongoing dose escalation and expansion study to evaluate efficacy and safety of KN046 plus KN026 in Her2-positive solid tumors. As of 3 Sep. 2020, 14 patients with Her2-positive solid tumors were enrolled and evaluable for efficacy, including 9 patients with Her2-positive GC/GEJ. 64.3% (9/14) response rate was observed in Her2-positive solid tumors and 66.7% (6/9) response rate in Her2-positive GC/GEJ. All 14 patients have failed at least one prior line of systemic therapy; 10 patients have failed prior trastuzumab therapy where 60% (6/10) objective response rate was observed; 2 patients failed both trastuzumab and anti-PD-1 agent with one partial response and one stable disease.

For example, for Oncology/Hematology products, preliminary clinical evidence could include response rates, duration of response, and extent of prior therapies.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for treating tumor in a subject in need thereof, comprising administering to said subject an immune checkpoint inhibitor in combination with a Her2 inhibitor, wherein said immune checkpoint inhibitor is capable of specifically binding to PD-L1 (programmed death-ligand 1) and CTLA4 (cytotoxic T-lymphocyte associated protein 4), wherein said immune checkpoint inhibitor is a dimer, and said dimer formed by two polypeptide chains, with each of said two polypeptide chains comprising an antibody Fc subunit, wherein said dimer comprises two or more immunoglobulin single variable domains (ISVDs), at least one of said ISVDs is specific for PD-L1, and at least one of said ISVDs is specific for CTLA4, wherein said ISVD specific for PD-L1 comprises heavy chain CDR1-3 (complementarity determining region), said CDR3 comprises an amino acid sequence as set forth in SEQ ID NO: 5, said CDR2 comprises an amino acid sequence as set forth in SEQ ID NO: 4, and said CDR1 comprises an amino acid sequence as set forth in SEQ ID NO: 3, wherein said ISVD specific for CTLA4 comprises heavy chain CDR1-3, said CDR3 comprises an amino acid sequence as set forth in SEQ ID NO: 19, said CDR2 comprises an amino acid sequence as set forth in SEQ ID NO: 18, and said CDR1 comprising an amino acid sequence as set forth in SEQ ID NO: 17, and wherein said Her2 inhibitor is a bispecific antibody, and said bispecific antibody has a common light chain and two heavy chains, wherein the variable region of the common light chain comprises the sequence as set forth in amino acid positions 1 to 107 of SEQ ID NO: 65; and wherein the heavy chain variable regions comprise sequences as set forth in SEQ ID NO: 87 and SEQ ID NO: 88, respectively.

2. The method according to claim 1, wherein for one or both of said two polypeptide chains, said ISVD specific for PD-L1 is fused to said ISVD specific for CTLA4, optionally via a linker.

3. The method according to claim 1, wherein said ISVD specific for PD-L1 is capable of binding to N-terminal IgV (immunoglobulin variable) domain of human PD-L1.

4. The method according to claim 1, wherein said ISVD specific for PD-L1 is capable of binding to a conformational epitope of human PD-L1 N-terminal IgV domain, wherein said conformational epitope comprises residues I54, Y56, E58, Q66, R113, D61, N63, V68, M115, S117, Y123 and R125 of said human PD-L1 N-terminal IgV domain, and wherein said human PD-L1 N-terminal IgV domain comprises an amino acid sequence as set forth in SEQ ID NO: 64.

5. The method according to claim 1, wherein said ISVD specific for PD-L1 comprises a heavy chain variable domain comprising an amino acid sequence as set forth in any one of SEQ ID NO: 6, 10, 12, 13, 14 and 15.

6. The method according to claim 1, wherein said ISVD specific for CTLA4 comprises a heavy chain variable domain comprising an amino acid sequence as set forth in any one of SEQ ID NO: 20, 22, and 24-32.

7. The method according to claim 1, wherein one or both of said two polypeptide chains comprises an amino acid sequence as set forth in any one of SEQ ID NO: 40-43, 46, 48 and 50.

8. The method according to claim 1, wherein said Her2 inhibitor is administrated at dose of 0.01 mg/kg to 100 mg/kg, and/or said immune checkpoint inhibitor is administrated at dose of 0.01 mg/kg to 100 mg/kg.

9. The method according to claim 1, wherein said Her2 inhibitor is administrated at a dosing frequency of four times a week, twice a week, once a week, once every two weeks, once every three weeks, once every four weeks, once every five weeks, once every six weeks, once every eight weeks or once every twelve weeks, and/or said immune checkpoint inhibitor is administrated at a dosing frequency of about four times a week, twice a week, once a week, once every two weeks, once every three weeks, once every four weeks, once every five weeks, once every six weeks, once every eight weeks, once every nine weeks, or once every twelve weeks.

10. The method according to claim 1, wherein said tumor is selected from a group consisting of a solid tumor and a hematologic tumor.

11. A pharmaceutical composition comprising an effective amount of said immune checkpoint inhibitor and an effective amount of said Her2 inhibitor according to claim 1, and optionally a pharmaceutically acceptable excipient.

12. A method for treating tumor in a subject in need thereof, comprising administering to said subject the pharmaceutical composition according to claim 11.

\* \* \* \* \*